US009562220B2

(12) United States Patent
Umeno et al.

(10) Patent No.: US 9,562,220 B2
(45) Date of Patent: Feb. 7, 2017

(54) METHOD FOR PRODUCING CAROTENOIDS EACH HAVING 50 CARBON ATOMS

(75) Inventors: Daisuke Umeno, Chiba (JP); Maiko Furubayashi, Chiba (JP); Norihiko Misawa, Ishikawa (JP); Shinichi Takaichi, Kanagawa (JP)

(73) Assignee: National University Corporation Chiba University, Chiba (JP)

( * ) Notice: Subject to any disclaimer, the term of this patent is extended or adjusted under 35 U.S.C. 154(b) by 0 days.

(21) Appl. No.: 14/124,256

(22) PCT Filed: Jun. 8, 2012

(86) PCT No.: PCT/JP2012/064817
§ 371 (c)(1), (2), (4) Date: Mar. 6, 2014

(87) PCT Pub. No.: WO2012/169623
PCT Pub. Date: Dec. 13, 2012

(65) Prior Publication Data

US 2014/0170700 A1 Jun. 19, 2014

(30) Foreign Application Priority Data

Jun. 10, 2011 (JP) ................................ 2011-130326

(51) Int. Cl.

| | |
|---|---|
| ***C12P 23/00*** | (2006.01) |
| ***C12N 1/20*** | (2006.01) |
| ***C12N 1/00*** | (2006.01) |
| ***C07H 21/04*** | (2006.01) |
| ***C07K 1/00*** | (2006.01) |
| ***C12N 9/02*** | (2006.01) |
| ***C12P 5/02*** | (2006.01) |

(52) U.S. Cl.
CPC ............... *C12N 9/001* (2013.01); *C12P 5/026* (2013.01); *C12P 23/00* (2013.01); *C12Y 103/99029* (2013.01); *Y02P 20/52* (2015.11)

(58) Field of Classification Search
CPC .......... C12P 23/00; C12P 5/026; C12N 9/001; Y02P 20/52; C12Y 103/99029
USPC ..... 435/67, 252.3, 252.33, 254.11; 536/23.1, 536/23.2; 530/350
See application file for complete search history.

(56) References Cited

U.S. PATENT DOCUMENTS 7,288,387 B2 * 10/2007 Cheng et al. .................. 435/67
2005/0260699 A1 * 11/2005 Desouza et al. ................ 435/67

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Office Action issued in corresponding Japanese Patent Application No. 2013-519547 dated Apr. 21, 2016 with English translation (11 pages).
Tobias et al., "Biosynthesis of novel carotenoid families based on unnatural carbon backbones: a model for diversification of natural product pathways," Biochimica et Biophysica Acta, 2006, vol. 1761, Issue 2, pp. 235-246.
Umeno, D., "Construction of Artificial Metabolic Networks," Experimental Medicine, 2011, vol. 29, No. 7, pp. 61-67 (25 pages) with English translation.
Stickforth et al., "Kinetic variations determine the product pattern of phytoene desaturase from Rubrivivax gelatinosus," Archives of Biochemistry and Biophysics, 2007, vol. 461, No. 2, pp. 235-241.
Wang et al., "Alteration of Product Specificity of Rhodobacter sphaeroides Phytoene Desaturase by Directed Evolution," The Journal of Biological Chemistry, 2001, vol. 276, No. 44, pp. 41161-41164.
Stickforth et al., "Structural and kinetics properties of a mutated phytoene desaturase from Rubrivivax gelatinosus with modified product specificity," Archives of Biochemistry and Biophysics, 2011, vol. 505, No. 1, pp. 118-122.

* cited by examiner

*Primary Examiner* — Ganapathirama Raghu
(74) *Attorney, Agent, or Firm* — Kilyk & Bowersox, P.L.L.C.

(57) ABSTRACT

The present invention provides a method of producing a carotenoid having 50 carbon atoms which comprises culturing, in a medium, a cell transformed with a mutant phytoene desaturase gene and obtaining the carotenoid having 50 carbon atoms from the culture. The mutant phytoene desaturase gene has an introduced mutation to encode a mutant phytoene desaturase having an enhanced activity to desaturate a carotenoid backbone compound of 50 carbon atoms.

17 Claims, 20 Drawing Sheets

$^{1}$H-NMR $CDCl_3$ $^{13}$C-NMR $CDCl_3$ pAC-CrtM$_{F26A,W38A,F233S}$-FDS$_{Y81A,V157A}$ + a pUC-pBAD-CrtI$_{N304P}$-CrtY-CrtG-CrtZ$_{BD}$ b pUC-pBAD-CrtI$_{N304P}$-CrtY-CrtX-CrtZ$_{BD}$ c pUC-pBAD-CrtI$_{N304P}$-CrtY-CrtZ$_{BD}$ d pUC-pBAD-CrtI$_{N304P}$-CrtY-CrtG-CrtW$_{BD}$-CrtZ$_{BD}$ e pUC-pBAD-CrtI$_{N304P}$-CrtY-CrtX-CrtW$_{BD}$-CrtZ$_{BD}$ f pUC-pBAD-CrtI$_{N304P}$-CrtY-CrtW$_{BD}$-CrtZ$_{BD}$ (q)

(r)

(s)

SEQUENCE LISTING

```
<160> NUMBER OF SEQ ID NOS: 28

<210> SEQ ID NO 1
<211> LENGTH: 492
<212> TYPE: PRT
<213> ORGANISM: Pantoea ananatis

<400> SEQUENCE: 1

Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Leu Glu Gln
            20                  25                  30

Arg Asp Lys Pro Gly Gly Arg Ala Tyr Val Tyr Glu Asp Gln Gly Phe
        35                  40                  45

Thr Phe Asp Ala Gly Pro Thr Val Ile Thr Asp Pro Ser Ala Ile Glu
    50                  55                  60

Glu Leu Phe Ala Leu Ala Gly Lys Gln Leu Lys Glu Tyr Val Glu Leu
65                  70                  75                  80

Leu Pro Val Thr Pro Phe Tyr Arg Leu Cys Trp Glu Ser Gly Lys Val
```

-continued

```
                85                  90                  95

Phe Asn Tyr Asp Asn Asp Gln Thr Arg Leu Glu Ala Gln Ile Gln Gln
            100                 105                 110

Phe Asn Pro Arg Asp Val Glu Gly Tyr Arg Gln Phe Leu Asp Tyr Ser
        115                 120                 125

Arg Ala Val Phe Lys Glu Gly Tyr Leu Lys Leu Gly Thr Val Pro Phe
    130                 135                 140

Leu Ser Phe Arg Asp Met Leu Arg Ala Ala Pro Gln Leu Ala Lys Leu
145                 150                 155                 160

Gln Ala Trp Arg Ser Val Tyr Ser Lys Val Ala Ser Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
    210                 215                 220

Gln Gly Met Ile Lys Leu Phe Gln Asp Leu Gly Gly Glu Val Val Leu
225                 230                 235                 240

Asn Ala Arg Val Ser His Met Glu Thr Thr Gly Asn Lys Ile Glu Ala
                245                 250                 255

Val His Leu Glu Asp Gly Arg Arg Phe Leu Thr Gln Ala Val Ala Ser
            260                 265                 270

Asn Ala Asp Val Val His Thr Tyr Arg Asp Leu Leu Ser Gln His Pro
        275                 280                 285

Ala Ala Val Lys Gln Ser Asn Lys Leu Gln Thr Lys Arg Met Ser Asn
    290                 295                 300

Ser Leu Phe Val Leu Tyr Phe Gly Leu Asn His His His Asp Gln Leu
305                 310                 315                 320

Ala His His Thr Val Cys Phe Gly Pro Arg Tyr Arg Glu Leu Ile Asp
                325                 330                 335

Glu Ile Phe Asn His Asp Gly Leu Ala Glu Asp Phe Ser Leu Tyr Leu
            340                 345                 350

His Ala Pro Cys Val Thr Asp Ser Ser Leu Ala Pro Glu Gly Cys Gly
        355                 360                 365

Ser Tyr Tyr Val Leu Ala Pro Val Pro His Leu Gly Thr Ala Asn Leu
    370                 375                 380

Asp Trp Thr Val Glu Gly Pro Lys Leu Arg Asp Arg Ile Phe Ala Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Gln Leu Asn Ala Tyr His
            420                 425                 430

Gly Ser Ala Phe Ser Val Glu Pro Val Leu Thr Gln Ser Ala Trp Phe
        435                 440                 445

Arg Pro His Asn Arg Asp Lys Thr Ile Thr Asn Leu Tyr Leu Val Gly
    450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490
```

<210> SEQ ID NO 2

-continued

<211> LENGTH: 1479
<212> TYPE: DNA
<213> ORGANISM: Pantoea ananatis

<400> SEQUENCE: 2
atgaaaccaa ctacggtaat tggtgcaggc ttcggtggcc tggcactggc aattcgtcta 60
caagctgcgg ggatccccgt cttactgctt gaacaacgtg ataaacccgg cggtcgggct 120
tatgtctacg aggatcaggg gtttaccttt gatgcaggcc cgacggttat caccgatccc 180
agtgccattg aagaactgtt tgcactggca ggaaaacagt taaaagagta tgtcgaactg 240
ctgccggtta cgccgtttta ccgcctgtgt tgggagtcag ggaaggtctt taattacgat 300
aacgatcaaa cccggctcga agcgcagatt cagcagttta atccccgcga tgtcgaaggt 360
tatcgtcagt ttctggacta ttcacgcgcg gtgtttaaag aaggctatct aaagctcggt 420
actgtccctt ttttatcgtt cagagacatg cttcgcgccg cacctcaact ggcgaaactg 480
caggcatgga gaagcgttta cagtaaggtt gccagttaca tcgaagatga acatctgcgc 540
caggcgtttt ctttccactc gctgttggtg ggcggcaatc ccttcgccac ctcatccatt 600
tatacgttga tacacgcgct ggagcgtgag tggggcgtct ggtttccgcg tggcggcacc 660
ggcgcattag ttcaggggat gataaagctg tttcaggatc tgggtggcga agtcgtgtta 720
aacgccagag tcagccatat ggaaacgaca ggaaacaaga ttgaagccgt gcatttagag 780
gacggtcgca ggttcctgac gcaagccgtc gcgtcaaatg cagatgtggt tcatacctat 840
cgcgacctgt taagccagca ccctgccgcg gttaagcagt ccaacaaact gcagactaag 900
cgcatgagta actctctgtt tgtgctctat tttggtttga atcaccatca tgatcagctc 960
gcgcatcaca cggtttgttt cggcccgcgt taccgcgagc tgattgacga aatttttaat 1020
catgatggcc tcgcagagga cttctcactt tatctgcacg cgccctgtgt cacggattcg 1080
tcactggcgc ctgaaggttg cggcagttac tatgtgttgg cgccggtgcc acatttaggc 1140
accgcgaacc tcgactggac ggttgagggg ccaaaactac gcgaccgtat ttttgcgtac 1200
cttgagcagc attacatgcc tggcttacgg agtcagctgg tcacgcaccg gatgtttacg 1260
ccgtttgatt ttcgcgacca gcttaatgcc tatcatggct cagccttttc tgtggagccc 1320
gttcttaccc agagcgcctg gtttcggccg cataaccgcg ataaaaccat tactaatctc 1380
tacctggtcg gcgcaggcac gcatcccggc gcaggcattc ctggcgtcat cggctcggca 1440
aaagcgacag caggtttgat gctggaggat ctgatttga 1479

<210> SEQ ID NO 3
<211> LENGTH: 1479
<212> TYPE: DNA
<213> ORGANISM: Artificial Sequence
<220> FEATURE:
<223> OTHER INFORMATION: Pantoea ananatis crtI mutant (N304S)

<400> SEQUENCE: 3
atgaaaccaa ctacggtaat tggtgcaggc ttcggtggcc tggcactggc aattcgtcta 60
caagctgcgg ggatccccgt cttactgctt gaacaacgtg ataaacccgg cggtcgggct 120
tatgtctacg aggatcaggg gtttaccttt gatgcaggcc cgacggttat caccgatccc 180
agtgccattg aagaactgtt tgcactggca ggaaaacagt taaaagagta tgtcgaactg 240
ctgccggtta cgccgtttta ccgcctgtgt tgggagtcag ggaaggtctt taattacgat 300
aacgatcaaa cccggctcga agcgcagatt cagcagttta atccccgcga tgtcgaaggt 360
tatcgtcagt ttctggacta ttcacgcgcg gtgtttaaag aaggctatct aaagctcggt 420

-continued actgtccctt ttttatcgtt cagagacatg cttcgcgccg cacctcaact ggcgaaactg 480
caggcatgga gaagcgttta cagtaaggtt gccagttaca tcgaagatga acatctgcgc 540
caggcgtttt ctttccactc gctgttggtg ggcggcaatc ccttcgccac ctcatccatt 600
tatacgttga tacacgcgct ggagcgtgag tggggcgtct ggtttccgcg tggcggcacc 660
ggcgcattag ttcaggggat gataaagctg tttcaggatc tgggtggcga agtcgtgtta 720
aacgccagag tcagccatat ggaaacgaca ggaaacaaga ttgaagccgt gcatttagag 780
gacggtcgca ggttcctgac gcaagccgtc gcgtcaaatg cagatgtggt tcatacctat 840
cgcgacctgt taagccagca ccctgccgcg gttaagcagt ccaacaaact gcagactaag 900
cgcatgagta gctctctgtt tgtgctctat tttggtttga atcaccatca tgatcagctc 960
gcgcatcaca cggtttgttt cggcccgcgt taccgcgagc tgattgacga aatttttaat 1020
catgatggcc tcgcagagga cttctcactt tatctgcacg cgccctgtgt cacggattcg 1080
tcactggcgc ctgaaggttg cggcagttac tatgtgttgg cgccggtgcc acatttaggc 1140
accgcgaacc tcgactggac ggttgagggg ccaaaactac gcgaccgtat ttttgcgtac 1200
cttgagcagc attacatgcc tggcttacgg agtcagctgg tcacgcaccg gatgtttacg 1260
ccgtttgatt ttcgcgacca gcttaatgcc tatcatggct cagccttttc tgtggagccc 1320
gttcttaccc agagcgcctg gtttcggccg cataaccgcg ataaaaccat tactaatctc 1380
tacctggtcg gcgcaggcac gcatcccggc gcaggcattc ctggcgtcat cggctcggca 1440
aaagcgacag caggtttgat gctggaggat ctgatttga 1479

<210> SEQ ID NO 4
<211> LENGTH: 894
<212> TYPE: DNA
<213> ORGANISM: Artificial Sequence
<220> FEATURE:
<223> OTHER INFORMATION: Geobacillus stearothermophillus fds mutant
(Y81A, V157A)

<400> SEQUENCE: 4
atggcgcagc tttcagttga acagtttctc aacgagcaaa aacaggcggt ggaaacagcg 60
ctctcccgtt atatagagcg cttagaaggg ccggcgaagc tgaaaaaggc gatggcgtac 120
tcattggagg ccggcggcaa acgaatccgt ccgttgctgc ttctgtccac cgttcgggcg 180
ctcggcaaag acccggcggt cggattgccc gtcgcctgcg cgattgaaat gatccatacg 240
gcatctttga tccatgatga tttgccgagc atggacaacg atgatttgcg gcgcggcaag 300
ccgacgaacc ataaagtgtt cggcgaggcg atggccatct tggcgggggga cgggttgttg 360 acgtacgcgt ttcaattgat caccgaaatc gacgatgagc gcatccctcc ttccgtccgg 420
cttcggctca tcgaacggct ggcgaaagcg gccggtccgg aagggatggc ggccggtcag 480
gcagccgata tggaaggaga ggggaaaacg ctgacgcttt cggagctcga atacattcat 540
cggcataaaa ccgggaaaat gctgcaatac agcgtgcacg ccggcgcctt gatcggcggc 600
gctgatgccc ggcaaacgcg ggagcttgac gaattcgccg cccatctagg ccttgccttt 660
caaattcgcg atgatattct cgatattgaa ggggcagaag aaaaaatcgg caagccggtc 720
ggcagcgacc aaagcaacaa caaagcgacg tatccagcgt tgctgtcgct tgccggcgcg 780
aaggaaaagt tggcgttcca tatcgaggcg gcgcagcgcc atttacggaa cgctgacgtt 840
gacggcgccg cgctcgccta tatttgcgaa ctggtcgccg cccgcgacca ttaa 894

-continued

<210> SEQ ID NO 5
<211> LENGTH: 864
<212> TYPE: DNA
<213> ORGANISM: Artificial Sequence
<220> FEATURE:
<223> OTHER INFORMATION: Staphylococcus aureus crtM mutant (F26A, W38A, F233S)

<400> SEQUENCE: 5

```
atgacaatga tgaatatgaa ttttaaatat tgtcataaaa tcatgaagaa acattcaaaa     60

agcttttctt acgctgcgga cttgttacca gaagatcaaa gaaaagcggt tgcggcaatt    120

tatgctgtgt gtcgtaaaat tgatgacagt atagatgttt atggcgatat tcaattttta    180

aatcaaataa aagaagatat acaatctatt gaaaaatacc catatgaaca tcatcacttt    240

caaagtgatc gtagaatcat gatggcgctt cagcatgttg cacaacataa aaatatcgcc    300

tttcaatctt tttataatct cattgatact gtatataaag atcaacattt tacaatgttt    360

gaaacggacg ctgaattatt cggatattgt tatggtgttg ctggtacagt aggtgaagta    420

ttgacgccga ttttaagtga tcatgaaaca catcagacat acgatgtcgc aagaagactt    480

ggtgaatcgt tgcaattgat taatatatta agagatgtcg gtgaagattt tgacaatgaa    540

cggatatatt ttagtaagca acgattaaag caatatgaag ttgatattgc tgaagtgtac    600

caaaatggtg ttaataatca ttatattgac ttatgggaat attatgcagc tatcgcagaa    660

aaagatttttc aagatgttat ggatcaaatc aaagtatcta gtattgaagc acaaccaatc    720

atagaattag cagcacgtat atatattgaa atactggacg aagtgagaca ggctaactat    780

acattacatg aacgtgtttt tgtggataag aggaaaaagg caaagttgtt tcatgaaata    840

aatagtaaat atcatagaat atag                                           864
```

<210> SEQ ID NO 6
<211> LENGTH: 2503
<212> TYPE: DNA
<213> ORGANISM: Artificial Sequence
<220> FEATURE:
<223> OTHER INFORMATION: crtZWY gene derived from Paracoccus sp., N81106 strain

<400> SEQUENCE: 6

```
ggcgaccttg cggcgctgcg ccgcgcgcct ttgctggtgc ctgggccggg tggccaatgg     60

tcgcaagcaa cggggatgga aaccggcgat gcgggactgt agtctgcgcg gatcgccggt    120

ccgggggaca agatgagcgc acatgccctg cccaaggcag atctgaccgc caccagcctg    180

atcgtctcgg gcggcatcat cgccgcttgg ctggccctgc atgtgcatgc gctgtggttt    240

ctggacgcag cggcgcatcc catcctggcg atcgcaaatt tcctggggct gacctggctg    300

tcggtcggat tgttcatcat cgcgcatgac gcgatgcacg ggtcggtggt gccggggcgt    360

ccgcgcgcca atgcggcgat gggccagctt gtcctgtggc tgtatgccgg attttcgtgg    420

cgcaagatga tcgtcaagca catggcccat caccgccatg ccggaaccga cgacgacccc    480

gatttcgacc atggcggccc ggtccgctgg tacgcccgct tcatcggcac ctatttcggc    540

tggcgcgagg ggctgctgct gcccgtcatc gtgacggtct atgcgctgat ccttggggat    600

cgctggatgt acgtggtctt ctggccgctg ccgtcgatcc tggcgtcgat ccagctgttc    660

gtgttcggca cctggctgcc gcaccgcccc ggccacgacg cgttcccgga ccgccacaat    720

gcgcggtcgt cgcggatcag cgaccccgtg tcgctgctga cctgctttca ctttggcggt    780

tatcatcacg aacaccacct gcacccgacg gtgccgtggt ggcgcctgcc cagcacccgc    840
```

-continued accaaggggg acaccgcatg accaatttcc tgatcgtcgt cgccaccgtg ctggtgatgg 900
agttgacggc ctattccgtc caccgctgga tcatgcacgg ccccctgggc tggggctggc 960
acaagtccca ccacgaggaa cacgaccacg cgctggaaaa gaacgacctg tacggcctgg 1020
tctttgcggt gatcgccacg gtgctgttca cggtgggctg gatctgggcg ccggtcctgt 1080
ggtggatcgc cttgggcatg actgtctatg ggctgatcta tttcgtcctg catgacgggc 1140
tggtgcatca gcgctggccg ttccgttata tcccgcgcaa gggctatgcc agacgcctgt 1200
atcaggccca ccgcctgcac catgcggtcg aggggcgcga ccattgcgtc agcttcggct 1260
tcatctatgc gcccccggtc gacaagctga agcaggacct gaagatgtcg ggcgtgctgc 1320
gggccgaggc gcaggagcgc acgtgaccca tgacgtgctg ctggcagggg cgggccttgc 1380
caacgggctg atcgccctgg cgctgcgcgc ggcgcggccc gacctgcgcg tgctgctgct 1440
ggaccatgcc gcaggaccgt cagacggcca cacctggtcc tgccacgacc ccgacctgtc 1500
gccggactgg ctggcgcggc tgaagcccct gcgccgcgcc aactggcccg accaggaggt 1560
gcgctttccc cgccatgccc ggcggctggc caccggttac gggtcgctgg acggggcggc 1620
gctggcggat gcggtggtcc ggtcgggcgc cgagatccgc tgggacagcg acatcgccct 1680
gctggatgcg caggggggcga cgctgtcctg cggcacccgg atcgaggcgg gcgcggtcct 1740
ggacgggcgg ggcgcgcagc cgtcgcggca tctgaccgtg ggtttccaga aattcgtggg 1800
tgtcgagatc gagaccgacc gcccccacgg cgtgccccgc ccgatgatca tggacgcgac 1860
cgtcacccag caggacgggt accgcttcat ctatctgctg cccttctctc cgacgcgcat 1920
cctgatcgag gacacgcgct attccgatgg cggcgatctg gacgacgacg cgctggcggc 1980
ggcgtcccac gactatgccc gccagcaggg ctggaccggg gccgaggtcc ggcgcgaacg 2040
cggcatcctt cccatcgcgc tggcccatga tgcggcgggc ttctgggccg atcacgcggc 2100
ggggcctgtt cccgtgggac tgcgcgcggg gttctttcat ccggtcaccg gctattcgct 2160
gccctatgcg gcacaggtgg cggacgtggt ggcgggtctg tccgggccgc ccggcaccga 2220
cgcgctgcgc ggcgccatcc gcgattacgc gatcgaccgg gcgcgccgcg accgctttct 2280
gcgccttttg aaccggatgc tgttccgcgg ctgcgcgccc gaccggcgct ataccctgct 2340
gcagcggttc taccgcatgc cgcatggact gatcgaacgg ttctatgccg gccggctgag 2400
cgtggcggat cagctgcgca tcgtgaccgg caagcctccc attccccttg gcacggccat 2460
ccgctgcctg cccgaacgtc ccctgctgaa ggaaaacgca tga 2503

<210> SEQ ID NO 7
<211> LENGTH: 726
<212> TYPE: DNA
<213> ORGANISM: Rhodobacter capsulatus

<400> SEQUENCE: 7
atgccagtcg ccagccttag cttattcaga tttgatggca ccagctccct gccgtgggtg 60
attagccaaa tgatcttgtc tcgtcgtcca ctgaacgacg aaccgcgtgt gaagttctat 120
aagctgtgcg gcagcggcac gggtgagggc ttcaccccga aaccgaattg gcgtgtttgg 180
gcaattatgg cggcgttcga caccgaggcg gatgcacgcg atgtcacggc aaaccatccg 240
gtttggaaac gttggcgtgc acacgcggca gaaaccctgg tgctgcattt gcagcctctg 300
tcggcccgtg gcacctgggg cggtgtgaat ccgttcctgc cggagcaggt ggcggagccg 360
agcccggacg agccggtcgt tgcgctgacc cgtgcggcga ttaaaccgca caaagcgaat 420
gctttttgga gccgcgtgcc gaagattagc gagaaagttg gtgaagatca gaacctgatg 480

-continued

```
tttaagatcg gtatcggtga gattccgctg tttcaccaag ttacgttttc catctggcct    540

gatgtcgcga aaatgaacgc cttcgcccgt ggtgacaccc cgcacggtaa ggcaatccgc    600

gctgcccgcg aagagggttg gttcacggaa gaactgtacg ctcgctttcg cctgctgggc    660

accgagggta gctggatggg taaagacccg ctggcgagca aggttctgga acgtgagact    720

gcgtaa                                                               726
```

```
<210> SEQ ID NO 8
<211> LENGTH: 5425
<212> TYPE: DNA
<213> ORGANISM: Artificial Sequence
<220> FEATURE:
<223> OTHER INFORMATION: Designed plasmid DNA, pAC-crtMF26A,W38A,F233S

<400> SEQUENCE: 8
```

```
gaattccgga tgagcattca tcaggcgggc aagaatgtga ataaaggccg gataaaactt     60

gtgcttattt ttctttacgg tctttaaaaa ggccgtaata tccagctgaa cggtctggtt    120

ataggtacat tgagcaactg actgaaatgc ctcaaaatgt tctttacgat gccattggga    180

tatatcaacg gtggtatatc cagtgatttt tttctccatt ttagcttcct tagctcctga    240

aaatctcgat aactcaaaaa atacgcccgg tagtgatctt atttcattat ggtgaaagtt    300

ggaacctctt acgtgccgat caacgtctca ttttcgccaa aagttggccc agggcttccc    360

ggtatcaaca gggacaccag gatttattta ttctgcgaag tgatcttccg tcacaggtat    420

ttattcggcg caaagtgcgt cgggtgatgc tgccaactta ctgatttagt gtatgatggt    480

gtttttgagg tgctccagtg gcttctgttt ctatcagctg tccctcctgt tcagctactg    540

acggggtggt gcgtaacggc aaaagcaccg ccggacatca gcgctagcgg agtgtatact    600

ggcttactat gttggcactg atgagggtgt cagtgaagtg cttcatgtgg caggagaaaa    660

aaggctgcac cggtgcgtca gcagaatatg tgatacagga tatattccgc ttcctcgctc    720

actgactcgc tacgctcggt cgttcgactg cggcgagcgg aaatggctta cgaacggggc    780

ggagatttcc tggaagatgc caggaagata cttaacaggg aagtgagagg gccgcggcaa    840

agccgttttt ccataggctc cgcccccctg acaagcatca cgaaatctga cgctcaaatc    900

agtggtggcg aaacccgaca ggactataaa gataccaggc gtttccccct ggcggctccc    960

tcgtgcgctc tcctgttcct gcctttcggt ttaccggtgt cattccgctg ttatggccgc   1020

gtttgtctca ttccacgcct gacactcagt tccgggtagg cagttcgctc caagctggac   1080

tgtatgcacg aaccccccgt tcagtccgac cgctgcgcct tatccggtaa ctatcgtctt   1140

gagtccaacc cggaaagaca tgcaaaagca ccactggcag cagccactgg taattgattt   1200

agaggagtta gtcttgaagt catgcgccgg ttaaggctaa actgaaagga caagttttgg   1260

tgactgcgct cctccaagcc agttacctcg gttcaaagag ttggtagctc agagaacctt   1320

cgaaaaaccg ccctgcaagg cggttttttc gttttcagag caagagatta cgcgcagacc   1380

aaaacgatct caagaagatc atcttattaa tcagataaaa tatttcaaga tttcagtgca   1440

atttatctct tcaaatgtag cacctgaagt cagccccata cgatataagt tgtaattctc   1500

atgtttgaca gcttatcatc gataagcttt aatgcggtag tttatcacag ttaaattgct   1560

aacgcagtca ggcaccgtgt atgaaatcta acaatgcgct catcgtcatc ctcggcaccg   1620

tcaccctgga tgctgtaggc ataggcttgg ttatgccggt actgccgggc ctcttgcggg   1680

atatcgtcca ttccgacagc atcgccagtc actatggcgt gctgctagcg ctatatgcgt   1740
```

-continued

```
tgatgcaatt tctatgcgca cccgttctcg gagcactgtc cgaccgcttt ggccgccgcc   1800
cagtcctgct cgcttcgcta cttggagcca ctatcgacta cgcgatcatg gcgaccacac   1860
ccgtcctgtg gatcccgtgg aggtttcccg actggaaagc gggcagtgag cgcaacgcaa   1920
ttaatgtgag ttagctcact cattaggcac cccaggcttt acactttatg cttccggctc   1980
gtatgttgtg tggaattgtg agcggataac aatttcacac aggaaacaca tatggaattc   2040
tctagaagga ggattacaaa atgacaatga tgaatatgaa ttttaaatat tgtcataaaa   2100
tcatgaagaa acattcaaaa agcttttctt acgctgcgga cttgttacca gaagatcaaa   2160
gaaaagcggt tgcggcaatt tatgctgtgt gtcgtaaaat tgatgacagt atagatgttt   2220
atggcgatat tcaattttta aatcaaataa aagaagatat acaatctatt gaaaaatacc   2280
catatgaaca tcatcacttt caaagtgatc gtagaatcat gatggcgctt cagcatgttg   2340
cacaacataa aaatatcgcc tttcaatctt tttataatct cattgatact gtatataaag   2400
atcaacattt tacaatgttt gaaacggacg ctgaattatt cggatattgt tatggtgttg   2460
ctggtacagt aggtgaagta ttgacgccga ttttaagtga tcatgaaaca catcagacat   2520
acgatgtcgc aagaagactt ggtgaatcgt tgcaattgat taatatatta agagatgtcg   2580
gtgaagattt tgacaatgaa cggatatatt ttagtaagca acgattaaag caatatgaag   2640
ttgatattgc tgaagtgtac caaaatggtg ttaataatca ttatattgac ttatgggaat   2700
attatgcagc tatcgcagaa aaagattttc aagatgttat ggatcaaatc aaagtatcta   2760
gtattgaagc acaaccaatc atagaattag cagcacgtat atatattgaa atactggacg   2820
aagtgagaca ggctaactat acattacatg aacgtgtttt tgtggataag aggaaaaagg   2880
caaagttgtt tcatgaaata aatagtaaat atcatagaat atagctcgag gggcccggcg   2940
cctgatgcgg tattttctcc ttacgcatct gtgcggtatt tcacgtgcgc tcgaggggcc   3000
cggcgcctga tgcggtattt tctccttacg catctgtgcg gtatttcacg gatcctctac   3060
gccggacgca tcgtggccgg catcaccggc gccacaggtg cggttgctgg cgcctatatc   3120
gccgacatca ccgatgggga agatcgggct cgccacttcg ggctcatgag cgcttgtttc   3180
ggcgtgggta tggtggcagg ccccgtggcc gggggactgt tgggcgccat ctccttgcat   3240
gcaccattcc ttgcggcggc ggtgctcaac ggcctcaacc tactactggg ctgcttccta   3300
atgcaggagt cgcataaggg agagcgtcga ccgatgccct tgagagcctt caacccagtc   3360
agctccttcc ggtgggcgcg gggcatgact atcgtcgccg cacttatgac tgtcttcttt   3420
atcatgcaac tcgtaggaca ggtgccggca gcgctctggg tcattttcgg cgaggaccgc   3480
tttcgctgga gcgcgacgat gatcggcctg tcgcttgcgg tattcggaat cttgcacgcc   3540
ctcgctcaag ccttcgtcac tggtcccgcc accaaacgtt tcggcgagaa gcaggccatt   3600
atcgccggca tggcggccga cgcgctgggc tacgtcttgc tggcgttcgc gacgcgaggc   3660
tggatggcct tccccattat gattcttctc gcttccggcg gcatcgggat gcccgcgttg   3720
caggccatgc tgtccaggca ggtagatgac gaccatcagg gacagcttca aggatcgctc   3780
gcggctctta ccagcctaac ttcgatcact ggaccgctga tcgtcacggc gatttatgcc   3840
gcctcggcga gcacatggaa cgggttggca tggattgtag gcgccgccct ataccttgtc   3900
tgcctccccg cgttgcgtcg cggtgcatgg agccgggcca cctcgacctg aatggaagcc   3960
ggcggcacct cgctaacgga ttcaccactc caagaattgg agccaatcaa ttcttgcgga   4020
gaactgtgaa tgcgcaaacc aacccttggc agaacatatc catcgcgtcc gccatctcca   4080
gcagccgcac gcggcgcatc tcgggcagcg ttgggtcctg gccacgggtg cgcatgatcg   4140
```

```
tgctcctgtc gttgaggacc cggctaggct ggcggggttg ccttactggt tagcagaatg   4200

aatcaccgat acgcgagcga acgtgaagcg actgctgctg caaaacgtct gcgacctgag   4260

caacaacatg aatggtcttc ggtttccgtg tttcgtaaag tctggaaacg cggaagtccc   4320

ctacgtgctg ctgaagttgc ccgcaacaga gagtggaacc aaccggtgat accacgatac   4380

tatgactgag agtcaacgcc atgagcggcc tcatttctta ttctgagtta caacagtccg   4440

caccgctgtc cggtagctcc ttccggtggg cgcggggcat gactatcgtc gccgcactta   4500

tgactgtctt ctttatcatg caactcgtag gacaggtgcc ggcagcgccc aacagtcccc   4560

cggccacggg gcctgccacc atacccacgc cgaaacaagc gccctgcacc attatgttcc   4620

ggatctgcat cgcaggatgc tgctggctac cctgtggaac acctacatct gtattaacga   4680

agcgctaacc gtttttatca ggctctggga ggcagaataa atgatcatat cgtcaattat   4740

tacctccacg gggagagcct gagcaaactg gcctcaggca tttgagaagc acacggtcac   4800

actgcttccg gtagtcaata aaccggtaaa ccagcaatag acataagcgg ctatttaacg   4860

accctgccct gaaccgacga ccgggtcgaa tttgctttcg aatttctgcc attcatccgc   4920

ttattatcac ttattcaggc gtagcaccag gcgtttaagg gcaccaataa ctgccttaaa   4980

aaaattacgc ccgccctgc cactcatcgc agtactgttg taattcatta agcattctgc    5040

cgacatggaa gccatcacag acggcatgat gaacctgaat cgccagcggc atcagcacct   5100

tgtcgccttg cgtataatat ttgcccatgg tgaaaacggg ggcgaagaag ttgtccatat   5160

tggccacgtt taaatcaaaa ctggtgaaac tcacccaggg attggctgag acgaaaaaca   5220

tattctcaat aaacccttta gggaaatagg ccaggttttc accgtaacac gccacatctt   5280

gcgaatatat gtgtagaaac tgccggaaat cgtcgtggta ttcactccag agcgatgaaa   5340

acgtttcagt ttgctcatgg aaaacggtgt aacaagggtg aacactatcc catatcacca   5400

gctcaccgtc tttcattgcc atacg                                          5425
```

<210> SEQ ID NO 9
<211> LENGTH: 3394
<212> TYPE: DNA
<213> ORGANISM: Artificial Sequence
<220> FEATURE:
<223> OTHER INFORMATION: Designed plasmid DNA, pUC-fdsY81A, V157A

<400> SEQUENCE: 9

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cacatatgga attctctaga aggaggagta    240

agcgatggcg cagctttcag ttgaacagtt tctcaacgag caaaaacagg cggtggaaac    300

agcgctctcc cgttatatag agcgcttaga agggccggcg aagctgaaaa aggcgatggc    360

gtactcattg gaggccggcg gcaaacgaat ccgtccgttg ctgcttctgt ccaccgttcg    420

ggcgctcggc aaagacccgg cggtcggatt gcccgtcgcc tgcgcgattg aaatgatcca    480

tacggcatct ttgatccatg atgatttgcc gagcatggac aacgatgatt tgcggcgcgg    540

caagccgacg aaccataaag tgttcggcga ggcgatggcc atcttggcgg gggacgggtt    600

gttgacgtac gcgtttcaat tgatcaccga aatcgacgat gagcgcatcc ctccttccgt    660

ccggcttcgg ctcatcgaac ggctggcgaa agcggccggt ccggaaggga tggcggccgg    720
```

-continued

```
tcaggcagcc gatatggaag gagaggggaa aacgctgacg ctttcggagc tcgaatacat    780
tcatcggcat aaaaccggga aaatgctgca atacagcgtg cacgccggcg ccttgatcgg    840
cggcgctgat gcccggcaaa cgcgggagct tgacgaattc gccgcccatc taggccttgc    900
ctttcaaatt cgcgatgata ttctcgatat tgaaggggca gaagaaaaaa tcggcaagcc    960
ggtcggcagc gaccaaagca acaacaaagc gacgtatcca gcgttgctgt cgcttgccgg   1020
cgcgaaggaa aagttggcgt tccatatcga ggcggcgcag cgccatttac ggaacgctga   1080
cgttgacggc gccgcgctcg cctatatttg cgaactggtc gccgcccgcg accattaact   1140
cgaggggccc ggcgcctgat gcggtatttt ctccttacgc atctgtgcgg tatttcacac   1200
cgcatatatg gtgcactctc agtacaatct gctctgatgc cgcatagtta agccagcccc   1260
gacacccgcc aacacccgct gacgcgccct gacgggcttg tctgctcccg gcatccgctt   1320
acagacaagc tgtgaccgtc tccgggagct gcatgtgtca gaggttttca ccgtcatcac   1380
cgaaacgcgc gagacgaaag ggcctcgtga tacgcctatt tttataggtt aatgtcatga   1440
taataatggt ttcttagacg tcaggtggca cttttcgggg aaatgtgcgc ggaaccccta   1500
tttgtttatt tttctaaata cattcaaata tgtatccgct catgagacaa taaccctgat   1560
aaatgcttca ataatattga aaaaggaaga gtatgagtat tcaacatttc cgtgtcgccc   1620
ttattccctt ttttgcggca ttttgccttc ctgtttttgc tcacccagaa acgctggtga   1680
aagtaaaaga tgctgaagat cagttgggtg cacgagtggg ttacatcgaa ctggatctca   1740
acagcggtaa gatccttgag agttttcgcc ccgaagaacg ttttccaatg atgagcactt   1800
ttaaagttct gctatgtggc gcggtattat cccgtattga cgccgggcaa gagcaactcg   1860
gtcgccgcat acactattct cagaatgact tggttgagta ctcaccagtc acagaaaagc   1920
atcttacgga tggcatgaca gtaagagaat tatgcagtgc tgccataacc atgagtgata   1980
acactgcggc caacttactt ctgacaacga tcggaggacc gaaggagcta accgcttttt   2040
tgcacaacat gggggatcat gtaactcgcc ttgatcgttg ggaaccggag ctgaatgaag   2100
ccataccaaa cgacgagcgt gacaccacga tgcctgtagc aatggcaaca acgttgcgca   2160
aactattaac tggcgaacta cttactctag cttcccggca acaattaata gactggatgg   2220
aggcggataa agttgcagga ccacttctgc gctcggccct tccggctggc tggtttattg   2280
ctgataaatc tggagccggt gagcgtgggt ctcgcggtat cattgcagca ctggggccag   2340
atggtaagcc ctcccgtatc gtagttatct acacgacggg gagtcaggca actatggatg   2400
aacgaaatag acagatcgct gagataggtg cctcactgat taagcattgg taactgtcag   2460
accaagttta ctcatatata ctttagattg atttaaaact tcatttttaa tttaaaagga   2520
tctaggtgaa gatccttttt gataatctca tgaccaaaat cccttaacgt gagttttcgt   2580
tccactgagc gtcagacccc gtagaaaaga tcaaaggatc ttcttgagat cctttttttc   2640
tgcgcgtaat ctgctgcttg caaacaaaaa aaccaccgct accagcggtg gtttgtttgc   2700
cggatcaaga gctaccaact ctttttccga aggtaactgg cttcagcaga gcgcagatac   2760
caaatactgt ccttctagtg tagccgtagt taggccacca cttcaagaac tctgtagcac   2820
cgcctacata cctcgctctg ctaatcctgt taccagtggc tgctgccagt ggcgataagt   2880
cgtgtcttac cgggttggac tcaagacgat agttaccgga taaggcgcag cggtcgggct   2940
gaacgggggg ttcgtgcaca cagcccagct tggagcgaac gacctacacc gaactgagat   3000
acctacagcg tgagctatga gaaagcgcca cgcttcccga agggagaaag gcggacaggt   3060
atccggtaag cggcagggtc ggaacaggag agcgcacgag ggagcttcca gggggaaacg   3120
```

-continued

```
cctggtatct ttatagtcct gtcgggtttc gccacctctg acttgagcgt cgatttttgt   3180

gatgctcgtc aggggggcgg agcctatgga aaaacgccag caacgcggcc tttttacggt   3240

tcctggcctt ttgctggcct tttgctcaca tgttctttcc tgcgttatcc cctgattctg   3300

tggataaccg tattaccgcc tttgagtgag ctgataccgc tcgccgcagc cgaacgaccg   3360

agcgcagcga gtcagtgagc gaggaagcgg aaga                               3394


<210> SEQ ID NO 10
<211> LENGTH: 6220
<212> TYPE: DNA
<213> ORGANISM: Artificial Sequence
<220> FEATURE:
<223> OTHER INFORMATION: Designed plasmid DNA, pAC-crtMF26A,W38A,F233S-
      idi

<400> SEQUENCE: 10

gaattccgga tgagcattca tcaggcgggc aagaatgtga ataaaggccg gataaaactt     60

gtgcttattt ttctttacgg tctttaaaaa ggccgtaata tccagctgaa cggtctggtt    120

ataggtacat tgagcaactg actgaaatgc ctcaaaatgt tctttacgat gccattggga    180

tatatcaacg gtggtatatc cagtgatttt tttctccatt ttagcttcct tagctcctga    240

aaatctcgat aactcaaaaa atacgcccgg tagtgatctt atttcattat ggtgaaagtt    300

ggaacctctt acgtgccgat caacgtctca ttttcgccaa aagttggccc agggcttccc    360

ggtatcaaca gggacaccag gatttattta ttctgcgaag tgatcttccg tcacaggtat    420

ttattcggcg caaagtgcgt cgggtgatgc tgccaactta ctgatttagt gtatgatggt    480

gtttttgagg tgctccagtg gcttctgttt ctatcagctg tccctcctgt tcagctactg    540

acggggtggt gcgtaacggc aaaagcaccg ccggacatca gcgctagcgg agtgtatact    600

ggcttactat gttggcactg atgagggtgt cagtgaagtg cttcatgtgg caggagaaaa    660

aaggctgcac cggtgcgtca gcagaatatg tgatacagga tatattccgc ttcctcgctc    720

actgactcgc tacgctcggt cgttcgactg cggcgagcgg aaatggctta cgaacggggc    780

ggagatttcc tggaagatgc caggaagata cttaacaggg aagtgagagg gccgcggcaa    840

agccgttttt ccataggctc cgcccccctg acaagcatca cgaaatctga cgctcaaatc    900

agtggtggcg aaacccgaca ggactataaa gataccaggc gtttccccct ggcggctccc    960

tcgtgcgctc tcctgttcct gcctttcggt ttaccggtgt cattccgctg ttatggccgc   1020

gtttgtctca ttccacgcct gacactcagt tccgggtagg cagttcgctc caagctggac   1080

tgtatgcacg aaccccccgt tcagtccgac cgctgcgcct tatccggtaa ctatcgtctt   1140

gagtccaacc cggaaagaca tgcaaaagca ccactggcag cagccactgg taattgattt   1200

agaggagtta gtcttgaagt catgcgccgg ttaaggctaa actgaaagga caagttttgg   1260

tgactgcgct cctccaagcc agttacctcg gttcaaagag ttggtagctc agagaacctt   1320

cgaaaaaccg ccctgcaagg cggttttttc gttttcagag caagagatta cgcgcagacc   1380

aaaacgatct caagaagatc atcttattaa tcagataaaa tatttcaaga tttcagtgca   1440

atttatctct tcaaatgtag cacctgaagt cagccccata cgatataagt tgtaattctc   1500

atgtttgaca gcttatcgtg aggtttcccg actggaaagc gggcagtgag cgcaacgcaa   1560

ttaatgtgag ttagctcact cattaggcac cccaggcttt acactttatg cttccggctc   1620

gtatgttgtg tggaattgtg agcggataac aatttcacac aggaaacaca tatggaattc   1680

tctagaagga ggattacaaa atgcaaacgg aacacgtcat tttattgaat gcacagggag   1740
```

-continued

```
ttcccacggg tacgctggaa aagtatgccg cacacacggc agacacccgc ttacatctcg   1800
cgttctccag ttggctgttt aatgccaaag gacaattatt agttacccgc cgcgcactga   1860
gcaaaaaagc atggcctggc gtgtggacta actcggtttg tgggcaccca caactgggag   1920
aaagcaacga agacgcagtg atccgccgtt gccgttatga gcttggcgtg gaaattacgc   1980
ctcctgaatc tatctatcct gactttcgct accgcgccac cgatccgagt ggcattgtgg   2040
aaaatgaagt gtgtccggta tttgccgcac gcaccactag tgcgttacag atcaatgatg   2100
atgaagtgat ggattatcaa tggtgtgatt tagcagatgt attacacggt attgatgcca   2160
cgccgtgggc gttcagtccg tggatggtga tgcaggcgac aaatcgcgaa gccagaaaac   2220
gattatctgc atttacccag cttaaataac tcgaggggcc cggcgcctga tgcggtattt   2280
tctccttacg catctgtgcg gtatttcact gcatcgataa gctttaatgc ggtagtttat   2340
cacagttaaa ttgctaacgc agtcaggcac cgtgtatgaa atctaacaat gcgctcatcg   2400
tcatcctcgg caccgtcacc ctggatgctg taggcatagg cttggttatg ccggtactgc   2460
cgggcctctt gcgggatatc gtccattccg acagcatcgc cagtcactat ggcgtgctgc   2520
tagcgctata tgcgttgatg caatttctat gcgcacccgt tctcggagca ctgtccgacc   2580
gctttggccg ccgcccagtc ctgctcgctt cgctacttgg agccactatc gactacgcga   2640
tcatggcgac cacacccgtc ctgtggatcc cgtggaggtt tcccgactgg aaagcgggca   2700
gtgagcgcaa cgcaattaat gtgagttagc tcactcatta ggcaccccag gctttacact   2760
ttatgcttcc ggctcgtatg ttgtgtggaa ttgtgagcgg ataacaattt cacacaggaa   2820
acacatatgg aattctctag aaggaggatt acaaaatgac aatgatgaat atgaatttta   2880
aatattgtca taaaatcatg aagaaacatt caaaaagctt ttcttacgct gcggacttgt   2940
taccagaaga tcaaagaaaa gcggttgcgg caatttatgc tgtgtgtcgt aaaattgatg   3000
acagtataga tgtttatggc gatattcaat ttttaaatca aataaaagaa gatatacaat   3060
ctattgaaaa atacccatat gaacatcatc actttcaaag tgatcgtaga atcatgatgg   3120
cgcttcagca tgttgcacaa cataaaaata tcgcctttca atctttttat aatctcattg   3180
atactgtata taaagatcaa cattttacaa tgtttgaaac ggacgctgaa ttattcggat   3240
attgttatgg tgttgctggt acagtaggtg aagtattgac gccgatttta agtgatcatg   3300
aaacacatca gacatacgat gtcgcaagaa gacttggtga atcgttgcaa ttgattaata   3360
tattaagaga tgtcggtgaa gattttgaca atgaacggat atattttagt aagcaacgat   3420
taaagcaata tgaagttgat attgctgaag tgtaccaaaa tggtgttaat aatcattata   3480
ttgacttatg ggaatattat gcagctatcg cagaaaaaga ttttcaagat gttatggatc   3540
aaatcaaagt atttagtatt gaagcacaac caatcataga attagcagca cgtatatata   3600
ttgaaatact ggacgaagtg agacaggcta actatacatt acatgaacgt gtttttgtgg   3660
ataagaggaa aaaggcaaag ttgtttcatg aaataaatag taaatatcat agaatatagc   3720
tcgaggggcc cggcgcctga tgcggtattt tctccttacg catctgtgcg gtatttcacg   3780
tgcgctcgag gggcccggcg cctgatgcgg tattttctcc ttacgcatct gtgcggtatt   3840
tcacggatcc tctacgccgg acgcatcgtg gccggcatca ccggcgccac aggtgcggtt   3900
gctggcgcct atatcgccga catcaccgat ggggaagatc gggctcgcca cttcgggctc   3960
atgagcgctt gtttcggcgt gggtatggtg gcaggccccg tggccggggg actgttgggc   4020
gccatctcct tgcatgcacc attccttgcg gcggcggtgc tcaacggcct caacctacta   4080
```

```
ctgggctgct tcctaatgca ggagtcgcat aagggagagc gtcgaccgat gcccttgaga   4140
gccttcaacc cagtcagctc cttccggtgg gcgcggggca tgactatcgt cgccgcactt   4200
atgactgtct tctttatcat gcaactcgta ggacaggtgc cggcagcgct ctgggtcatt   4260
ttcggcgagg accgctttcg ctggagcgcg acgatgatcg gcctgtcgct tgcggtattc   4320
ggaatcttgc acgccctcgc tcaagccttc gtcactggtc ccgccaccaa acgtttcggc   4380
gagaagcagg ccattatcgc cggcatggcg gccgacgcgc tgggctacgt cttgctggcg   4440
ttcgcgacgc gaggctggat ggccttcccc attatgattc ttctcgcttc cggcggcatc   4500
gggatgcccg cgttgcaggc catgctgtcc aggcaggtag atgacgacca tcagggacag   4560
cttcaaggat cgctcgcggc tcttaccagc ctaacttcga tcactggacc gctgatcgtc   4620
acggcgattt atgccgcctc ggcgagcaca tggaacgggt tggcatggat tgtaggcgcc   4680
gccctatacc ttgtctgcct ccccgcgttg cgtcgcggtg catggagccg ggccacctcg   4740
acctgaatgg aagccggcgg cacctcgcta acggattcac cactccaaga attggagcca   4800
atcaattctt gcggagaact gtgaatgcgc aaaccaaccc ttggcagaac atatccatcg   4860
cgtccgccat ctccagcagc cgcacgcggc gcatctcggg cagcgttggg tcctggccac   4920
gggtgcgcat gatcgtgctc ctgtcgttga ggacccggct aggctggcgg ggttgcctta   4980
ctggttagca gaatgaatca ccgatacgcg agcgaacgtg aagcgactgc tgctgcaaaa   5040
cgtctgcgac ctgagcaaca acatgaatgg tcttcggttt ccgtgtttcg taaagtctgg   5100
aaacgcggaa gtcccctacg tgctgctgaa gttgcccgca acagagagtg gaaccaaccg   5160
gtgataccac gatactatga ctgagagtca acgccatgag cggcctcatt tcttattctg   5220
agttacaaca gtccgcaccg ctgtccggta gctccttccg gtgggcgcgg ggcatgacta   5280
tcgtcgccgc acttatgact gtcttcttta tcatgcaact cgtaggacag gtgccggcag   5340
cgcccaacag tcccccggcc acggggcctg ccaccatacc cacgccgaaa caagcgccct   5400
gcaccattat gttccggatc tgcatcgcag gatgctgctg gctaccctgt ggaacaccta   5460
catctgtatt aacgaagcgc taaccgtttt tatcaggctc tgggaggcag aataaatgat   5520
catatcgtca attattacct ccacggggag agcctgagca aactggcctc aggcatttga   5580
gaagcacacg gtcacactgc ttccggtagt caataaaccg gtaaaccagc aatagacata   5640
agcggctatt taacgaccct gccctgaacc gacgaccggg tcgaatttgc tttcgaattt   5700
ctgccattca tccgcttatt atcacttatt caggcgtagc accaggcgtt taagggcacc   5760
aataactgcc ttaaaaaaat tacgccccgc cctgccactc atcgcagtac tgttgtaatt   5820
cattaagcat tctgccgaca tggaagccat cacagacggc atgatgaacc tgaatcgcca   5880
gcggcatcag caccttgtcg ccttgcgtat aatatttgcc catggtgaaa acgggggcga   5940
agaagttgtc catattggcc acgtttaaat caaaactggt gaaactcacc cagggattgg   6000
ctgagacgaa aaacatattc tcaataaacc ctttagggaa ataggccagg ttttcaccgt   6060
aacacgccac atcttgcgaa tatatgtgta gaaactgccg gaaatcgtcg tggtattcac   6120
tccagagcga tgaaaacgtt tcagtttgct catggaaaac ggtgtaacaa gggtgaacac   6180
tatcccatat caccagctca ccgtctttca ttgccatacg                         6220
```

<210> SEQ ID NO 11
<211> LENGTH: 6565
<212> TYPE: DNA
<213> ORGANISM: Artificial Sequence
<220> FEATURE:
<223> OTHER INFORMATION: Designed plasmid DNA, pAC-fdsY81A, V157A-

-continued crtMF26A,W38A,F233S

<400> SEQUENCE: 11

```
gaattccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttggccc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttccccct ggcggctccc    960
tcgtgcgctc tcctgttcct gcctttcggt ttaccggtgt cattccgctg ttatggccgc   1020
gtttgtctca ttccacgcct gacactcagt tccgggtagg cagttcgctc caagctggac   1080
tgtatgcacg aaccccccgt tcagtccgac cgctgcgcct tatccggtaa ctatcgtctt   1140
gagtccaacc cggaaagaca tgcaaaagca ccactggcag cagccactgg taattgattt   1200
agaggagtta gtcttgaagt catgcgccgg ttaaggctaa actgaaagga caagttttgg   1260
tgactgcgct cctccaagcc agttacctcg gttcaaagag ttggtagctc agagaacctt   1320
cgaaaaaccg ccctgcaagg cggttttttc gttttcagag caagagatta cgcgcagacc   1380
aaaacgatct caagaagatc atcttattaa tcagataaaa tatttcaaga tttcagtgca   1440
atttatctct tcaaatgtag cacctgaagt cagccccata cgatataagt tgtaattctc   1500
atgtttgaca gcttatcgtg aggtttcccg actggaaagc gggcagtgag cgcaacgcaa   1560
ttaatgtgag ttagctcact cattaggcac cccaggcttt acactttatg cttccggctc   1620
gtatgttgtg tggaattgtg agcggataac aatttcacac aggaaacaca tatggaattc   1680
tctagaagga ggagtaagcg atggcgcagc tttcagttga acagtttctc aacgagcaaa   1740
aacaggcggt ggaaacagcg ctctcccgtt atatagagcg cttagaaggg ccggcgaagc   1800
tgaaaaaggc gatggcgtac tcattggagg ccggcggcaa acgaatccgt ccgttgctgc   1860
ttctgtccac cgttcgggcg ctcggcaaag acccggcggt cggattgccc gtcgcctgcg   1920
cgattgaaat gatccatacg gcatctttga tccatgatga tttgccgagc atggacaacg   1980
atgatttgcg gcgcggcaag ccgacgaacc ataaagtgtt cggcgaggcg atggccatct   2040
tggcggggga cgggttgttg acgtacgcgt ttcaattgat caccgaaatc gacgatgagc   2100
gcatccctcc ttccgtccgg cttcggctca tcgaacggct ggcgaaagcg gccggtccgg   2160
aagggatggc ggccggtcag gcagccgata tggaaggaga ggggaaaacg ctgacgcttt   2220
cggagctcga atacattcat cggcataaaa ccgggaaaat gctgcaatac agcgtgcacg   2280
```

-continued

```
ccggcgcctt gatcggcggc gctgatgccc ggcaaacgcg ggagcttgac gaattcgccg   2340
cccatctagg ccttgccttt caaattcgcg atgatattct cgatattgaa ggggcagaag   2400
aaaaaatcgg caagccggtc ggcagcgacc aaagcaacaa caaagcgacg tatccagcgt   2460
tgctgtcgct tgccggcgcg aaggaaaagt tggcgttcca tatcgaggcg gcgcagcgcc   2520
atttacggaa cgctgacgtt gacggcgccg cgctcgccta tatttgcgaa ctggtcgccg   2580
cccgcgacca ttaactcgag gggcccggcg cctgatgcgg tattttctcc ttacgcatct   2640
gtgcggtatt tcactgcatc gataagcttt aatgcggtag tttatcacag ttaaattgct   2700
aacgcagtca ggcaccgtgt atgaaatcta acaatgcgct catcgtcatc ctcggcaccg   2760
tcaccctgga tgctgtaggc ataggcttgg ttatgccggt actgccgggc ctcttgcggg   2820
atatcgtcca ttccgacagc atcgccagtc actatggcgt gctgctagcg ctatatgcgt   2880
tgatgcaatt tctatgcgca cccgttctcg gagcactgtc cgaccgcttt ggccgccgcc   2940
cagtcctgct cgcttcgcta cttggagcca ctatcgacta cgcgatcatg gcgaccacac   3000
ccgtcctgtg gatcccgtgg aggtttcccg actggaaagc gggcagtgag cgcaacgcaa   3060
ttaatgtgag ttagctcact cattaggcac cccaggcttt acactttatg cttccggctc   3120
gtatgttgtg tggaattgtg agcggataac aatttcacac aggaaacaca tatggaattc   3180
tctagaagga ggattacaaa atgacaatga tgaatatgaa ttttaaatat tgtcataaaa   3240
tcatgaagaa acattcaaaa agcttttctt acgctgcgga cttgttacca gaagatcaaa   3300
gaaaagcggt tgcggcaatt tatgctgtgt gtcgtaaaat tgatgacagt atagatgttt   3360
atggcgatat tcaattttta aatcaaataa aagaagatat acaatctatt gaaaaatacc   3420
catatgaaca tcatcacttt caaagtgatc gtagaatcat gatggcgctt cagcatgttg   3480
cacaacataa aaatatcgcc tttcaatctt tttataatct cattgatact gtatataaag   3540
atcaacattt tacaatgttt gaaacggacg ctgaattatt cggatattgt tatggtgttg   3600
ctggtacagt aggtgaagta ttgacgccga ttttaagtga tcatgaaaca catcagacat   3660
acgatgtcgc aagaagactt ggtgaatcgt tgcaattgat taatatatta agagatgtcg   3720
gtgaagattt tgacaatgaa cggatatatt ttagtaagca acgattaaag caatatgaag   3780
ttgatattgc tgaagtgtac caaaatggtg ttaataatca ttatattgac ttatgggaat   3840
attatgcagc tatcgcagaa aaagattttc aagatgttat ggatcaaatc aaagtatcta   3900
gtattgaagc acaaccaatc atagaattag cagcacgtat atatattgaa atactggacg   3960
aagtgagaca ggctaactat acattacatg aacgtgtttt tgtggataag aggaaaaagg   4020
caaagttgtt tcatgaaata aatagtaaat atcatagaat atagctcgag gggcccggcg   4080
cctgatgcgg tattttctcc ttacgcatct gtgcggtatt tcacgtgcgc tcgaggggcc   4140
cggcgcctga tgcggtattt tctccttacg catctgtgcg gtatttcacg gatcctctac   4200
gccggacgca tcgtggccgg catcaccggc gccacaggtg cggttgctgg cgcctatatc   4260
gccgacatca ccgatgggga agatcgggct cgccacttcg ggctcatgag cgcttgtttc   4320
ggcgtgggta tggtggcagg ccccgtggcc gggggactgt tgggcgccat ctccttgcat   4380
gcaccattcc ttgcggcggc ggtgctcaac ggcctcaacc tactactggg ctgcttccta   4440
atgcaggagt cgcataaggg agagcgtcga ccgatgccct tgagagcctt caacccagtc   4500
agctccttcc ggtgggcgcg gggcatgact atcgtcgccg cacttatgac tgtcttcttt   4560
atcatgcaac tcgtaggaca ggtgccggca gcgctctggg tcattttcgg cgaggaccgc   4620
```

```
tttcgctgga gcgcgacgat gatcggcctg tcgcttgcgg tattcggaat cttgcacgcc   4680

ctcgctcaag ccttcgtcac tggtcccgcc accaaacgtt tcggcgagaa gcaggccatt   4740

atcgccggca tggcggccga cgcgctgggc tacgtcttgc tggcgttcgc gacgcgaggc   4800

tggatggcct tccccattat gattcttctc gcttccggcg gcatcgggat gcccgcgttg   4860

caggccatgc tgtccaggca ggtagatgac gaccatcagg gacagcttca aggatcgctc   4920

gcggctctta ccagcctaac ttcgatcact ggaccgctga tcgtcacggc gatttatgcc   4980

gcctcggcga gcacatggaa cgggttggca tggattgtag gcgccgccct ataccttgtc   5040

tgcctccccg cgttgcgtcg cggtgcatgg agccgggcca cctcgacctg aatggaagcc   5100

ggcggcacct cgctaacgga ttcaccactc caagaattgg agccaatcaa ttcttgcgga   5160

gaactgtgaa tgcgcaaacc aacccttggc agaacatatc catcgcgtcc gccatctcca   5220

gcagccgcac gcggcgcatc tcgggcagcg ttgggtcctg gccacgggtg cgcatgatcg   5280

tgctcctgtc gttgaggacc cggctaggct ggcggggttg ccttactggt tagcagaatg   5340

aatcaccgat acgcgagcga acgtgaagcg actgctgctg caaaacgtct gcgacctgag   5400

caacaacatg aatggtcttc ggtttccgtg tttcgtaaag tctggaaacg cggaagtccc   5460

ctacgtgctg ctgaagttgc ccgcaacaga gagtggaacc aaccggtgat accacgatac   5520

tatgactgag agtcaacgcc atgagcggcc tcatttctta ttctgagtta caacagtccg   5580

caccgctgtc cggtagctcc ttccggtggg cgcggggcat gactatcgtc gccgcactta   5640

tgactgtctt ctttatcatg caactcgtag gacaggtgcc ggcagcgccc aacagtcccc   5700

cggccacggg gcctgccacc atacccacgc cgaaacaagc gccctgcacc attatgttcc   5760

ggatctgcat cgcaggatgc tgctggctac cctgtggaac acctacatct gtattaacga   5820

agcgctaacc gtttttatca ggctctggga ggcagaataa atgatcatat cgtcaattat   5880

tacctccacg gggagagcct gagcaaactg gcctcaggca tttgagaagc acacggtcac   5940

actgcttccg gtagtcaata aaccggtaaa ccagcaatag acataagcgg ctatttaacg   6000

accctgccct gaaccgacga ccgggtcgaa tttgctttcg aatttctgcc attcatccgc   6060

ttattatcac ttattcaggc gtagcaccag gcgtttaagg gcaccaataa ctgccttaaa   6120

aaaattacgc cccgccctgc cactcatcgc agtactgttg taattcatta agcattctgc   6180

cgacatggaa gccatcacag acggcatgat gaacctgaat cgccagcggc atcagcacct   6240

tgtcgccttg cgtataatat ttgcccatgg tgaaaacggg ggcgaagaag ttgtccatat   6300

tggccacgtt taaatcaaaa ctggtgaaac tcacccaggg attggctgag acgaaaaaca   6360

tattctcaat aaacccttta gggaaatagg ccaggttttc accgtaacac gccacatctt   6420

gcgaatatat gtgtagaaac tgccggaaat cgtcgtggta ttcactccag agcgatgaaa   6480

acgtttcagt ttgctcatgg aaaacggtgt aacaagggtg aacactatcc catatcacca   6540

gctcaccgtc tttcattgcc atacg                                         6565
```

```
<210> SEQ ID NO 12
<211> LENGTH: 5044
<212> TYPE: DNA
<213> ORGANISM: Artificial Sequence
<220> FEATURE:
<223> OTHER INFORMATION: Designed plasmid DNA, pUC-pBAD-CrtI-m2

<400> SEQUENCE: 12

gcgcccaata cgcaaaccgc ctctccccgc gcgttggccg attcattaat gcagctggca     60

cgacaggttt cccgactgga aagcgccatg gttatgacaa cttgacggct acatcattca    120
```

-continued

```
cttttcttc acaaccggca cggaactcgc tcgggctggc cccggtgcat tttttaaata    180
cccgcgagaa atagagttga tcgtcaaaac caacattgcg accgacggtg gcgataggca    240
tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
ccccttgccc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgatttttc accacccct gaccgcgaat ggtgagattg agaatataac    840
ctttcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat acttttcata ctcccgccat tcagagaaga aaccaattgt ccatattgca   1020
tcagacattg ccgtcactgc gtcttttact ggctcttctc gctaaccaaa ccggtaaccc   1080
cgcttattaa aagcattctg taacaaagcg ggaccaaagc catgacaaaa acgcgtaaca   1140
aaagtgtcta taatcacggc agaaaagtcc acattgatta tttgcacggc gtcacacttt   1200
gctatgccat agcattttta tccataagat tagcggatcc tacctgacgc tttttatcgc   1260
aactctctac tgtttctcca tacccgtttg aattctctag actcgagagg aggattacaa   1320
aatgaaacca actacggtaa ttggtgcagg cttcggtggc ctggcactgg caattcgtct   1380
acaagctgcg gggatccccg tcttactgct tgaacaacgt gataaacccg gcggtcgggc   1440
ttatgtctac gaggatcagg ggtttacctt tgatgcaggc ccgacggtta tcaccgatcc   1500
cagtgccatt gaagaactgt ttgcactggc aggaaaacag ttaaaagagt atgtcgaact   1560
gctgccggtt acgccgtttt accgcctgtg ttgggagtca gggaaggtct ttaattacga   1620
taacgatcaa acccggctcg aagcgcagat tcagcagttt aatccccgcg atgtcgaagg   1680
ttatcgtcag tttctggact attcacgcgc ggtgtttaaa gaaggctatc taaagctcgg   1740
tactgtccct tttttatcgt tcagagacat gcttcgcgcc gcacctcaac tggcgaaact   1800
gcaggcatgg agaagcgttt acagtaaggt tgccagttac atcgaagatg aacatctgcg   1860
ccaggcgttt tctttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt agctctctgt ttgtgctcta ttttggtttg aatcaccatc atgatcagct   2280
cgcgcatcac acggtttgtt tcggcccgcg ttaccgcgag ctgattgacg aaatttttaa   2340
tcatgatggc ctcgcagagg acttctcact ttatctgcac gcgccctgtg tcacggattc   2400
gtcactggcg cctgaaggtt gcggcagtta ctatgtgttg gcgccggtgc cacatttagg   2460
```

-continued

```
caccgcgaac ctcgactgga cggttgaggg gccaaaacta cgcgaccgta tttttgcgta   2520
ccttgagcag cattacatgc ctggcttacg gagtcagctg gtcacgcacc ggatgtttac   2580
gccgtttgat tttcgcgacc agcttaatgc ctatcatggc tcagcctttt ctgtggagcc   2640
cgttcttacc cagagcgcct ggtttcggcc gcataaccgc gataaaacca ttactaatct   2700
ctacctggtc ggcgcaggca cgcatcccgg cgcaggcatt cctggcgtca tcggctcggc   2760
aaaagcgaca gcaggtttga tgctggagga tctgatttga gggccctgat gcggtatttt   2820
ctccttacgc atctgtgcgg tatttcacac cgcatatatg gtgcactctc agtacaatct   2880
gctctgatgc cgcatagtta agccagcccc gacacccgcc aacacccgct gacgcgccct   2940
gacgggcttg tctgctcccg gcatccgctt acagacaagc tgtgaccgtc tccgggagct   3000
gcatgtgtca gaggttttca ccgtcatcac cgaaacgcgc gagacgaaag ggcctcgtga   3060
tacgcctatt tttataggtt aatgtcatga taataatggt ttcttagacg tcaggtggca   3120
cttttcgggg aaatgtgcgc ggaaccccta tttgtttatt tttctaaata cattcaaata   3180
tgtatccgct catgagacaa taaccctgat aaatgcttca ataatattga aaaaggaaga   3240
gtatgagtat tcaacatttc cgtgtcgccc ttattccctt ttttgcggca ttttgccttc   3300
ctgtttttgc tcacccagaa acgctggtga aagtaaaaga tgctgaagat cagttgggtg   3360
cacgagtggg ttacatcgaa ctggatctca acagcggtaa gatccttgag agttttcgcc   3420
ccgaagaacg ttttccaatg atgagcactt ttaaagttct gctatgtggc gcggtattat   3480
cccgtattga cgccgggcaa gagcaactcg gtcgccgcat acactattct cagaatgact   3540
tggttgagta ctcaccagtc acagaaaagc atcttacgga tggcatgaca gtaagagaat   3600
tatgcagtgc tgccataacc atgagtgata acactgcggc caacttactt ctgacaacga   3660
tcggaggacc gaaggagcta accgcttttt tgcacaacat gggggatcat gtaactcgcc   3720
ttgatcgttg ggaaccggag ctgaatgaag ccataccaaa cgacgagcgt gacaccacga   3780
tgcctgtagc aatggcaaca acgttgcgca aactattaac tggcgaacta cttactctag   3840
cttcccggca acaattaata gactggatgg aggcggataa agttgcagga ccacttctgc   3900
gctcggccct tccggctggc tggtttattg ctgataaatc tggagccggt gagcgtgggt   3960
ctcgcggtat cattgcagca ctggggccag atggtaagcc ctcccgtatc gtagttatct   4020
acacgacggg gagtcaggca actatggatg aacgaaatag acagatcgct gagataggtg   4080
cctcactgat taagcattgg taactgtcag accaagttta ctcatatata ctttagattg   4140
atttaaaact tcatttttaa tttaaaagga tctaggtgaa gatccttttt gataatctca   4200
tgaccaaaat cccttaacgt gagttttcgt tccactgagc gtcagacccc gtagaaaaga   4260
tcaaaggatc ttcttgagat cctttttttc tgcgcgtaat ctgctgcttg caaacaaaaa   4320
aaccaccgct accagcggtg gtttgtttgc cggatcaaga gctaccaact ctttttccga   4380
aggtaactgg cttcagcaga gcgcagatac caaatactgt ccttctagtg tagccgtagt   4440
taggccacca cttcaagaac tctgtagcac cgcctacata cctcgctctg ctaatcctgt   4500
taccagtggc tgctgccagt ggcgataagt cgtgtcttac cgggttggac tcaagacgat   4560
agttaccgga taaggcgcag cggtcgggct gaacgggggg ttcgtgcaca cagcccagct   4620
tggagcgaac gacctacacc gaactgagat acctacagcg tgagctatga gaaagcgcca   4680
cgcttcccga agggagaaag gcggacaggt atccggtaag cggcagggtc ggaacaggag   4740
agcgcacgag ggagcttcca gggggaaacg cctggtatct ttatagtcct gtcgggtttc   4800
gccacctctg acttgagcgt cgatttttgt gatgctcgtc agggggcgg agcctatgga   4860
```

aaaacgccag caacgcggcc tttttacggt tcctggcctt ttgctggcct tttgctcaca 4920
tgttctttcc tgcgttatcc cctgattctg tggataaccg tattaccgcc tttgagtgag 4980
ctgataccgc tcgccgcagc cgaacgaccg agcgcagcga gtcagtgagc gaggaagcgg 5040
aaga 5044

<210> SEQ ID NO 13
<211> LENGTH: 6220
<212> TYPE: DNA
<213> ORGANISM: Artificial Sequence
<220> FEATURE:
<223> OTHER INFORMATION: Designed plasmid DNA, pUC-pBAD-CrtI-m2-crtY

<400> SEQUENCE: 13
gcgcccaata cgcaaaccgc ctctccccgc gcgttggccg attcattaat gcagctggca 60
cgacaggttt cccgactgga aagcgccatg gttatgacaa cttgacggct acatcattca 120
ctttttcttc acaaccggca cggaactcgc tcgggctggc cccggtgcat tttttaaata 180
cccgcgagaa atagagttga tcgtcaaaac caacattgcg accgacggtg gcgataggca 240
tccgggtggt gctcaaaagc agcttcgcct ggctgatacg ttggtcctcg cgccagctta 300
agacgctaat ccctaactgc tggcggaaaa gatgtgacag acgcgacggc gacaagcaaa 360
catgctgtgc gacgctggcg atatcaaaat tgctgtctgc caggtgatcg ctgatgtact 420
gacaagcctc gcgtacccga ttatccatcg gtggatggag cgactcgtta atcgcttcca 480
tgcgccgcag taacaattgc tcaagcagat ttatcgccag cagctccgaa tagcgccctt 540
ccccttgccc ggcgttaatg atttgcccaa acaggtcgct gaaatgcggc tggtgcgctt 600
catccgggcg aaagaacccc gtattggcaa atattgacgg ccagttaagc cattcatgcc 660
agtaggcgcg cggacgaaag taaacccact ggtgatacca ttcgcgagcc tccggatgac 720
gaccgtagtg atgaatctct cctggcggga acagcaaaat atcacccggt cggcaaacaa 780
attctcgtcc ctgatttttc accaccccct gaccgcgaat ggtgagattg agaatataac 840
ctttcattcc cagcggtcgg tcgataaaaa aatcgagata accgttggcc tcaatcggcg 900
ttaaacccgc caccagatgg gcattaaacg agtatcccgg cagcagggga tcattttgcg 960
cttcagccat acttttcata ctcccgccat tcagagaaga aaccaattgt ccatattgca 1020
tcagacattg ccgtcactgc gtcttttact ggctcttctc gctaaccaaa ccggtaaccc 1080
cgcttattaa aagcattctg taacaaagcg ggaccaaagc catgacaaaa acgcgtaaca 1140
aaagtgtcta taatcacggc agaaaagtcc acattgatta tttgcacggc gtcacacttt 1200
gctatgccat agcattttta tccataagat tagcggatcc tacctgacgc tttttatcgc 1260
aactctctac tgtttctcca tacccgtttg aattctctag actcgagagg aggattacaa 1320
aatgaaacca actacggtaa ttggtgcagg cttcggtggc ctggcactgg caattcgtct 1380
acaagctgcg gggatccccg tcttactgct tgaacaacgt gataaacccg gcggtcgggc 1440
ttatgtctac gaggatcagg ggtttacctt tgatgcaggc ccgacggtta tcaccgatcc 1500
cagtgccatt gaagaactgt ttgcactggc aggaaaacag ttaaaagagt atgtcgaact 1560
gctgccggtt acgccgtttt accgcctgtg ttgggagtca gggaaggtct ttaattacga 1620
taacgatcaa acccggctcg aagcgcagat tcagcagttt aatccccgcg atgtcgaagg 1680
ttatcgtcag tttctggact attcacgcgc ggtgtttaaa gaaggctatc taaagctcgg 1740
tactgtccct tttttatcgt tcagagacat gcttcgcgcc gcacctcaac tggcgaaact 1800

-continued

```
gcaggcatgg agaagcgttt acagtaaggt tgccagttac atcgaagatg aacatctgcg   1860
ccaggcgttt tctttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt agctctctgt ttgtgctcta ttttggtttg aatcaccatc atgatcagct   2280
cgcgcatcac acggtttgtt tcggcccgcg ttaccgcgag ctgattgacg aaatttttaa   2340
tcatgatggc ctcgcagagg acttctcact ttatctgcac gcgccctgtg tcacggattc   2400
gtcactggcg cctgaaggtt gcggcagtta ctatgtgttg gcgccggtgc cacatttagg   2460
caccgcgaac ctcgactgga cggttgaggg gccaaaacta cgcgaccgta tttttgcgta   2520
ccttgagcag cattacatgc ctggcttacg gagtcagctg gtcacgcacc ggatgtttac   2580
gccgtttgat tttcgcgacc agcttaatgc ctatcatggc tcagcctttt ctgtggagcc   2640
cgttcttacc cagagcgcct ggtttcggcc gcataaccgc gataaaacca ttactaatct   2700
ctacctggtc ggcgcaggca cgcatcccgg cgcaggcatt cctggcgtca tcggctcggc   2760
aaaagcgaca gcaggtttga tgctggagga tctgatttga gggcccgtgt aggaggatta   2820
caaaatgcaa ccgcattatg atctgattct cgtgggggct ggactcgcga atggccttat   2880
cgccctgcgt cttcagcagc agcaacctga tatgcgtatt ttgcttatcg acgccgcacc   2940
ccaggcgggc gggaatcata cgtggtcatt tcaccacgat gatttgactg agagccaaca   3000
tcgttggata gctccgctgg tggttcatca ctggcccgac tatcaggtac gctttcccac   3060
acgccgtcgt aagctgaaca gcggctactt ttgtattact tctcagcgtt tcgctgaggt   3120
tttacagcga cagtttggcc cgcacttgtg gatggatacc gcggtcgcag aggttaatgc   3180
ggaatctgtt cggttgaaaa agggtcaggt tatcggtgcc cgcgcggtga ttgacgggcg   3240
gggttatgcg gcaaattcag cactgagcgt gggcttccag gcgtttattg gccaggaatg   3300
gcgattgagc cacccgcatg gtttatcgtc tcccattatc atggatgcca cggtcgatca   3360
gcaaaatggt tatcgcttcg tgtacagcct gccgctctcg ccgaccagat tgttaattga   3420
agacacgcac tatattgata atgcgacatt agatcctgaa tgcgcgcggc aaaatatttg   3480
cgactatgcc gcgcaacagg gttggcagct tcagacactg ctgcgagaag aacagggcgc   3540
cttacccatt actctgtcgg gcaatgccga cgcattctgg cagcagcgcc ccctggcctg   3600
tagtggatta cgtgccggtc tgttccatcc taccaccggc tattcactgc cgctggcggt   3660
tgccgtggcc gaccgcctga gtgcacttga tgtctttacg tcggcctcaa ttcaccatgc   3720
cattacgcat tttgcccgcg agcgctggca gcagcagggc tttttccgca tgctgaatcg   3780
catgctgttt ttagccggac ccgccgattc acgctggcgg gttatgcagc gtttttatgg   3840
tttacctgaa gatttaattg cccgttttta tgcgggaaaa ctcacgctga ccgatcggct   3900
acgtattctg agcggcaagc cgcctgttcc ggtattagca gcattgcaag ccattatgac   3960
gactcatcgt taaactagtt gctgatgcgg tattttctcc ttacgcatct gtgcggtatt   4020
tcacaccgca tatatggtgc actctcagta caatctgctc tgatgccgca tagttaagcc   4080
agccccgaca cccgccaaca cccgctgacg cgccctgacg ggcttgtctg ctcccggcat   4140
ccgcttacag acaagctgtg accgtctccg ggagctgcat gtgtcagagg ttttcaccgt   4200
```

```
catcaccgaa acgcgcgaga cgaaagggcc tcgtgatacg cctattttta taggttaatg   4260
tcatgataat aatggtttct tagacgtcag gtggcacttt tcggggaaat gtgcgcggaa   4320
cccctatttg tttatttttc taaatacatt caaatatgta tccgctcatg agacaataac   4380
cctgataaat gcttcaataa tattgaaaaa ggaagagtat gagtattcaa catttccgtg   4440
tcgcccttat tccctttttt gcggcatttt gccttcctgt ttttgctcac ccagaaacgc   4500
tggtgaaagt aaaagatgct gaagatcagt tgggtgcacg agtgggttac atcgaactgg   4560
atctcaacag cggtaagatc cttgagagtt ttcgccccga agaacgtttt ccaatgatga   4620
gcacttttaa agttctgcta tgtggcgcgg tattatcccg tattgacgcc gggcaagagc   4680
aactcggtcg ccgcatacac tattctcaga atgacttggt tgagtactca ccagtcacag   4740
aaaagcatct tacggatggc atgacagtaa gagaattatg cagtgctgcc ataaccatga   4800
gtgataacac tgcggccaac ttacttctga caacgatcgg aggaccgaag gagctaaccg   4860
cttttttgca caacatgggg gatcatgtaa ctcgccttga tcgttgggaa ccggagctga   4920
atgaagccat accaaacgac gagcgtgaca ccacgatgcc tgtagcaatg gcaacaacgt   4980
tgcgcaaact attaactggc gaactactta ctctagcttc ccggcaacaa ttaatagact   5040
ggatggaggc ggataaagtt gcaggaccac ttctgcgctc ggcccttccg gctggctggt   5100
ttattgctga taaatctgga gccggtgagc gtgggtctcg cggtatcatt gcagcactgg   5160
ggccagatgg taagccctcc cgtatcgtag ttatctacac gacggggagt caggcaacta   5220
tggatgaacg aaatagacag atcgctgaga taggtgcctc actgattaag cattggtaac   5280
tgtcagacca agtttactca tatatacttt agattgattt aaaacttcat ttttaattta   5340
aaaggatcta ggtgaagatc ctttttgata atctcatgac caaaatccct taacgtgagt   5400
tttcgttcca ctgagcgtca gaccccgtag aaaagatcaa aggatcttct tgagatcctt   5460
tttttctgcg cgtaatctgc tgcttgcaaa caaaaaaacc accgctacca gcggtggttt   5520
gtttgccgga tcaagagcta ccaactcttt ttccgaaggt aactggcttc agcagagcgc   5580
agataccaaa tactgtcctt ctagtgtagc cgtagttagg ccaccacttc aagaactctg   5640
tagcaccgcc tacatacctc gctctgctaa tcctgttacc agtggctgct gccagtggcg   5700
ataagtcgtg tcttaccggg ttggactcaa gacgatagtt accggataag gcgcagcggt   5760
cgggctgaac ggggggttcg tgcacacagc ccagcttgga gcgaacgacc tacaccgaac   5820
tgagatacct acagcgtgag ctatgagaaa gcgccacgct tcccgaaggg agaaaggcgg   5880
acaggtatcc ggtaagcggc agggtcggaa caggagagcg cacgagggag cttccagggg   5940
gaaacgcctg gtatctttat agtcctgtcg ggtttcgcca cctctgactt gagcgtcgat   6000
ttttgtgatg ctcgtcaggg gggcggagcc tatggaaaaa cgccagcaac gcggcctttt   6060
tacggttcct ggccttttgc tggccttttg ctcacatgtt ctttcctgcg ttatcccctg   6120
attctgtgga taaccgtatt accgcctttg agtgagctga taccgctcgc cgcagccgaa   6180
cgaccgagcg cagcgagtca gtgagcgagg aagcggaaga                         6220
```

<210> SEQ ID NO 14
<211> LENGTH: 7553
<212> TYPE: DNA
<213> ORGANISM: Artificial Sequence
<220> FEATURE:
<223> OTHER INFORMATION: Designed plasmid DNA, pUC-pBAD-CrtI-m2-crtWZY

<400> SEQUENCE: 14

-continued

```
gcgcccaata cgcaaaccgc ctctccccgc gcgttggccg attcattaat gcagctggca     60
cgacaggttt cccgactgga aagcgccatg gttatgacaa cttgacggct acatcattca    120
ctttttcttc acaaccggca cggaactcgc tcgggctggc cccggtgcat tttttaaata    180
cccgcgagaa atagagttga tcgtcaaaac caacattgcg accgacggtg gcgataggca    240
tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
ccccttgccc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgatttttc accacccccct gaccgcgaat ggtgagattg agaatataac    840
ctttcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat acttttcata ctcccgccat tcagagaaga aaccaattgt ccatattgca   1020
tcagacattg ccgtcactgc gtcttttact ggctcttctc gctaaccaaa ccggtaaccc   1080
cgcttattaa aagcattctg taacaaagcg ggaccaaagc catgacaaaa acgcgtaaca   1140
aaagtgtcta taatcacggc agaaaagtcc acattgatta tttgcacggc gtcacacttt   1200
gctatgccat agcattttta tccataagat tagcggatcc tacctgacgc tttttatcgc   1260
aactctctac tgtttctcca tacccgtttg aattctctag actcgagagg aggattacaa   1320
aatgaaacca actacggtaa ttggtgcagg cttcggtggc ctggcactgg caattcgtct   1380
acaagctgcg gggatccccg tcttactgct tgaacaacgt gataaacccg gcggtcgggc   1440
ttatgtctac gaggatcagg ggtttacctt tgatgcaggc ccgacggtta tcaccgatcc   1500
cagtgccatt gaagaactgt ttgcactggc aggaaaacag ttaaaagagt atgtcgaact   1560
gctgccggtt acgccgtttt accgcctgtg ttgggagtca gggaaggtct ttaattacga   1620
taacgatcaa acccggctcg aagcgcagat tcagcagttt aatccccgcg atgtcgaagg   1680
ttatcgtcag tttctggact attcacgcgc ggtgtttaaa gaaggctatc taaagctcgg   1740
tactgtccct tttttatcgt tcagagacat gcttcgcgcc gcacctcaac tggcgaaact   1800
gcaggcatgg agaagcgttt acagtaaggt tgccagttac atcgaagatg aacatctgcg   1860
ccaggcgttt tctttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt agctctctgt ttgtgctcta ttttggtttg aatcaccatc atgatcagct   2280
cgcgcatcac acggtttgtt tcggcccgcg ttaccgcgag ctgattgacg aaatttttaa   2340
tcatgatggc ctcgcagagg acttctcact ttatctgcac gcgccctgtg tcacggattc   2400
```

-continued

```
gtcactggcg cctgaaggtt gcggcagtta ctatgtgttg gcgccggtgc cacatttagg   2460
caccgcgaac ctcgactgga cggttgaggg gccaaaacta cgcgaccgta tttttgcgta   2520
ccttgagcag cattacatgc ctggcttacg gagtcagctg gtcacgcacc ggatgtttac   2580
gccgtttgat tttcgcgacc agcttaatgc ctatcatggc tcagcctttt ctgtggagcc   2640
cgttcttacc cagagcgcct ggtttcggcc gcataaccgc gataaaacca ttactaatct   2700
ctacctggtc ggcgcaggca cgcatcccgg cgcaggcatt cctggcgtca tcggctcggc   2760
aaaagcgaca gcaggtttga tgctggagga tctgatttga gggcccggcg accttgcggc   2820
gctgcgccgc gcgcctttgc tggtgcctgg gccgggtggc caatggtcgc aagcaacggg   2880
gatggaaacc ggcgatgcgg gactgtagtc tgcgcggatc gccggtccgg gggacaagat   2940
gagcgcacat gccctgccca aggcagatct gaccgccacc agcctgatcg tctcgggcgg   3000
catcatcgcc gcttggctgg ccctgcatgt gcatgcgctg tggtttctgg acgcagcggc   3060
gcatcccatc ctggcgatcg caaatttcct ggggctgacc tggctgtcgg tcggattgtt   3120
catcatcgcg catgacgcga tgcacgggtc ggtggtgccg gggcgtccgc gcgccaatgc   3180
ggcgatgggc cagcttgtcc tgtggctgta tgccggattt tcgtggcgca agatgatcgt   3240
caagcacatg gcccatcacc gccatgccgg aaccgacgac gaccccgatt tcgaccatgg   3300
cggcccggtc cgctggtacg cccgcttcat cggcacctat ttcggctggc gcgaggggct   3360
gctgctgccc gtcatcgtga cggtctatgc gctgatcctt ggggatcgct ggatgtacgt   3420
ggtcttctgg ccgctgccgt cgatcctggc gtcgatccag ctgttcgtgt tcggcacctg   3480
gctgccgcac cgccccggcc acgacgcgtt cccggaccgc cacaatgcgc ggtcgtcgcg   3540
gatcagcgac cccgtgtcgc tgctgacctg ctttcacttt ggcggttatc atcacgaaca   3600
ccacctgcac ccgacggtgc cgtggtggcg cctgcccagc acccgcacca agggggacac   3660
cgcatgacca atttcctgat cgtcgtcgcc accgtgctgg tgatggagtt gacggcctat   3720
tccgtccacc gctggatcat gcacggcccc ctgggctggg gctggcacaa gtcccaccac   3780
gaggaacacg accacgcgct ggaaaagaac gacctgtacg gcctggtctt tgcggtgatc   3840
gccacggtgc tgttcacggt gggctggatc tgggcgccgg tcctgtggtg gatcgccttg   3900
ggcatgactg tctatgggct gatctatttc gtcctgcatg acgggctggt gcatcagcgc   3960
tggccgttcc gttatatccc gcgcaagggc tatgccagac gcctgtatca ggcccaccgc   4020
ctgcaccatg cggtcgaggg gcgcgaccat tgcgtcagct tcggcttcat ctatgcgccc   4080
ccggtcgaca agctgaagca ggacctgaag atgtcgggcg tgctgcgggc cgaggcgcag   4140
gagcgcacgt gacccatgac gtgctgctgg caggggcggg ccttgccaac gggctgatcg   4200
ccctggcgct gcgcgcggcg cggcccgacc tgcgcgtgct gctgctggac catgccgcag   4260
gaccgtcaga cggccacacc tggtcctgcc acgaccccga cctgtcgccg gactggctgg   4320
cgcggctgaa gcccctgcgc cgcgccaact ggcccgacca ggaggtgcgc tttccccgcc   4380
atgcccggcg gctggccacc ggttacgggt cgctggacgg ggcggcgctg gcggatgcgg   4440
tggtccggtc gggcgccgag atccgctggg acagcgacat cgccctgctg gatgcgcagg   4500
gggcgacgct gtcctgcggc acccggatcg aggcgggcgc ggtcctggac gggcggggcg   4560
cgcagccgtc gcggcatctg accgtgggtt tccagaaatt cgtgggtgtc gagatcgaga   4620
ccgaccgccc ccacggcgtg ccccgcccga tgatcatgga cgcgaccgtc acccagcagg   4680
acgggtaccg cttcatctat ctgctgccct tctctccgac gcgcatcctg atcgaggaca   4740
```

cgcgctattc cgatggcggc gatctggacg acgacgcgct ggcggcggcg tcccacgact 4800
atgcccgcca gcagggctgg accggggccg aggtccggcg cgaacgcggc atccttccca 4860
tcgcgctggc ccatgatgcg gcgggcttct gggccgatca cgcggcgggg cctgttcccg 4920
tgggactgcg cgcggggttc tttcatccgg tcaccggcta ttcgctgccc tatgcggcac 4980
aggtggcgga cgtggtggcg ggtctgtccg ggccgcccgg caccgacgcg ctgcgcggcg 5040
ccatccgcga ttacgcgatc gaccgggcgc gccgcgaccg ctttctgcgc cttttgaacc 5100
ggatgctgtt ccgcggctgc gcgcccgacc ggcgctatac cctgctgcag cggttctacc 5160
gcatgccgca tggactgatc gaacggttct atgccggccg gctgagcgtg gcggatcagc 5220
tgcgcatcgt gaccggcaag cctcccattc cccttggcac ggccatccgc tgcctgcccg 5280
aacgtcccct gctgaaggaa aacgcatgaa ctagttgatg cggtattttc tccttacgca 5340
tctgtgcggt atttcacacc gcatatatgg tgcactctca gtacaatctg ctctgatgcc 5400
gcatagttaa gccagccccg acacccgcca acacccgctg acgcgccctg acgggcttgt 5460
ctgctcccgg catccgctta cagacaagct gtgaccgtct ccgggagctg catgtgtcag 5520
aggttttcac cgtcatcacc gaaacgcgcg agacgaaagg gcctcgtgat acgcctattt 5580
ttataggtta atgtcatgat aataatggtt tcttagacgt caggtggcac ttttcgggga 5640
aatgtgcgcg gaacccctat ttgtttattt ttctaaatac attcaaatat gtatccgctc 5700
atgagacaat aaccctgata aatgcttcaa taatattgaa aaaggaagag tatgagtatt 5760
caacatttcc gtgtcgccct tattcccttt tttgcggcat tttgccttcc tgtttttgct 5820
cacccagaaa cgctggtgaa agtaaaagat gctgaagatc agttgggtgc acgagtgggt 5880
tacatcgaac tggatctcaa cagcggtaag atccttgaga gttttcgccc cgaagaacgt 5940
tttccaatga tgagcacttt taaagttctg ctatgtggcg cggtattatc ccgtattgac 6000
gccgggcaag agcaactcgg tcgccgcata cactattctc agaatgactt ggttgagtac 6060
tcaccagtca cagaaaagca tcttacggat ggcatgacag taagagaatt atgcagtgct 6120
gccataacca tgagtgataa cactgcggcc aacttacttc tgacaacgat cggaggaccg 6180
aaggagctaa ccgctttttt gcacaacatg ggggatcatg taactcgcct tgatcgttgg 6240
gaaccggagc tgaatgaagc cataccaaac gacgagcgtg acaccacgat gcctgtagca 6300
atggcaacaa cgttgcgcaa actattaact ggcgaactac ttactctagc ttcccggcaa 6360
caattaatag actggatgga ggcggataaa gttgcaggac cacttctgcg ctcggccctt 6420
ccggctggct ggtttattgc tgataaatct ggagccggtg agcgtgggtc tcgcggtatc 6480
attgcagcac tggggccaga tggtaagccc tcccgtatcg tagttatcta cacgacgggg 6540
agtcaggcaa ctatggatga acgaaataga cagatcgctg agataggtgc ctcactgatt 6600
aagcattggt aactgtcaga ccaagtttac tcatatatac tttagattga tttaaaactt 6660
catttttaat ttaaaaggat ctaggtgaag atcctttttg ataatctcat gaccaaaatc 6720
ccttaacgtg agttttcgtt ccactgagcg tcagaccccg tagaaaagat caaaggatct 6780
tcttgagatc cttttttttct gcgcgtaatc tgctgcttgc aaacaaaaaa accaccgcta 6840
ccagcggtgg tttgtttgcc ggatcaagag ctaccaactc tttttccgaa ggtaactggc 6900
ttcagcagag cgcagatacc aaatactgtc cttctagtgt agccgtagtt aggccaccac 6960
ttcaagaact ctgtagcacc gcctacatac ctcgctctgc taatcctgtt accagtggct 7020
gctgccagtg gcgataagtc gtgtcttacc gggttggact caagacgata gttaccggat 7080
aaggcgcagc ggtcgggctg aacggggggt tcgtgcacac agcccagctt ggagcgaacg 7140

-continued

```
acctacaccg aactgagata cctacagcgt gagctatgag aaagcgccac gcttcccgaa   7200

gggagaaagg cggacaggta tccggtaagc ggcagggtcg gaacaggaga gcgcacgagg   7260

gagcttccag ggggaaacgc ctggtatctt tatagtcctg tcgggtttcg ccacctctga   7320

cttgagcgtc gatttttgtg atgctcgtca ggggggcgga gcctatggaa aaacgccagc   7380

aacgcggcct ttttacggtt cctggccttt tgctggcctt ttgctcacat gttctttcct   7440

gcgttatccc ctgattctgt ggataaccgt attaccgcct ttgagtgagc tgataccgct   7500

cgccgcagcc gaacgaccga gcgcagcgag tcagtgagcg aggaagcgga aga          7553
```

<210> SEQ ID NO 15
<211> LENGTH: 5797
<212> TYPE: DNA
<213> ORGANISM: Artificial Sequence
<220> FEATURE:
<223> OTHER INFORMATION: Designed plasmid DNA, pUC-pBAD-CrtI-m2-crtA

<400> SEQUENCE: 15

```
gcgcccaata cgcaaaccgc ctctccccgc gcgttggccg attcattaat gcagctggca     60

cgacaggttt cccgactgga aagcgccatg gttatgacaa cttgacggct acatcattca    120

ctttttcttc acaaccggca cggaactcgc tcgggctggc cccggtgcat tttttaaata    180

cccgcgagaa atagagttga tcgtcaaaac caacattgcg accgacggtg gcgataggca    240

tccgggtggt gctcaaaagc agcttcgcct ggctgatacg ttggtcctcg cgccagctta    300

agacgctaat ccctaactgc tggcggaaaa gatgtgacag acgcgacggc gacaagcaaa    360

catgctgtgc gacgctggcg atatcaaaat tgctgtctgc caggtgatcg ctgatgtact    420

gacaagcctc gcgtacccga ttatccatcg gtggatggag cgactcgtta atcgcttcca    480

tgcgccgcag taacaattgc tcaagcagat ttatcgccag cagctccgaa tagcgccctt    540

ccccttgccc ggcgttaatg atttgcccaa acaggtcgct gaaatgcggc tggtgcgctt    600

catccgggcg aaagaacccc gtattggcaa atattgacgg ccagttaagc cattcatgcc    660

agtaggcgcg cggacgaaag taaacccact ggtgatacca ttcgcgagcc tccggatgac    720

gaccgtagtg atgaatctct cctggcggga acagcaaaat atcacccggt cggcaaacaa    780

attctcgtcc ctgatttttc accacccct gaccgcgaat ggtgagattg agaatataac    840

ctttcattcc cagcggtcgg tcgataaaaa aatcgagata accgttggcc tcaatcggcg    900

ttaaacccgc caccagatgg gcattaaacg agtatcccgg cagcagggga tcattttgcg    960

cttcagccat acttttcata ctcccgccat tcagagaaga aaccaattgt ccatattgca   1020

tcagacattg ccgtcactgc gtcttttact ggctcttctc gctaaccaaa ccggtaaccc   1080

cgcttattaa aagcattctg taacaaagcg ggaccaaagc catgacaaaa acgcgtaaca   1140

aaagtgtcta taatcacggc agaaaagtcc acattgatta tttgcacggc gtcacacttt   1200

gctatgccat agcattttta tccataagat tagcggatcc tacctgacgc tttttatcgc   1260

aactctctac tgtttctcca tacccgtttg aattctctag actcgagagg aggattacaa   1320

aatgaaacca actacggtaa ttggtgcagg cttcggtggc ctggcactgg caattcgtct   1380

acaagctgcg gggatccccg tcttactgct tgaacaacgt gataaacccg gcggtcgggc   1440

ttatgtctac gaggatcagg ggtttacctt tgatgcaggc ccgacggtta tcaccgatcc   1500

cagtgccatt gaagaactgt ttgcactggc aggaaaacag ttaaaagagt atgtcgaact   1560

gctgccggtt acgccgtttt accgcctgtg ttgggagtca gggaaggtct ttaattacga   1620
```

-continued

```
taacgatcaa acccggctcg aagcgcagat tcagcagttt aatccccgcg atgtcgaagg   1680
ttatcgtcag tttctggact attcacgcgc ggtgtttaaa gaaggctatc taaagctcgg   1740
tactgtccct tttttatcgt tcagagacat gcttcgcgcc gcacctcaac tggcgaaact   1800
gcaggcatgg agaagcgttt acagtaaggt tgccagttac atcgaagatg aacatctgcg   1860
ccaggcgttt tctttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt agctctctgt ttgtgctcta ttttggtttg aatcaccatc atgatcagct   2280
cgcgcatcac acggtttgtt tcggcccgcg ttaccgcgag ctgattgacg aaatttttaa   2340
tcatgatggc ctcgcagagg acttctcact ttatctgcac gcgccctgtg tcacggattc   2400
gtcactggcg cctgaaggtt gcggcagtta ctatgtgttg gcgccggtgc cacatttagg   2460
caccgcgaac ctcgactgga cggttgaggg gccaaaacta cgcgaccgta tttttgcgta   2520
ccttgagcag cattacatgc ctggcttacg gagtcagctg gtcacgcacc ggatgtttac   2580
gccgtttgat tttcgcgacc agcttaatgc ctatcatggc tcagcctttt ctgtggagcc   2640
cgttcttacc cagagcgcct ggtttcggcc gcataaccgc gataaaacca ttactaatct   2700
ctacctggtc ggcgcaggca cgcatcccgg cgcaggcatt cctggcgtca tcggctcggc   2760
aaaagcgaca gcaggtttga tgctggagga tctgatttga gggcccgtgt aggaggatta   2820
caaaatgcca gtcgccagcc ttagcttatt cagatttgat ggcaccagct ccctgccgtg   2880
ggtgattagc caaatgatct tgtctcgtcg tccactgaac gacgaaccgc gtgtgaagtt   2940
ctataagctg tgcggcagcg gcacgggtga gggcttcacc ccgaaaccga attggcgtgt   3000
ttgggcaatt atggcggcgt tcgacaccga ggcggatgca cgcgatgtca cggcaaacca   3060
tccggtttgg aaacgttggc gtgcacacgc ggcagaaacc ctggtgctgc atttgcagcc   3120
tctgtcggcc cgtggcacct ggggcggtgt gaatccgttc ctgccggagc aggtggcgga   3180
gccgagcccg gacgagccgg tcgttgcgct gacccgtgcg gcgattaaac cgcacaaagc   3240
gaatgctttt tggagccgcg tgccgaagat tagcgagaaa gttggtgaag atcagaacct   3300
gatgtttaag atcggtatcg gtgagattcc gctgtttcac caagttacgt tttccatctg   3360
gcctgatgtc gcgaaaatga acgccttcgc ccgtggtgac accccgcacg gtaaggcaat   3420
ccgcgctgcc cgcgaagagg gttggttcac ggaagaactg tacgctcgct ttcgcctgct   3480
gggcaccgag ggtagctgga tgggtaaaga cccgctggcg agcaaggttc tggaacgtga   3540
gactgcgtaa actagttgct gatgcggtat tttctcctta cgcatctgtg cggtatttca   3600
caccgcatat atggtgcact ctcagtacaa tctgctctga tgccgcatag ttaagccagc   3660
cccgacaccc gccaacaccc gctgacgcgc cctgacgggc ttgtctgctc ccggcatccg   3720
cttacagaca agctgtgacc gtctccggga gctgcatgtg tcagaggttt tcaccgtcat   3780
caccgaaacg cgcgagacga aagggcctcg tgatacgcct atttttatag gttaatgtca   3840
tgataataat ggtttcttag acgtcaggtg gcacttttcg gggaaatgtg cgcggaaccc   3900
ctatttgttt atttttctaa atacattcaa atatgtatcc gctcatgaga caataaccct   3960
gataaatgct tcaataatat tgaaaaagga agagtatgag tattcaacat ttccgtgtcg   4020
```

cccttattcc ctttttttgcg gcattttgcc ttcctgtttt tgctcaccca gaaacgctgg 4080
tgaaagtaaa agatgctgaa gatcagttgg gtgcacgagt gggttacatc gaactggatc 4140
tcaacagcgg taagatcctt gagagttttc gccccgaaga acgttttcca atgatgagca 4200
cttttaaagt tctgctatgt ggcgcggtat tatcccgtat tgacgccggg caagagcaac 4260
tcggtcgccg catacactat tctcagaatg acttggttga gtactcacca gtcacagaaa 4320
agcatcttac ggatggcatg acagtaagag aattatgcag tgctgccata accatgagtg 4380
ataacactgc ggccaactta cttctgacaa cgatcggagg accgaaggag ctaaccgctt 4440
ttttgcacaa catgggggat catgtaactc gccttgatcg ttgggaaccg gagctgaatg 4500
aagccatacc aaacgacgag cgtgacacca cgatgcctgt agcaatggca acaacgttgc 4560
gcaaactatt aactggcgaa ctacttactc tagcttcccg gcaacaatta atagactgga 4620
tggaggcgga taaagttgca ggaccacttc tgcgctcggc ccttccggct ggctggttta 4680
ttgctgataa atctggagcc ggtgagcgtg ggtctcgcgg tatcattgca gcactggggc 4740
cagatggtaa gccctcccgt atcgtagtta tctacacgac ggggagtcag gcaactatgg 4800
atgaacgaaa tagacagatc gctgagatag gtgcctcact gattaagcat tggtaactgt 4860
cagaccaagt ttactcatat atactttaga ttgatttaaa acttcatttt taatttaaaa 4920
ggatctaggt gaagatcctt tttgataatc tcatgaccaa aatcccttaa cgtgagtttt 4980
cgttccactg agcgtcagac cccgtagaaa agatcaaagg atcttcttga gatccttttt 5040
ttctgcgcgt aatctgctgc ttgcaaacaa aaaaaccacc gctaccagcg gtggtttgtt 5100
tgccggatca agagctacca actctttttc cgaaggtaac tggcttcagc agagcgcaga 5160
taccaaatac tgtccttcta gtgtagccgt agttaggcca ccacttcaag aactctgtag 5220
caccgcctac atacctcgct ctgctaatcc tgttaccagt ggctgctgcc agtggcgata 5280
agtcgtgtct taccgggttg gactcaagac gatagttacc ggataaggcg cagcggtcgg 5340
gctgaacggg gggttcgtgc acacagccca gcttggagcg aacgacctac accgaactga 5400
gatacctaca gcgtgagcta tgagaaagcg ccacgcttcc cgaagggaga aaggcggaca 5460
ggtatccggt aagcggcagg gtcggaacag gagagcgcac gagggagctt ccagggggaa 5520
acgcctggta tctttatagt cctgtcgggt ttcgccacct ctgacttgag cgtcgatttt 5580
tgtgatgctc gtcagggggg cggagcctat ggaaaaacgc cagcaacgcg gcctttttac 5640
ggttcctggc cttttgctgg ccttttgctc acatgttctt tcctgcgtta tcccctgatt 5700
ctgtggataa ccgtattacc gcctttgagt gagctgatac cgctcgccgc agccgaacga 5760
ccgagcgcag cgagtcagtg agcgaggaag cggaaga 5797

<210> SEQ ID NO 16
<211> LENGTH: 6994
<212> TYPE: DNA
<213> ORGANISM: Artificial Sequence
<220> FEATURE:
<223> OTHER INFORMATION: Designed plasmid DNA, pUC-pBAD-CrtI-m2-CrtY-CrtWBD

<400> SEQUENCE: 16
gcgcccaata cgcaaaccgc ctctccccgc gcgttggccg attcattaat gcagctggca 60
cgacaggttt cccgactgga aagcgccatg gttatgacaa cttgacggct acatcattca 120
ctttttcttc acaaccggca cggaactcgc tcgggctggc cccggtgcat tttttaaata 180
cccgcgagaa atagagttga tcgtcaaaac caacattgcg accgacggtg gcgataggca 240

-continued

```
tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
ccccttgccc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgatttttc accacccccct gaccgcgaat ggtgagattg agaatataac    840
ctttcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat acttttcata ctcccgccat tcagagaaga aaccaattgt ccatattgca   1020
tcagacattg ccgtcactgc gtcttttact ggctcttctc gctaaccaaa ccggtaaccc   1080
cgcttattaa aagcattctg taacaaagcg ggaccaaagc catgacaaaa acgcgtaaca   1140
aaagtgtcta taatcacggc agaaaagtcc acattgatta tttgcacggc gtcacacttt   1200
gctatgccat agcattttta tccataagat tagcggatcc tacctgacgc tttttatcgc   1260
aactctctac tgtttctcca tacccgtttg aattctctag actcgagagg aggattacaa   1320
aatgaaacca actacggtaa ttggtgcagg cttcggtggc ctggcactgg caattcgtct   1380
acaagctgcg gggatccccg tcttactgct tgaacaacgt gataaacccg gcggtcgggc   1440
ttatgtctac gaggatcagg ggtttacctt tgatgcaggc ccgacggtta tcaccgatcc   1500
cagtgccatt gaagaactgt ttgcactggc aggaaaacag ttaaaagagt atgtcgaact   1560
gctgccggtt acgccgtttt accgcctgtg ttgggagtca gggaaggtct ttaattacga   1620
taacgatcaa acccggctcg aagcgcagat tcagcagttt aatccccgcg atgtcgaagg   1680
ttatcgtcag tttctggact attcacgcgc ggtgtttaaa gaaggctatc taaagctcgg   1740
tactgtccct tttttatcgt tcagagacat gcttcgcgcc gcacctcaac tggcgaaact   1800
gcaggcatgg agaagcgttt acagtaaggt tgccagttac atcgaagatg aacatctgcg   1860
ccaggcgttt tctttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt agctctctgt ttgtgctcta ttttggtttg aatcaccatc atgatcagct   2280
cgcgcatcac acggtttgtt tcggcccgcg ttaccgcgag ctgattgacg aaatttttaa   2340
tcatgatggc ctcgcagagg acttctcact ttatctgcac gcgccctgtg tcacggattc   2400
gtcactggcg cctgaaggtt gcggcagtta ctatgtgttg gcgccggtgc cacatttagg   2460
caccgcgaac ctcgactgga cggttgaggg gccaaaacta cgcgaccgta tttttgcgta   2520
ccttgagcag cattacatgc ctggcttacg gagtcagctg gtcacgcacc ggatgtttac   2580
```

-continued

```
gccgtttgat tttcgcgacc agcttaatgc ctatcatggc tcagcctttt ctgtggagcc   2640
cgttcttacc cagagcgcct ggtttcggcc gcataaccgc gataaaacca ttactaatct   2700
ctacctggtc ggcgcaggca cgcatcccgg cgcaggcatt cctggcgtca tcggctcggc   2760
aaaagcgaca gcaggtttga tgctggagga tctgatttga gggcccgtgt aggaggatta   2820
caaaatgcaa ccgcattatg atctgattct cgtggggggct ggactcgcga atggccttat   2880
cgccctgcgt cttcagcagc agcaacctga tatgcgtatt ttgcttatcg acgccgcacc   2940
ccaggcgggc gggaatcata cgtggtcatt tcaccacgat gatttgactg agagccaaca   3000
tcgttggata gctccgctgg tggttcatca ctggcccgac tatcaggtac gctttcccac   3060
acgccgtcgt aagctgaaca gcggctactt ttgtattact tctcagcgtt tcgctgaggt   3120
tttacagcga cagtttggcc cgcacttgtg gatggatacc gcggtcgcag aggttaatgc   3180
ggaatctgtt cggttgaaaa agggtcaggt tatcggtgcc cgcgcggtga ttgacgggcg   3240
gggttatgcg gcaaattcag cactgagcgt gggcttccag gcgtttattg gccaggaatg   3300
gcgattgagc cacccgcatg gtttatcgtc tcccattatc atggatgcca cggtcgatca   3360
gcaaaatggt tatcgcttcg tgtacagcct gccgctctcg ccgaccagat tgttaattga   3420
agacacgcac tatattgata atgcgacatt agatcctgaa tgcgcgcggc aaaatatttg   3480
cgactatgcc gcgcaacagg gttggcagct tcagacactg ctgcgagaag aacagggcgc   3540
cttacccatt actctgtcgg gcaatgccga cgcattctgg cagcagcgcc ccctggcctg   3600
tagtggatta cgtgccggtc tgttccatcc taccaccggc tattcactgc cgctggcggt   3660
tgccgtggcc gaccgcctga gtgcacttga tgtctttacg tcggcctcaa ttcaccatgc   3720
cattacgcat tttgcccgcg agcgctggca gcagcagggc tttttccgca tgctgaatcg   3780
catgctgttt ttagccggac ccgccgattc acgctggcgg gttatgcagc gtttttatgg   3840
tttacctgaa gatttaattg cccgttttta tgcgggaaaa ctcacgctga ccgatcggct   3900
acgtattctg agcggcaagc cgcctgttcc ggtattagca gcattgcaag ccattatgac   3960
gactcatcgt taaactagat aactagtagg aggattacaa aatgaccgca gctgtcgcag   4020
aacctcgcat tgtaccgcgc caaacctgga tcggcctgac cctggcgggt atgattgtgg   4080
cgggctgggg ttctctgcac gtgtacggtg tgtacttcca ccgttggggc accagcagcc   4140
tggttatcgt cccggctatc gtggccgttc agacgtggtt gtcggttggc ctgtttattg   4200
tcgcacatga cgccatgcac ggttccctgg ccccaggccg tccgcgcctg aacgcagcgg   4260
tgggtcgtct gacgctgggt ctgtatgcag gcttccgttt cgatcgcttg aaaacggcgc   4320
accacgcgca tcatgcggct ccgggtaccg cagatgaccc ggacttttac gcgcctgcgc   4380
cacgcgcctt cctgccgtgg tttttgaact tttccgtac ctatttcggt tggcgcgaga   4440
tggcggttct gaccgcgctg gtcctgatcg cgctgtttgg cttgggtgcc cgtccggcga   4500
atctgttgac tttttgggcc gcaccggcgc tgctgagcgc gctgcaactg ttcacgtttg   4560
gcacctggct gccgcaccgt cacacggacc agccgttcgc ggatgctcat catgcacgca   4620
gcagcggtta tggtccggtt ctgagcctgc tgacctgctt tcatttcggt cgtcatcacg   4680
agcaccacct gacgccgtgg cgtccgtggt ggcgtttgtg gcgtggtgaa agctaaatcg   4740
agctttatct agttgctgat gcggtatttt ctccttacgc atctgtgcgg tatttcacac   4800
cgcatatatg gtgcactctc agtacaatct gctctgatgc cgcatagtta agccagcccc   4860
gacacccgcc aacacccgct gacgcgccct gacgggcttg tctgctcccg gcatccgctt   4920
acagacaagc tgtgaccgtc tccgggagct gcatgtgtca gaggttttca ccgtcatcac   4980
```

-continued

```
cgaaacgcgc gagacgaaag ggcctcgtga tacgcctatt tttataggtt aatgtcatga   5040

taataatggt ttcttagacg tcaggtggca cttttcgggg aaatgtgcgc ggaaccccta   5100

tttgtttatt tttctaaata cattcaaata tgtatccgct catgagacaa taaccctgat   5160

aaatgcttca ataatattga aaaaggaaga gtatgagtat tcaacatttc cgtgtcgccc   5220

ttattccctt ttttgcggca ttttgccttc ctgtttttgc tcacccagaa acgctggtga   5280

aagtaaaaga tgctgaagat cagttgggtg cacgagtggg ttacatcgaa ctggatctca   5340

acagcggtaa gatccttgag agttttcgcc ccgaagaacg ttttccaatg atgagcactt   5400

ttaaagttct gctatgtggc gcggtattat cccgtattga cgccgggcaa gagcaactcg   5460

gtcgccgcat acactattct cagaatgact tggttgagta ctcaccagtc acagaaaagc   5520

atcttacgga tggcatgaca gtaagagaat tatgcagtgc tgccataacc atgagtgata   5580

acactgcggc caacttactt ctgacaacga tcggaggacc gaaggagcta accgcttttt   5640

tgcacaacat gggggatcat gtaactcgcc ttgatcgttg ggaaccggag ctgaatgaag   5700

ccataccaaa cgacgagcgt gacaccacga tgcctgtagc aatggcaaca acgttgcgca   5760

aactattaac tggcgaacta cttactctag cttcccggca acaattaata gactggatgg   5820

aggcggataa agttgcagga ccacttctgc gctcggccct tccggctggc tggtttattg   5880

ctgataaatc tggagccggt gagcgtgggt ctcgcggtat cattgcagca ctggggccag   5940

atggtaagcc ctcccgtatc gtagttatct acacgacggg gagtcaggca actatggatg   6000

aacgaaatag acagatcgct gagataggtg cctcactgat taagcattgg taactgtcag   6060

accaagttta ctcatatata ctttagattg atttaaaact tcatttttaa tttaaaagga   6120

tctaggtgaa gatccttttt gataatctca tgaccaaaat cccttaacgt gagttttcgt   6180

tccactgagc gtcagacccc gtagaaaaga tcaaaggatc ttcttgagat cctttttttc   6240

tgcgcgtaat ctgctgcttg caaacaaaaa aaccaccgct accagcggtg gtttgtttgc   6300

cggatcaaga gctaccaact ctttttccga aggtaactgg cttcagcaga gcgcagatac   6360

caaatactgt ccttctagtg tagccgtagt taggccacca cttcaagaac tctgtagcac   6420

cgcctacata cctcgctctg ctaatcctgt taccagtggc tgctgccagt ggcgataagt   6480

cgtgtcttac cgggttggac tcaagacgat agttaccgga taaggcgcag cggtcgggct   6540

gaacgggggg ttcgtgcaca cagcccagct tggagcgaac gacctacacc gaactgagat   6600

acctacagcg tgagctatga gaaagcgcca cgcttcccga agggagaaag gcggacaggt   6660

atccggtaag cggcagggtc ggaacaggag agcgcacgag ggagcttcca gggggaaacg   6720

cctggtatct ttatagtcct gtcgggtttc gccacctctg acttgagcgt cgatttttgt   6780

gatgctcgtc aggggggcgg agcctatgga aaaacgccag caacgcggcc tttttacggt   6840

tcctggcctt ttgctggcct tttgctcaca tgttctttcc tgcgttatcc cctgattctg   6900

tggataaccg tattaccgcc tttgagtgag ctgataccgc tcgccgcagc cgaacgaccg   6960

agcgcagcga gtcagtgagc gaggaagcgg aaga                                6994
```

<210> SEQ ID NO 17
<211> LENGTH: 6764
<212> TYPE: DNA
<213> ORGANISM: Artificial Sequence
<220> FEATURE:
<223> OTHER INFORMATION: Designed plasmid DNA, pUC-pBAD-CrtI-m2-CrtY-
      CrtZBD

<400> SEQUENCE: 17

-continued

```
gcgcccaata cgcaaaccgc ctctccccgc gcgttggccg attcattaat gcagctggca     60
cgacaggttt cccgactgga aagcgccatg gttatgacaa cttgacggct acatcattca    120
ctttttcttc acaaccggca cggaactcgc tcgggctggc cccggtgcat tttttaaata    180
cccgcgagaa atagagttga tcgtcaaaac caacattgcg accgacggtg gcgataggca    240
tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
ccccttgccc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgatttttc accacccccct gaccgcgaat ggtgagattg agaatataac    840
ctttcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat acttttcata ctcccgccat tcagagaaga aaccaattgt ccatattgca   1020
tcagacattg ccgtcactgc gtcttttact ggctcttctc gctaaccaaa ccggtaaccc   1080
cgcttattaa aagcattctg taacaaagcg ggaccaaagc catgacaaaa acgcgtaaca   1140
aaagtgtcta taatcacggc agaaaagtcc acattgatta tttgcacggc gtcacacttt   1200
gctatgccat agcattttta tccataagat tagcggatcc tacctgacgc tttttatcgc   1260
aactctctac tgtttctcca tacccgtttg aattctctag actcgagagg aggattacaa   1320
aatgaaacca actacggtaa ttggtgcagg cttcggtggc ctggcactgg caattcgtct   1380
acaagctgcg gggatccccg tcttactgct tgaacaacgt gataaacccg gcggtcgggc   1440
ttatgtctac gaggatcagg ggtttacctt tgatgcaggc ccgacggtta tcaccgatcc   1500
cagtgccatt gaagaactgt ttgcactggc aggaaaacag ttaaaagagt atgtcgaact   1560
gctgccggtt acgccgtttt accgcctgtg ttgggagtca gggaaggtct ttaattacga   1620
taacgatcaa acccggctcg aagcgcagat tcagcagttt aatccccgcg atgtcgaagg   1680
ttatcgtcag tttctggact attcacgcgc ggtgtttaaa gaaggctatc taaagctcgg   1740
tactgtccct tttttatcgt tcagagacat gcttcgcgcc gcacctcaac tggcgaaact   1800
gcaggcatgg agaagcgttt acagtaaggt tgccagttac atcgaagatg aacatctgcg   1860
ccaggcgttt tctttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt agctctctgt ttgtgctcta ttttggtttg aatcaccatc atgatcagct   2280
cgcgcatcac acggtttgtt tcggcccgcg ttaccgcgag ctgattgacg aaatttttaa   2340
```

-continued

```
tcatgatggc ctcgcagagg acttctcact ttatctgcac gcgccctgtg tcacggattc   2400

gtcactggcg cctgaaggtt gcggcagtta ctatgtgttg gcgccggtgc cacatttagg   2460

caccgcgaac ctcgactgga cggttgaggg gccaaaacta cgcgaccgta tttttgcgta   2520

ccttgagcag cattacatgc ctggcttacg gagtcagctg gtcacgcacc ggatgtttac   2580

gccgtttgat tttcgcgacc agcttaatgc ctatcatggc tcagcctttt ctgtggagcc   2640

cgttcttacc cagagcgcct ggtttcggcc gcataaccgc gataaaacca ttactaatct   2700

ctacctggtc ggcgcaggca cgcatcccgg cgcaggcatt cctggcgtca tcggctcggc   2760

aaaagcgaca gcaggtttga tgctggagga tctgatttga gggcccgtgt aggaggatta   2820

caaaatgcaa ccgcattatg atctgattct cgtgggggct ggactcgcga atggccttat   2880

cgccctgcgt cttcagcagc agcaacctga tatgcgtatt ttgcttatcg acgccgcacc   2940

ccaggcgggc gggaatcata cgtggtcatt tcaccacgat gatttgactg agagccaaca   3000

tcgttggata gctccgctgg tggttcatca ctggcccgac tatcaggtac gctttcccac   3060

acgccgtcgt aagctgaaca gcggctactt ttgtattact tctcagcgtt tcgctgaggt   3120

tttacagcga cagtttggcc cgcacttgtg gatggatacc gcggtcgcag aggttaatgc   3180

ggaatctgtt cggttgaaaa agggtcaggt tatcggtgcc cgcgcggtga ttgacgggcg   3240

gggttatgcg gcaaattcag cactgagcgt gggcttccag gcgtttattg gccaggaatg   3300

gcgattgagc cacccgcatg gtttatcgtc tcccattatc atggatgcca cggtcgatca   3360

gcaaaatggt tatcgcttcg tgtacagcct gccgctctcg ccgaccagat tgttaattga   3420

agacacgcac tatattgata atgcgacatt agatcctgaa tgcgcgcggc aaaatatttg   3480

cgactatgcc gcgcaacagg gttggcagct tcagacactg ctgcgagaag aacagggcgc   3540

cttacccatt actctgtcgg gcaatgccga cgcattctgg cagcagcgcc ccctggcctg   3600

tagtggatta cgtgccggtc tgttccatcc taccaccggc tattcactgc cgctggcggt   3660

tgccgtggcc gaccgcctga gtgcacttga tgtctttacg tcggcctcaa ttcaccatgc   3720

cattacgcat tttgcccgcg agcgctggca gcagcagggc tttttccgca tgctgaatcg   3780

catgctgttt ttagccggac ccgccgattc acgctggcgg gttatgcagc gtttttatgg   3840

tttacctgaa gatttaattg cccgttttta tgcgggaaaa ctcacgctga ccgatcggct   3900

acgtattctg agcggcaagc cgcctgttcc ggtattagca gcattgcaag ccattatgac   3960

gactcatcgt taaactagat aactagcgat tcactgtata acattaagaa ggaggattac   4020

aaaatggcat ggctgacctg gatcgcactg ttcctgaccg cattcctggg tatggaggct   4080

ttcgcgtgga tcatgcaccg ttatgtcatg cacggtttct tgtggtcgtg gcatcgtagc   4140

catcacgagc cgcacgacca cccgctggaa aagaacgacc tgtttgccgt tgtctttgcc   4200

gctccggcga ttgttatggt ggcggtgggt ctgcacctgt ggccttgggc cttgccggtc   4260

ggtctgggta ttactgcgta cggcatggtt tacttcttct ttcatgatgg cctggtgcat   4320

cgtcgtttcc cgacgggctt tagcggtcgc agcggctttt ggacccgtcg catccaggcg   4380

caccgtctgc accatgcagt ccgcacgcgt gagggctgcg tgtcctttgg cttcttgtgg   4440

gttcgcagcg cgcgtgccct gaaagcggaa ctggcgcaaa aacgcggtag cagcagctct   4500

ggtgcataaa agctttatct agttgctgat gcggtatttt ctccttacgc atctgtgcgg   4560

tatttcacac cgcatatatg gtgcactctc agtacaatct gctctgatgc cgcatagtta   4620

agccagcccc gacacccgcc aacacccgct gacgcgccct gacgggcttg tctgctcccg   4680

gcatccgctt acagacaagc tgtgaccgtc tccgggagct gcatgtgtca gaggttttca   4740
```

-continued ccgtcatcac cgaaacgcgc gagacgaaag ggcctcgtga tacgcctatt tttataggtt 4800
aatgtcatga taataatggt ttcttagacg tcaggtggca cttttcgggg aaatgtgcgc 4860
ggaaccccta tttgtttatt tttctaaata cattcaaata tgtatccgct catgagacaa 4920
taaccctgat aaatgcttca ataatattga aaaaggaaga gtatgagtat tcaacatttc 4980
cgtgtcgccc ttattccctt ttttgcggca ttttgccttc ctgtttttgc tcacccagaa 5040
acgctggtga aagtaaaaga tgctgaagat cagttgggtg cacgagtggg ttacatcgaa 5100
ctggatctca acagcggtaa gatccttgag agttttcgcc ccgaagaacg ttttccaatg 5160
atgagcactt ttaaagttct gctatgtggc gcggtattat cccgtattga cgccgggcaa 5220
gagcaactcg gtcgccgcat acactattct cagaatgact tggttgagta ctcaccagtc 5280
acagaaaagc atcttacgga tggcatgaca gtaagagaat tatgcagtgc tgccataacc 5340
atgagtgata acactgcggc caacttactt ctgacaacga tcggaggacc gaaggagcta 5400
accgcttttt tgcacaacat gggggatcat gtaactcgcc ttgatcgttg ggaaccggag 5460
ctgaatgaag ccataccaaa cgacgagcgt gacaccacga tgcctgtagc aatggcaaca 5520
acgttgcgca aactattaac tggcgaacta cttactctag cttcccggca acaattaata 5580
gactggatgg aggcggataa agttgcagga ccacttctgc gctcggccct tccggctggc 5640
tggtttattg ctgataaatc tggagccggt gagcgtgggt ctcgcggtat cattgcagca 5700
ctggggccag atggtaagcc ctcccgtatc gtagttatct acacgacggg gagtcaggca 5760
actatggatg aacgaaatag acagatcgct gagataggtg cctcactgat taagcattgg 5820
taactgtcag accaagttta ctcatatata ctttagattg atttaaaact tcatttttaa 5880
tttaaaagga tctaggtgaa gatccttttt gataatctca tgaccaaaat cccttaacgt 5940
gagttttcgt tccactgagc gtcagacccc gtagaaaaga tcaaaggatc ttcttgagat 6000
cctttttttc tgcgcgtaat ctgctgcttg caaacaaaaa aaccaccgct accagcggtg 6060
gtttgtttgc cggatcaaga gctaccaact ctttttccga aggtaactgg cttcagcaga 6120
gcgcagatac caaatactgt ccttctagtg tagccgtagt taggccacca cttcaagaac 6180
tctgtagcac cgcctacata cctcgctctg ctaatcctgt taccagtggc tgctgccagt 6240
ggcgataagt cgtgtcttac cgggttggac tcaagacgat agttaccgga taaggcgcag 6300
cggtcgggct gaacgggggg ttcgtgcaca cagcccagct tggagcgaac gacctacacc 6360
gaactgagat acctacagcg tgagctatga gaaagcgcca cgcttcccga agggagaaag 6420
gcggacaggt atccggtaag cggcagggtc ggaacaggag agcgcacgag ggagcttcca 6480
gggggaaacg cctggtatct ttatagtcct gtcgggtttc gccacctctg acttgagcgt 6540
cgatttttgt gatgctcgtc aggggggcgg agcctatgga aaaacgccag caacgcggcc 6600
tttttacggt tcctggcctt ttgctggcct tttgctcaca tgttctttcc tgcgttatcc 6660
cctgattctg tggataaccg tattaccgcc tttgagtgag ctgataccgc tcgccgcagc 6720
cgaacgaccg agcgcagcga gtcagtgagc gaggaagcgg aaga 6764

<210> SEQ ID NO 18
<211> LENGTH: 7516
<212> TYPE: DNA
<213> ORGANISM: Artificial Sequence
<220> FEATURE:
<223> OTHER INFORMATION: Designed plasmid DNA, pUC-pBAD-CrtI-m2-CrtY-CrtWBD-CrtZBD

<400> SEQUENCE: 18

-continued

```
gcgcccaata cgcaaaccgc ctctccccgc gcgttggccg attcattaat gcagctggca     60
cgacaggttt cccgactgga aagcgccatg gttatgacaa cttgacggct acatcattca    120
ctttttcttc acaaccggca cggaactcgc tcgggctggc cccggtgcat tttttaaata    180
cccgcgagaa atagagttga tcgtcaaaac caacattgcg accgacggtg gcgataggca    240
tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
ccccttgccc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgatttttc accacccccct gaccgcgaat ggtgagattg agaatataac    840
ctttcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat acttttcata ctcccgccat tcagagaaga aaccaattgt ccatattgca   1020
tcagacattg ccgtcactgc gtcttttact ggctcttctc gctaaccaaa ccggtaaccc   1080
cgcttattaa aagcattctg taacaaagcg ggaccaaagc catgacaaaa acgcgtaaca   1140
aaagtgtcta taatcacggc agaaaagtcc acattgatta tttgcacggc gtcacacttt   1200
gctatgccat agcattttta tccataagat tagcggatcc tacctgacgc tttttatcgc   1260
aactctctac tgtttctcca tacccgtttg aattctctag actcgagagg aggattacaa   1320
aatgaaacca actacggtaa ttggtgcagg cttcggtggc ctggcactgg caattcgtct   1380
acaagctgcg gggatccccg tcttactgct tgaacaacgt gataaacccg gcggtcgggc   1440
ttatgtctac gaggatcagg ggtttacctt tgatgcaggc ccgacggtta tcaccgatcc   1500
cagtgccatt gaagaactgt ttgcactggc aggaaaacag ttaaaagagt atgtcgaact   1560
gctgccggtt acgccgtttt accgcctgtg ttgggagtca gggaaggtct ttaattacga   1620
taacgatcaa acccggctcg aagcgcagat tcagcagttt aatccccgcg atgtcgaagg   1680
ttatcgtcag tttctggact attcacgcgc ggtgtttaaa gaaggctatc taaagctcgg   1740
tactgtccct tttttatcgt tcagagacat gcttcgcgcc gcacctcaac tggcgaaact   1800
gcaggcatgg agaagcgttt acagtaaggt tgccagttac atcgaagatg aacatctgcg   1860
ccaggcgttt tctttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt agctctctgt ttgtgctcta ttttggtttg aatcaccatc atgatcagct   2280
cgcgcatcac acggtttgtt tcggcccgcg ttaccgcgag ctgattgacg aaatttttaa   2340
```

-continued

```
tcatgatggc ctcgcagagg acttctcact ttatctgcac gcgccctgtg tcacggattc   2400
gtcactggcg cctgaaggtt gcggcagtta ctatgtgttg gcgccggtgc cacatttagg   2460
caccgcgaac ctcgactgga cggttgaggg gccaaaacta cgcgaccgta tttttgcgta   2520
ccttgagcag cattacatgc ctggcttacg gagtcagctg gtcacgcacc ggatgtttac   2580
gccgtttgat tttcgcgacc agcttaatgc ctatcatggc tcagcctttt ctgtggagcc   2640
cgttcttacc cagagcgcct ggtttcggcc gcataaccgc gataaaacca ttactaatct   2700
ctacctggtc ggcgcaggca cgcatcccgg cgcaggcatt cctggcgtca tcggctcggc   2760
aaaagcgaca gcaggtttga tgctggagga tctgatttga gggcccgtgt aggaggatta   2820
caaaatgcaa ccgcattatg atctgattct cgtgggggct ggactcgcga atggccttat   2880
cgccctgcgt cttcagcagc agcaacctga tatgcgtatt ttgcttatcg acgccgcacc   2940
ccaggcgggc gggaatcata cgtggtcatt tcaccacgat gatttgactg agagccaaca   3000
tcgttggata gctccgctgg tggttcatca ctggcccgac tatcaggtac gctttcccac   3060
acgccgtcgt aagctgaaca gcggctactt ttgtattact tctcagcgtt tcgctgaggt   3120
tttacagcga cagtttggcc cgcacttgtg gatggatacc gcggtcgcag aggttaatgc   3180
ggaatctgtt cggttgaaaa agggtcaggt tatcggtgcc cgcgcggtga ttgacgggcg   3240
gggttatgcg gcaaattcag cactgagcgt gggcttccag gcgtttattg gccaggaatg   3300
gcgattgagc cacccgcatg gtttatcgtc tcccattatc atggatgcca cggtcgatca   3360
gcaaaatggt tatcgcttcg tgtacagcct gccgctctcg ccgaccagat tgttaattga   3420
agacacgcac tatattgata atgcgacatt agatcctgaa tgcgcgcggc aaaatatttg   3480
cgactatgcc gcgcaacagg gttggcagct tcagacactg ctgcgagaag aacagggcgc   3540
cttacccatt actctgtcgg gcaatgccga cgcattctgg cagcagcgcc ccctggcctg   3600
tagtggatta cgtgccggtc tgttccatcc taccaccggc tattcactgc cgctggcggt   3660
tgccgtggcc gaccgcctga gtgcacttga tgtctttacg tcggcctcaa ttcaccatgc   3720
cattacgcat tttgcccgcg agcgctggca gcagcagggc tttttccgca tgctgaatcg   3780
catgctgttt ttagccggac ccgccgattc acgctggcgg gttatgcagc gtttttatgg   3840
tttacctgaa gatttaattg cccgttttta tgcgggaaaa ctcacgctga ccgatcggct   3900
acgtattctg agcggcaagc cgcctgttcc ggtattagca gcattgcaag ccattatgac   3960
gactcatcgt taaactagat aactagtagg aggattacaa aatgaccgca gctgtcgcag   4020
aacctcgcat tgtaccgcgc caaacctgga tcggcctgac cctggcgggt atgattgtgg   4080
cgggctgggg ttctctgcac gtgtacggtg tgtacttcca ccgttggggc accagcagcc   4140
tggttatcgt cccggctatc gtggccgttc agacgtggtt gtcggttggc ctgtttattg   4200
tcgcacatga cgccatgcac ggttccctgg ccccaggccg tccgcgcctg aacgcagcgg   4260
tgggtcgtct gacgctgggt ctgtatgcag gcttccgttt cgatcgcttg aaaacggcgc   4320
accacgcgca tcatgcggct ccgggtaccg cagatgaccc ggacttttac gcgcctgcgc   4380
cacgcgcctt cctgccgtgg tttttgaact tttccgtac ctatttcggt tggcgcgaga   4440
tggcggttct gaccgcgctg gtcctgatcg cgctgtttgg cttgggtgcc cgtccggcga   4500
atctgttgac tttttgggcc gcaccggcgc tgctgagcgc gctgcaactg ttcacgtttg   4560
gcacctggct gccgcaccgt cacacggacc agccgttcgc ggatgctcat catgcacgca   4620
gcagcggtta tggtccggtt ctgagcctgc tgacctgctt tcatttcggt cgtcatcacg   4680
agcaccacct gacgccgtgg cgtccgtggt ggcgtttgtg gcgtggtgaa agctaaatcg   4740
```

-continued

```
attcactgta taacattaag aaggaggatt acaaaatggc atggctgacc tggatcgcac   4800
tgttcctgac cgcattcctg ggtatggagg ctttcgcgtg gatcatgcac cgttatgtca   4860
tgcacggttt cttgtggtcg tggcatcgta gccatcacga gccgcacgac cacccgctgg   4920
aaaagaacga cctgtttgcc gttgtctttg ccgctccggc gattgttatg gtggcggtgg   4980
gtctgcacct gtggccttgg gccttgccgg tcggtctggg tattactgcg tacggcatgg   5040
tttacttctt ctttcatgat ggcctggtgc atcgtcgttt cccgacgggc tttagcggtc   5100
gcagcggctt ttggacccgt cgcatccagg cgcaccgtct gcaccatgca gtccgcacgc   5160
gtgagggctg cgtgtccttt ggcttcttgt gggttcgcag cgcgcgtgcc ctgaaagcgg   5220
aactggcgca aaaacgcggt agcagcagct ctggtgcata aaagctttat ctagttgctg   5280
atgcggtatt ttctccttac gcatctgtgc ggtatttcac accgcatata tggtgcactc   5340
tcagtacaat ctgctctgat gccgcatagt taagccagcc ccgacacccg ccaacacccg   5400
ctgacgcgcc ctgacgggct tgtctgctcc cggcatccgc ttacagacaa gctgtgaccg   5460
tctccgggag ctgcatgtgt cagaggtttt caccgtcatc accgaaacgc gcgagacgaa   5520
agggcctcgt gatacgccta tttttatagg ttaatgtcat gataataatg gtttcttaga   5580
cgtcaggtgg cacttttcgg ggaaatgtgc gcggaacccc tatttgttta tttttctaaa   5640
tacattcaaa tatgtatccg ctcatgagac aataaccctg ataaatgctt caataatatt   5700
gaaaaaggaa gagtatgagt attcaacatt tccgtgtcgc ccttattccc ttttttgcgg   5760
cattttgcct tcctgttttt gctcacccag aaacgctggt gaaagtaaaa gatgctgaag   5820
atcagttggg tgcacgagtg ggttacatcg aactggatct caacagcggt aagatccttg   5880
agagttttcg ccccgaagaa cgttttccaa tgatgagcac ttttaaagtt ctgctatgtg   5940
gcgcggtatt atcccgtatt gacgccgggc aagagcaact cggtcgccgc atacactatt   6000
ctcagaatga cttggttgag tactcaccag tcacagaaaa gcatcttacg gatggcatga   6060
cagtaagaga attatgcagt gctgccataa ccatgagtga taacactgcg gccaacttac   6120
ttctgacaac gatcggagga ccgaaggagc taaccgcttt tttgcacaac atgggggatc   6180
atgtaactcg ccttgatcgt tgggaaccgg agctgaatga agccatacca aacgacgagc   6240
gtgacaccac gatgcctgta gcaatggcaa caacgttgcg caaactatta actggcgaac   6300
tacttactct agcttcccgg caacaattaa tagactggat ggaggcggat aaagttgcag   6360
gaccacttct gcgctcggcc cttccggctg gctggtttat tgctgataaa tctggagccg   6420
gtgagcgtgg gtctcgcggt atcattgcag cactggggcc agatggtaag ccctcccgta   6480
tcgtagttat ctacacgacg gggagtcagg caactatgga tgaacgaaat agacagatcg   6540
ctgagatagg tgcctcactg attaagcatt ggtaactgtc agaccaagtt tactcatata   6600
tactttagat tgatttaaaa cttcattttt aatttaaaag gatctaggtg aagatccttt   6660
ttgataatct catgaccaaa atcccttaac gtgagttttc gttccactga gcgtcagacc   6720
ccgtagaaaa gatcaaagga tcttcttgag atcctttttt tctgcgcgta atctgctgct   6780
tgcaaacaaa aaaaccaccg ctaccagcgg tggtttgttt gccggatcaa gagctaccaa   6840
ctctttttcc gaaggtaact ggcttcagca gagcgcagat accaaatact gtccttctag   6900
tgtagccgta gttaggccac cacttcaaga actctgtagc accgcctaca tacctcgctc   6960
tgctaatcct gttaccagtg gctgctgcca gtggcgataa gtcgtgtctt accgggttgg   7020
actcaagacg atagttaccg gataaggcgc agcggtcggg ctgaacgggg ggttcgtgca   7080
```

```
cacagcccag cttggagcga acgacctaca ccgaactgag atacctacag cgtgagctat   7140

gagaaagcgc cacgcttccc gaagggagaa aggcggacag gtatccggta agcggcaggg   7200

tcggaacagg agagcgcacg agggagcttc caggggggaaa cgcctggtat ctttatagtc   7260

ctgtcgggtt tcgccacctc tgacttgagc gtcgattttt gtgatgctcg tcaggggggc   7320

ggagcctatg gaaaaacgcc agcaacgcgg cctttttacg gttcctggcc ttttgctggc   7380

cttttgctca catgttcttt cctgcgttat cccctgattc tgtggataac cgtattaccg   7440

cctttgagtg agctgatacc gctcgccgca gccgaacgac cgagcgcagc gagtcagtga   7500

gcgaggaagc ggaaga                                                  7516
```

<210> SEQ ID NO 19
<211> LENGTH: 7359
<212> TYPE: DNA
<213> ORGANISM: Artificial Sequence
<220> FEATURE:
<223> OTHER INFORMATION: Designed plasmid DNA, pAC-crtMF26A,W38A,F233S-fdsY81A,V157A-idi

<400> SEQUENCE: 19

```
gaattccgga tgagcattca tcaggcgggc aagaatgtga ataaaggccg gataaaactt     60

gtgcttattt ttctttacgg tctttaaaaa ggccgtaata tccagctgaa cggtctggtt    120

ataggtacat tgagcaactg actgaaatgc ctcaaaatgt tctttacgat gccattggga    180

tatatcaacg gtggtatatc cagtgatttt tttctccatt ttagcttcct tagctcctga    240

aaatctcgat aactcaaaaa atacgcccgg tagtgatctt atttcattat ggtgaaagtt    300

ggaacctctt acgtgccgat caacgtctca ttttcgccaa aagttggccc agggcttccc    360

ggtatcaaca gggacaccag gatttattta ttctgcgaag tgatcttccg tcacaggtat    420

ttattcggcg caaagtgcgt cgggtgatgc tgccaactta ctgatttagt gtatgatggt    480

gtttttgagg tgctccagtg gcttctgttt ctatcagctg tccctcctgt tcagctactg    540

acggggtggt gcgtaacggc aaaagcaccg ccggacatca gcgctagcgg agtgtatact    600

ggcttactat gttggcactg atgagggtgt cagtgaagtg cttcatgtgg caggagaaaa    660

aaggctgcac cggtgcgtca gcagaatatg tgatacagga tatattccgc ttcctcgctc    720

actgactcgc tacgctcggt cgttcgactg cggcgagcgg aaatggctta cgaacggggc    780

ggagatttcc tggaagatgc caggaagata cttaacaggg aagtgagagg gccgcggcaa    840

agccgttttt ccataggctc cgcccccctg acaagcatca cgaaatctga cgctcaaatc    900

agtggtggcg aaacccgaca ggactataaa gataccaggc gtttccccctg gcggctccct    960

cgtgcgctct cctgttcctg cctttcggtt taccggtgtc attccgctgt tatggccgcg   1020

tttgtctcat tccacgcctg acactcagtt ccgggtaggc agttcgctcc aagctggact   1080

gtatgcacga acccccccgtt cagtccgacc gctgcgcctt atccggtaac tatcgtcttg   1140

agtccaaccc ggaaagacat gcaaaagcac cactggcagc agccactggt aattgattta   1200

gaggagttag tcttgaagtc atgcgccggt taaggctaaa ctgaaaggac aagttttggt   1260

gactgcgctc ctccaagcca gttacctcgg ttcaaagagt tggtagctca gagaaccttc   1320

gaaaaaccgc cctgcaaggc ggtttttttcg ttttcagagc aagagattac gcgcagacca   1380

aaacgatctc aagaagatca tcttattaat cagataaaat atttcaagat ttcagtgcaa   1440

tttatctctt caaatgtagc acctgaagtc agccccatac gatataagtt gtaattctca   1500

tgtttgacag cttatcgtga ggtttcccga ctggaaagcg ggcagtgagc gcaacgcaat   1560
```

-continued

```
taatgtgagt tagctcactc attaggcacc ccaggcttta cactttatgc ttccggctcg   1620
tatgttgtgt ggaattgtga gcggataaca atttcacaca ggaaacacat atggaattct   1680
ctagaaggag gagtaagcga tggcgcagct ttcagttgaa cagtttctca acgagcaaaa   1740
acaggcggtg gaaacagcgc tctcccgtta tatagagcgc ttagaagggc cggcgaagct   1800
gaaaaaggcg atggcgtact cattggaggc cggcggcaaa cgaatccgtc cgttgctgct   1860
tctgtccacc gttcgggcgc tcggcaaaga cccggcggtc ggattgcccg tcgcctgcgc   1920
gattgaaatg atccatacgg catctttgat ccatgatgat ttgccgagca tggacaacga   1980
tgatttgcgg cgcggcaagc cgacgaacca taaagtgttc ggcgaggcga tggccatctt   2040
ggcgggggac gggttgttga cgtacgcgtt tcaattgatc accgaaatcg acgatgagcg   2100
catccctcct tccgtccggc ttcggctcat cgaacggctg gcgaaagcgg ccggtccgga   2160
agggatggcg gccggtcagg cagccgatat ggaaggagag gggaaaacgc tgacgctttc   2220
ggagctcgaa tacattcatc ggcataaaac cgggaaaatg ctgcaataca gcgtgcacgc   2280
cggcgccttg atcggcggcg ctgatgcccg gcaaacgcgg gagcttgacg aattcgccgc   2340
ccatctaggc cttgcctttc aaattcgcga tgatattctc gatattgaag gggcagaaga   2400
aaaaatcggc aagccggtcg gcagcgacca aagcaacaac aaagcgacgt atccagcgtt   2460
gctgtcgctt gccggcgcga aggaaaagtt ggcgttccat atcgaggcgg cgcagcgcca   2520
tttacggaac gctgacgttg acggcgccgc gctcgcctat atttgcgaac tggtcgccgc   2580
ccgcgaccat taactcgagg ggcccggcgc ctgatgcggt attttctcct tacgcatctg   2640
tgcggtattt cactgcatcg ataagcttta atgcggtagt ttatcacagt taaattgcta   2700
acgcagtcag gcaccgtgta tgaaatctaa caatgcgctc atcgtcatcc tcggcaccgt   2760
caccctggat gctgtaggca taggcttggt tatgccggta ctgccgggcc tcttgcggga   2820
tatcgtccat tccgacagca tcgccagtca ctatggcgtg ctgctagcgc tatatgcgtt   2880
gatgcaattt ctatgcgcac ccgttctcgg agcactgtcc gaccgctttg gccgccgccc   2940
agtcctgctc gcttcgctac ttggagccac tatcgactac gcgatcatgg cgaccacacc   3000
cgtcctgtgg atcccgtgga ggtttcccga ctggaaagcg ggcagtgagc gcaacgcaat   3060
taatgtgagt tagctcactc attaggcacc ccaggcttta cactttatgc ttccggctcg   3120
tatgttgtgt ggaattgtga gcggataaca atttcacaca ggaaacacat atggaattct   3180
ctagaaggag gattacaaaa tgacaatgat gaatatgaat tttaaatatt gtcataaaat   3240
catgaagaaa cattcaaaaa gcttttctta cgctgcggac ttgttaccag aagatcaaag   3300
aaaagcggtt gcggcaattt atgctgtgtg tcgtaaaatt gatgacagta tagatgttta   3360
tggcgatatt caatttttaa atcaaataaa agaagatata caatctattg aaaaataccc   3420
atatgaacat catcactttc aaagtgatcg tagaatcatg atggcgcttc agcatgttgc   3480
acaacataaa aatatcgcct ttcaatcttt ttataatctc attgatactg tatataaaga   3540
tcaacatttt acaatgtttg aaacggacgc tgaattattc ggatattgtt atggtgttgc   3600
tggtacagta ggtgaagtat tgacgccgat tttaagtgat catgaaacac atcagacata   3660
cgatgtcgca agaagacttg gtgaatcgtt gcaattgatt aatatattaa gagatgtcgg   3720
tgaagatttt gacaatgaac ggatatattt tagtaagcaa cgattaaagc aatatgaagt   3780
tgatattgct gaagtgtacc aaaatggtgt taataatcat tatattgact tatgggaata   3840
ttatgcagct atcgcagaaa aagattttca agatgttatg gatcaaatca aagtatctag   3900
tattgaagca caaccaatca tagaattagc agcacgtata tatattgaaa tactggacga   3960
```

agtgagacag gctaactata cattacatga acgtgttttt gtggataaga ggaaaaaggc 4020
aaagttgttt catgaaataa atagtaaata tcatagaata tagctcgagg ggcccggcgc 4080
ctgatgcggt attttctcct tacgcatctg tgcggtattt cacgtgcgct cgaggggccc 4140
ggcgcctgat gcggtatttt ctccttacgc atctgtgcgg tatttcacgg atcctctacg 4200
ccggacgcat cgtggccggc atcaccggcg ccacaggtgc ggttgctggc gcctatatcg 4260
ccgacatcac cgatggggaa gatcgggctc gccacttcgg gctcatgagc gcttgtttcg 4320
gcgtgggtat ggtggcaggc cccgtggccg ggggactgtt gggcgccatc tccttgcatg 4380
caccattcct tgcggcggcg gtgctcaacg gcctcaacct actactgggc tgcttcctaa 4440
tgcaggagtc gcataaggga gagcgtcgac gtgaaatacc gcacagatgc gtaaggagaa 4500
aataccgcat caggcgccgg gcccctcgag ttatttaagc tgggtaaatg cagataatcg 4560
ttttctggct tcgcgatttg tcgcctgcat caccatccac ggactgaacg cccacggcgt 4620
ggcatcaata ccgtgtaata catctgctaa atcacaccat tgataatcca tcacttcatc 4680
atcattgatc tgtaacgcac tagtggtgcg tgcggcaaat accggacaca cttcattttc 4740
cacaatgcca ctcggatcgg tggcgcggta gcgaaagtca ggatagatag attcaggagg 4800
cgtaatttcc acgccaagct cataacggca acggcggatc actgcgtctt cgttgctttc 4860
tcccagttgt gggtgcccac aaaccgagtt agtccacacg ccaggccatg ctttttgct 4920
cagtgcgcgg cgggtaacta ataattgtcc tttggcatta aacagccaac tggagaacgc 4980
gagatgtaag cgggtgtctg ccgtgtgtgc ggcatacttt tccagcgtac ccgtgggaac 5040
tccctgtgca ttcaataaaa tgacgtgttc cgtttgcatt ttgtaatcct ccttctagag 5100
aattccatat gtgtttcctg tgtgaaattg ttatccgctc acaattccac acaacatacg 5160
agccggaagc ataaagtgta aagcctgggg tgcctaatga gtgagctaac tcacattaat 5220
tgcgttgcgc tcactgcccg ctttccagtc gggaaacctg tcgaccgatg cccttgagag 5280
ccttcaaccc agtcagctcc ttccggtggg cgcggggcat gactatcgtc gccgcactta 5340
tgactgtctt ctttatcatg caactcgtag gacaggtgcc ggcagcgctc tgggtcattt 5400
tcggcgagga ccgctttcgc tggagcgcga cgatgatcgg cctgtcgctt gcggtattcg 5460
gaatcttgca cgccctcgct caagccttcg tcactggtcc cgccaccaaa cgtttcggcg 5520
agaagcaggc cattatcgcc ggcatggcgg ccgacgcgct gggctacgtc ttgctggcgt 5580
tcgcgacgcg aggctggatg gccttcccca ttatgattct tctcgcttcc ggcggcatcg 5640
ggatgcccgc gttgcaggcc atgctgtcca ggcaggtaga tgacgaccat cagggacagc 5700
ttcaaggatc gctcgcggct cttaccagcc taacttcgat cactggaccg ctgatcgtca 5760
cggcgattta tgccgcctcg gcgagcacat ggaacgggtt ggcatggatt gtaggcgccg 5820
ccctatacct tgtctgcctc cccgcgttgc gtcgcggtgc atggagccgg gccacctcga 5880
cctgaatgga agccggcggc acctcgctaa cggattcacc actccaagaa ttggagccaa 5940
tcaattcttg cggagaactg tgaatgcgca aaccaaccct tggcagaaca tatccatcgc 6000
gtccgccatc tccagcagcc gcacgcggcg catctcgggc agcgttgggt cctggccacg 6060
ggtgcgcatg atcgtgctcc tgtcgttgag gacccggcta ggctggcggg gttgccttac 6120
tggttagcag aatgaatcac cgatacgcga gcgaacgtga agcgactgct gctgcaaaac 6180
gtctgcgacc tgagcaacaa catgaatggt cttcggtttc cgtgtttcgt aaagtctgga 6240
aacgcggaag tcccctacgt gctgctgaag ttgcccgcaa cagagagtgg aaccaaccgg 6300

-continued

```
tgataccacg atactatgac tgagagtcaa cgccatgagc ggcctcattt cttattctga   6360

gttacaacag tccgcaccgc tgtccggtag ctccttccgg tgggcgcggg gcatgactat   6420

cgtcgccgca cttatgactg tcttctttat catgcaactc gtaggacagg tgccggcagc   6480

gcccaacagt cccccggcca cggggcctgc caccataccc acgccgaaac aagcgccctg   6540

caccattatg ttccggatct gcatcgcagg atgctgctgg ctaccctgtg gaacacctac   6600

atctgtatta acgaagcgct aaccgttttt atcaggctct gggaggcaga ataaatgatc   6660

atatcgtcaa ttattacctc cacggggaga gcctgagcaa actggcctca ggcatttgag   6720

aagcacacgg tcacactgct tccggtagtc aataaaccgg taaaccagca atagacataa   6780

gcggctattt aacgaccctg ccctgaaccg acgaccgggt cgaatttgct ttcgaatttc   6840

tgccattcat ccgcttatta tcacttattc aggcgtagca ccaggcgttt aagggcacca   6900

ataactgcct taaaaaaatt acgccccgcc ctgccactca tcgcagtact gttgtaattc   6960

attaagcatt ctgccgacat ggaagccatc acagacggca tgatgaacct gaatcgccag   7020

cggcatcagc accttgtcgc cttgcgtata atatttgccc atggtgaaaa cgggggcgaa   7080

gaagttgtcc atattggcca cgtttaaatc aaaactggtg aaactcaccc agggattggc   7140

tgagacgaaa aacatattct caataaaccc tttagggaaa taggccaggt tttcaccgta   7200

acacgccaca tcttgcgaat atatgtgtag aaactgccgg aaatcgtcgt ggtattcact   7260

ccagagcgat gaaaacgttt cagtttgctc atggaaaacg gtgtaacaag ggtgaacact   7320

atcccatatc accagctcac cgtctttcat tgccatacg                           7359


<210> SEQ ID NO 20
<211> LENGTH: 7561
<212> TYPE: DNA
<213> ORGANISM: Artificial
<220> FEATURE:
<223> OTHER INFORMATION: Designed plasmid DNA, pUC-pBAD-CrtIN304P-CrtY-
      CrtG-CrtZBD

<400> SEQUENCE: 20

gcgcccaata cgcaaaccgc ctctccccgc gcgttggccg attcattaat gcagctggca     60

cgacaggttt cccgactgga aagcgccatg gttatgacaa cttgacggct acatcattca    120

ctttttcttc acaaccggca cggaactcgc tcgggctggc cccggtgcat tttttaaata    180

cccgcgagaa atagagttga tcgtcaaaac caacattgcg accgacggtg gcgataggca    240

tccgggtggt gctcaaaagc agcttcgcct ggctgatacg ttggtcctcg cgccagctta    300

agacgctaat ccctaactgc tggcggaaaa gatgtgacag acgcgacggc gacaagcaaa    360

catgctgtgc gacgctggcg atatcaaaat tgctgtctgc caggtgatcg ctgatgtact    420

gacaagcctc gcgtacccga ttatccatcg gtggatggag cgactcgtta atcgcttcca    480

tgcgccgcag taacaattgc tcaagcagat ttatcgccag cagctccgaa tagcgccctt    540

ccccttgccc ggcgttaatg atttgcccaa acaggtcgct gaaatgcggc tggtgcgctt    600

catccgggcg aaagaacccc gtattggcaa atattgacgg ccagttaagc cattcatgcc    660

agtaggcgcg cggacgaaag taaacccact ggtgatacca ttcgcgagcc tccggatgac    720

gaccgtagtg atgaatctct cctggcggga acagcaaaat atcacccggt cggcaaacaa    780

attctcgtcc ctgatttttc accacccct gaccgcgaat ggtgagattg agaatataac    840

ctttcattcc cagcggtcgg tcgataaaaa aatcgagata accgttggcc tcaatcggcg    900

ttaaacccgc caccagatgg gcattaaacg agtatcccgg cagcagggga tcattttgcg    960
```

-continued

```
cttcagccat acttttcata ctcccgccat tcagagaaga aaccaattgt ccatattgca   1020
tcagacattg ccgtcactgc gtcttttact ggctcttctc gctaaccaaa ccggtaaccc   1080
cgcttattaa aagcattctg taacaaagcg ggaccaaagc catgacaaaa acgcgtaaca   1140
aaagtgtcta taatcacggc agaaaagtcc acattgatta tttgcacggc gtcacacttt   1200
gctatgccat agcattttta tccataagat tagcggatcc tacctgacgc tttttatcgc   1260
aactctctac tgtttctcca tacccgtttg aattctctag actcgagagg aggattacaa   1320
aatgaaacca actacggtaa ttggtgcagg cttcggtggc ctggcactgg caattcgtct   1380
acaagctgcg gggatccccg tcttactgct tgaacaacgt gataaacccg gcggtcgggc   1440
ttatgtctac gaggatcagg ggtttacctt tgatgcaggc ccgacggtta tcaccgatcc   1500
cagtgccatt gaagaactgt ttgcactggc aggaaaacag ttaaaagagt atgtcgaact   1560
gctgccggtt acgccgtttt accgcctgtg ttgggagtca gggaaggtct ttaattacga   1620
taacgatcaa acccggctcg aagcgcagat tcagcagttt aatccccgcg atgtcgaagg   1680
ttatcgtcag tttctggact attcacgcgc ggtgtttaaa gaaggctatc taaagctcgg   1740
tactgtccct tttttatcgt tcagagacat gcttcgcgcc gcacctcaac tggcgaaact   1800
gcaggcatgg agaagcgttt acagtaaggt tgccagttac atcgaagatg aacatctgcg   1860
ccaggcgttt tctttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt ccttctctgt ttgtgctcta ttttggtttg aatcaccatc atgatcagct   2280
cgcgcatcac acggtttgtt tcggcccgcg ttaccgcgag ctgattgacg aaatttttaa   2340
tcatgatggc ctcgcagagg acttctcact ttatctgcac gcgccctgtg tcacggattc   2400
gtcactggcg cctgaaggtt gcggcagtta ctatgtgttg gcgccggtgc cacatttagg   2460
caccgcgaac ctcgactgga cggttgaggg gccaaaacta cgcgaccgta tttttgcgta   2520
ccttgagcag cattacatgc ctggcttacg gagtcagctg gtcacgcacc ggatgtttac   2580
gccgtttgat tttcgcgacc agcttaatgc ctatcatggc tcagcctttt ctgtggagcc   2640
cgttcttacc cagagcgcct ggtttcggcc gcataaccgc gataaaacca ttactaatct   2700
ctacctggtc ggcgcaggca cgcatcccgg cgcaggcatt cctggcgtca tcggctcggc   2760
aaaagcgaca gcaggtttga tgctggagga tctgatttga gggcccgtgt aggaggatta   2820
caaaatgcaa ccgcattatg atctgattct cgtgggggct ggactcgcga atggccttat   2880
cgccctgcgt cttcagcagc agcaacctga tatgcgtatt ttgcttatcg acgccgcacc   2940
ccaggcgggc gggaatcata cgtggtcatt tcaccacgat gatttgactg agagccaaca   3000
tcgttggata gctccgctgg tggttcatca ctggcccgac tatcaggtac gctttcccac   3060
acgccgtcgt aagctgaaca gcggctactt ttgtattact tctcagcgtt tcgctgaggt   3120
tttacagcga cagtttggcc cgcacttgtg gatggatacc gcggtcgcag aggttaatgc   3180
ggaatctgtt cggttgaaaa agggtcaggt tatcggtgcc cgcgcggtga ttgacgggcg   3240
gggttatgcg gcaaattcag cactgagcgt gggcttccag gcgtttattg gccaggaatg   3300
gcgattgagc cacccgcatg gtttatcgtc tcccattatc atggatgcca cggtcgatca   3360
```

gcaaaatggt tatcgcttcg tgtacagcct gccgctctcg ccgaccagat tgttaattga 3420
agacacgcac tatattgata atgcgacatt agatcctgaa tgcgcgcggc aaaatatttg 3480
cgactatgcc gcgcaacagg gttggcagct tcagacactg ctgcgagaag aacagggcgc 3540
cttacccatt actctgtcgg gcaatgccga cgcattctgg cagcagcgcc ccctggcctg 3600
tagtggatta cgtgccggtc tgttccatcc taccaccggc tattcactgc cgctggcggt 3660
tgccgtggcc gaccgcctga gtgcacttga tgtctttacg tcggcctcaa ttcaccatgc 3720
cattacgcat tttgcccgcg agcgctggca gcagcagggc tttttccgca tgctgaatcg 3780
catgctgttt ttagccggac ccgccgattc acgctggcgg gttatgcagc gtttttatgg 3840
tttacctgaa gatttaattg cccgttttta tgcgggaaaa ctcacgctga ccgatcggct 3900
acgtattctg agcggcaagc cgcctgttcc ggtattagca gcattgcaag ccattatgac 3960
gactcatcgt taaactagat aactagtagg aggattacaa atgttgaggg atctgctcat 4020
caccaccctg gcgctgagcc tgatcatcgg cctgcgctat ctgctggtcg gcgcggcggc 4080
ccatgggctg ctgtgggccg gggcgggccg gggacgggcg ctgaacctgc ggccgccggc 4140
gatgaagcgc atccgcgccg agatcgtcgc ctccctgatc gcctgcccca tctacgccct 4200
gccggcggcc ctggtgctgg agctgtggaa gcggggcggg acggcgatct acagcgatcc 4260
cgacgcctgg cccctgtggt ggctgccggt cagtctgatc gtctatctgc tggcgcacga 4320
cgccttctac tactgggtgc acagggccct gcatcacccg cgcgtcttcg gctgggccca 4380
tgccgaacac caccggtcgc gcgaccccag cgccttcgcc tccttcgcct tcgacccggc 4440
cgaggctgcg gccaccgcct ggttcctgcc cgccctggcc ctgatcgtgc cgatccactg 4500
gggcgtggcc ctgaccctgc tgacgctgat gtcgctgacg gccgccctga accatgcggg 4560
gcgcgaggtc tggcccgccg cctggctgga gcgggcgccg cttcgctggc tgatcaccgc 4620
cacccaccac gacgcccacc acaagcggtt caacggaaac tacggcctct atttccagtt 4680
ctgggaccgc tgggccggga ctgaggtttc ggccgccccc tcgccaccat ccccggtcat 4740
ccctccagag cggccctcag cgcctcttcg gtgatctagt aatcgattca ctgtataaca 4800
ttaagaagga ggattacaaa atggcatggc tgacctggat cgcactgttc ctgaccgcat 4860
tcctgggtat ggaggctttc gcgtggatca tgcaccgtta tgtcatgcac ggtttcttgt 4920
ggtcgtggca tcgtagccat cacgagccgc acgaccaccc gctggaaaag aacgacctgt 4980
ttgccgttgt ctttgccgct ccggcgattg ttatggtggc ggtgggtctg cacctgtggc 5040
cttgggcctt gccggtcggt ctgggtatta ctgcgtacgg catggtttac ttcttctttc 5100
atgatggcct ggtgcatcgt cgtttcccga cgggctttag cggtcgcagc ggcttttgga 5160
cccgtcgcat ccaggcgcac cgtctgcacc atgcagtccg cacgcgtgag ggctgcgtgt 5220
cctttggctt cttgtgggtt cgcagcgcgc gtgccctgaa agcggaactg gcgcaaaaac 5280
gcggtagcag cagctctggt gcataaaagc tttatctagt tgctgatgcg gtattttctc 5340
cttacgcatc tgtgcggtat ttcacaccgc atatatggtg cactctcagt acaatctgct 5400
ctgatgccgc atagttaagc cagccccgac acccgccaac acccgctgac gcgccctgac 5460
gggcttgtct gctcccggca tccgcttaca gacaagctgt gaccgtctcc gggagctgca 5520
tgtgtcagag gttttcaccg tcatcaccga aacgcgcgag acgaaagggc ctcgtgatac 5580
gcctattttt ataggttaat gtcatgataa taatggtttc ttagacgtca ggtggcactt 5640
ttcggggaaa tgtgcgcgga acccctattt gtttattttt ctaaatacat tcaaatatgt 5700
atccgctcat gagacaataa ccctgataaa tgcttcaata atattgaaaa aggaagagta 5760
tgagtattca acatttccgt gtcgccctta ttcccttttt tgcggcattt tgccttcctg 5820
tttttgctca cccagaaacg ctggtgaaag taaaagatgc tgaagatcag ttgggtgcac 5880
gagtgggtta catcgaactg gatctcaaca gcggtaagat ccttgagagt tttcgccccg 5940
aagaacgttt tccaatgatg agcactttta aagttctgct atgtggcgcg gtattatccc 6000
gtattgacgc cgggcaagag caactcggtc gccgcataca ctattctcag aatgacttgg 6060
ttgagtactc accagtcaca gaaaagcatc ttacggatgg catgacagta agagaattat 6120
gcagtgctgc cataaccatg agtgataaca ctgcggccaa cttacttctg acaacgatcg 6180
gaggaccgaa ggagctaacc gcttttttgc acaacatggg ggatcatgta actcgccttg 6240
atcgttggga accggagctg aatgaagcca taccaaacga cgagcgtgac accacgatgc 6300
ctgtagcaat ggcaacaacg ttgcgcaaac tattaactgg cgaactactt actctagctt 6360
cccggcaaca attaatagac tggatggagg cggataaagt tgcaggacca cttctgcgct 6420
cggcccttcc ggctggctgg tttattgctg ataaatctgg agccggtgag cgtgggtctc 6480
gcggtatcat tgcagcactg gggccagatg gtaagccctc ccgtatcgta gttatctaca 6540
cgacggggag tcaggcaact atggatgaac gaaatagaca gatcgctgag ataggtgcct 6600
cactgattaa gcattggtaa ctgtcagacc aagtttactc atatatactt tagattgatt 6660
taaaacttca tttttaattt aaaaggatct aggtgaagat cctttttgat aatctcatga 6720
ccaaaatccc ttaacgtgag ttttcgttcc actgagcgtc agaccccgta gaaaagatca 6780
aaggatcttc ttgagatcct ttttttctgc gcgtaatctg ctgcttgcaa acaaaaaaac 6840
caccgctacc agcggtggtt tgtttgccgg atcaagagct accaactctt tttccgaagg 6900
taactggctt cagcagagcg cagataccaa atactgtcct tctagtgtag ccgtagttag 6960
gccaccactt caagaactct gtagcaccgc ctacatacct cgctctgcta atcctgttac 7020
cagtggctgc tgccagtggc gataagtcgt gtcttaccgg gttggactca agacgatagt 7080
taccggataa ggcgcagcgg tcgggctgaa cggggggttc gtgcacacag cccagcttgg 7140
agcgaacgac ctacaccgaa ctgagatacc tacagcgtga gctatgagaa agcgccacgc 7200
ttcccgaagg gagaaaggcg gacaggtatc cggtaagcgg cagggtcgga acaggagagc 7260
gcacgaggga gcttccaggg ggaaacgcct ggtatcttta tagtcctgtc gggtttcgcc 7320
acctctgact tgagcgtcga tttttgtgat gctcgtcagg ggggcggagc ctatggaaaa 7380
acgccagcaa cgcggccttt ttacggttcc tggccttttg ctggcctttt gctcacatgt 7440
tctttcctgc gttatcccct gattctgtgg ataaccgtat taccgccttt gagtgagctg 7500
ataccgctcg ccgcagccga acgaccgagc gcagcgagtc agtgagcgag gaagcggaag 7560
a 7561

<210> SEQ ID NO 21
<211> LENGTH: 8309
<212> TYPE: DNA
<213> ORGANISM: Artificial
<220> FEATURE:
<223> OTHER INFORMATION: Designed plasmid DNA, pUC-pBAD-CrtIN304P-CrtY-CrtG-CrtWBD-CrtZBD

<400> SEQUENCE: 21
gcgcccaata cgcaaaccgc ctctccccgc gcgttggccg attcattaat gcagctggca 60
cgacaggttt cccgactgga aagcgccatg gttatgacaa cttgacggct acatcattca 120

-continued

```
cttttcttc acaaccggca cggaactcgc tcgggctggc cccggtgcat tttttaaata    180
cccgcgagaa atagagttga tcgtcaaaac caacattgcg accgacggtg gcgataggca    240
tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
ccccttgccc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgatttttc accacccct gaccgcgaat ggtgagattg agaatataac    840
ctttcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat acttttcata ctcccgccat tcagagaaga aaccaattgt ccatattgca   1020
tcagacattg ccgtcactgc gtcttttact ggctcttctc gctaaccaaa ccggtaaccc   1080
cgcttattaa aagcattctg taacaaagcg ggaccaaagc catgacaaaa acgcgtaaca   1140
aaagtgtcta taatcacggc agaaaagtcc acattgatta tttgcacggc gtcacacttt   1200
gctatgccat agcattttta tccataagat tagcggatcc tacctgacgc tttttatcgc   1260
aactctctac tgtttctcca tacccgtttg aattctctag actcgagagg aggattacaa   1320
aatgaaacca actacggtaa ttggtgcagg cttcggtggc ctggcactgg caattcgtct   1380
acaagctgcg gggatccccg tcttactgct tgaacaacgt gataaacccg gcggtcgggc   1440
ttatgtctac gaggatcagg ggtttacctt tgatgcaggc ccgacggtta tcaccgatcc   1500
cagtgccatt gaagaactgt ttgcactggc aggaaaacag ttaaaagagt atgtcgaact   1560
gctgccggtt acgccgtttt accgcctgtg ttgggagtca gggaaggtct ttaattacga   1620
taacgatcaa acccggctcg aagcgcagat tcagcagttt aatccccgcg atgtcgaagg   1680
ttatcgtcag tttctggact attcacgcgc ggtgtttaaa gaaggctatc taaagctcgg   1740
tactgtccct tttttatcgt tcagagacat gcttcgcgcc gcacctcaac tggcgaaact   1800
gcaggcatgg agaagcgttt acagtaaggt tgccagttac atcgaagatg aacatctgcg   1860
ccaggcgttt tctttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt ccttctctgt ttgtgctcta ttttggtttg aatcaccatc atgatcagct   2280
cgcgcatcac acggtttgtt tcggcccgcg ttaccgcgag ctgattgacg aaatttttaa   2340
tcatgatggc ctcgcagagg acttctcact ttatctgcac gcgccctgtg tcacggattc   2400
gtcactggcg cctgaaggtt gcggcagtta ctatgtgttg gcgccggtgc cacatttagg   2460
caccgcgaac ctcgactgga cggttgaggg gccaaaacta cgcgaccgta tttttgcgta   2520
```

-continued

```
ccttgagcag cattacatgc ctggcttacg gagtcagctg gtcacgcacc ggatgtttac   2580
gccgtttgat tttcgcgacc agcttaatgc ctatcatggc tcagcctttt ctgtggagcc   2640
cgttcttacc cagagcgcct ggtttcggcc gcataaccgc gataaaacca ttactaatct   2700
ctacctggtc ggcgcaggca cgcatcccgg cgcaggcatt cctggcgtca tcggctcggc   2760
aaaagcgaca gcaggtttga tgctggagga tctgatttga gggcccgtgt aggaggatta   2820
caaaatgcaa ccgcattatg atctgattct cgtgggggct ggactcgcga atggccttat   2880
cgccctgcgt cttcagcagc agcaacctga tatgcgtatt ttgcttatcg acgccgcacc   2940
ccaggcgggc gggaatcata cgtggtcatt tcaccacgat gatttgactg agagccaaca   3000
tcgttggata gctccgctgg tggttcatca ctggcccgac tatcaggtac gctttcccac   3060
acgccgtcgt aagctgaaca gcggctactt ttgtattact tctcagcgtt tcgctgaggt   3120
tttacagcga cagtttggcc cgcacttgtg gatggatacc gcggtcgcag aggttaatgc   3180
ggaatctgtt cggttgaaaa agggtcaggt tatcggtgcc cgcgcggtga ttgacgggcg   3240
gggttatgcg gcaaattcag cactgagcgt gggcttccag gcgtttattg gccaggaatg   3300
gcgattgagc cacccgcatg gtttatcgtc tcccattatc atggatgcca cggtcgatca   3360
gcaaaatggt tatcgcttcg tgtacagcct gccgctctcg ccgaccagat tgttaattga   3420
agacacgcac tatattgata atgcgacatt agatcctgaa tgcgcgcggc aaaatatttg   3480
cgactatgcc gcgcaacagg gttggcagct tcagacactg ctgcgagaag aacagggcgc   3540
cttacccatt actctgtcgg gcaatgccga cgcattctgg cagcagcgcc ccctggcctg   3600
tagtggatta cgtgccggtc tgttccatcc taccaccggc tattcactgc cgctggcggt   3660
tgccgtggcc gaccgcctga gtgcacttga tgtctttacg tcggcctcaa ttcaccatgc   3720
cattacgcat tttgcccgcg agcgctggca gcagcagggc tttttccgca tgctgaatcg   3780
catgctgttt ttagccggac ccgccgattc acgctggcgg gttatgcagc gtttttatgg   3840
tttacctgaa gatttaattg cccgttttta tgcgggaaaa ctcacgctga ccgatcggct   3900
acgtattctg agcggcaagc cgcctgttcc ggtattagca gcattgcaag ccattatgac   3960
gactcatcgt taaactagat aactagtagg aggattacaa atgttgaggg atctgctcat   4020
caccaccctg gcgctgagcc tgatcatcgg cctgcgctat ctgctggtcg gcgcggcggc   4080
ccatgggctg ctgtgggccg gggcgggccg gggacgggcg ctgaacctgc ggccgccggc   4140
gatgaagcgc atccgcgccg agatcgtcgc ctccctgatc gcctgcccca tctacgccct   4200
gccggcggcc ctggtgctgg agctgtggaa gcggggcggg acggcgatct acagcgatcc   4260
cgacgcctgg ccccctgtggt ggctgccggt cagtctgatc gtctatctgc tggcgcacga   4320
cgccttctac tactgggtgc acagggccct gcatcacccg cgcgtcttcg gctgggccca   4380
tgccgaacac caccggtcgc gcgaccccag cgccttcgcc tccttcgcct tcgacccggc   4440
cgaggctgcg gccaccgcct ggttcctgcc cgccctggcc ctgatcgtgc cgatccactg   4500
gggcgtggcc ctgaccctgc tgacgctgat gtcgctgacg gccgccctga accatgcggg   4560
gcgcgaggtc tggcccgccg cctggctgga gcgggcgccg cttcgctggc tgatcaccgc   4620
cacccaccac gacgcccacc acaagcggtt caacggaaac tacggcctct atttccagtt   4680
ctgggaccgc tgggccggga ctgaggtttc ggccgccccc tcgccaccat ccccggtcat   4740
ccctccagag cggccctcag cgcctcttcg gtgatctagt aggaggatta caaaatgacc   4800
gcagctgtcg cagaacctcg cattgtaccg cgccaaacct ggatcggcct gaccctggcg   4860
```

-continued

```
ggtatgattg tggcgggctg gggttctctg cacgtgtacg gtgtgtactt ccaccgttgg   4920
ggcaccagca gcctggttat cgtcccggct atcgtggccg ttcagacgtg gttgtcggtt   4980
ggcctgttta ttgtcgcaca tgacgccatg cacggttccc tggccccagg ccgtccgcgc   5040
ctgaacgcag cggtgggtcg tctgacgctg ggtctgtatg caggcttccg tttcgatcgc   5100
ttgaaaacgg cgcaccacgc gcatcatgcg gctccgggta ccgcagatga cccggacttt   5160
tacgcgcctg cgccacgcgc cttcctgccg tggtttttga actttttccg tacctatttc   5220
ggttggcgcg agatggcggt tctgaccgcg ctggtcctga tcgcgctgtt tggcttgggt   5280
gcccgtccgg cgaatctgtt gactttttgg gccgcaccgg cgctgctgag cgcgctgcaa   5340
ctgttcacgt ttggcacctg gctgccgcac cgtcacacgg accagccgtt cgcggatgct   5400
catcatgcac gcagcagcgg ttatggtccg gttctgagcc tgctgacctg ctttcatttc   5460
ggtcgtcatc acgagcacca cctgacgccg tggcgtccgt ggtggcgttt gtggcgtggt   5520
gaaagctaaa tcgattcact gtataacatt aagaaggagg attacaaaat ggcatggctg   5580
acctggatcg cactgttcct gaccgcattc ctgggtatgg aggctttcgc gtggatcatg   5640
caccgttatg tcatgcacgg tttcttgtgg tcgtggcatc gtagccatca cgagccgcac   5700
gaccacccgc tggaaaagaa cgacctgttt gccgttgtct ttgccgctcc ggcgattgtt   5760
atggtggcgg tgggtctgca cctgtggcct tgggccttgc cggtcggtct gggtattact   5820
gcgtacggca tggtttactt cttctttcat gatggcctgg tgcatcgtcg tttcccgacg   5880
ggctttagcg gtcgcagcgg cttttggacc cgtcgcatcc aggcgcaccg tctgcaccat   5940
gcagtccgca cgcgtgaggg ctgcgtgtcc tttggcttct tgtgggttcg cagcgcgcgt   6000
gccctgaaag cggaactggc gcaaaaacgc ggtagcagca gctctggtgc ataaaagctt   6060
tatctagttg ctgatgcggt attttctcct tacgcatctg tgcggtattt cacaccgcat   6120
atatggtgca ctctcagtac aatctgctct gatgccgcat agttaagcca gccccgacac   6180
ccgccaacac ccgctgacgc gccctgacgg gcttgtctgc tcccggcatc cgcttacaga   6240
caagctgtga ccgtctccgg gagctgcatg tgtcagaggt tttcaccgtc atcaccgaaa   6300
cgcgcgagac gaaagggcct cgtgatacgc ctatttttat aggttaatgt catgataata   6360
atggtttctt agacgtcagg tggcactttt cggggaaatg tgcgcggaac ccctatttgt   6420
ttatttttct aaatacattc aaatatgtat ccgctcatga gacaataacc ctgataaatg   6480
cttcaataat attgaaaaag gaagagtatg agtattcaac atttccgtgt cgcccttatt   6540
ccctttttttg cggcattttg ccttcctgtt tttgctcacc cagaaacgct ggtgaaagta   6600
aaagatgctg aagatcagtt gggtgcacga gtgggttaca tcgaactgga tctcaacagc   6660
ggtaagatcc ttgagagttt tcgccccgaa gaacgttttc caatgatgag cacttttaaa   6720
gttctgctat gtggcgcggt attatcccgt attgacgccg ggcaagagca actcggtcgc   6780
cgcatacact attctcagaa tgacttggtt gagtactcac cagtcacaga aaagcatctt   6840
acggatggca tgacagtaag agaattatgc agtgctgcca taaccatgag tgataacact   6900
gcggccaact tacttctgac aacgatcgga ggaccgaagg agctaaccgc ttttttgcac   6960
aacatggggg atcatgtaac tcgccttgat cgttgggaac cggagctgaa tgaagccata   7020
ccaaacgacg agcgtgacac cacgatgcct gtagcaatgg caacaacgtt gcgcaaacta   7080
ttaactggcg aactacttac tctagcttcc cggcaacaat taatagactg gatggaggcg   7140
gataaagttg caggaccact tctgcgctcg gcccttccgg ctggctggtt tattgctgat   7200
aaatctggag ccggtgagcg tgggtctcgc ggtatcattg cagcactggg gccagatggt   7260
```

```
aagccctccc gtatcgtagt tatctacacg acggggagtc aggcaactat ggatgaacga   7320

aatagacaga tcgctgagat aggtgcctca ctgattaagc attggtaact gtcagaccaa   7380

gtttactcat atatacttta gattgattta aaacttcatt tttaatttaa aaggatctag   7440

gtgaagatcc tttttgataa tctcatgacc aaaatccctt aacgtgagtt ttcgttccac   7500

tgagcgtcag accccgtaga aaagatcaaa ggatcttctt gagatccttt ttttctgcgc   7560

gtaatctgct gcttgcaaac aaaaaaacca ccgctaccag cggtggtttg tttgccggat   7620

caagagctac caactctttt tccgaaggta actggcttca gcagagcgca gataccaaat   7680

actgtccttc tagtgtagcc gtagttaggc caccacttca agaactctgt agcaccgcct   7740

acatacctcg ctctgctaat cctgttacca gtggctgctg ccagtggcga taagtcgtgt   7800

cttaccgggt tggactcaag acgatagtta ccggataagg cgcagcggtc gggctgaacg   7860

gggggttcgt gcacacagcc cagcttggag cgaacgacct acaccgaact gagataccta   7920

cagcgtgagc tatgagaaag cgccacgctt cccgaaggga gaaaggcgga caggtatccg   7980

gtaagcggca gggtcggaac aggagagcgc acgagggagc ttccaggggg aaacgcctgg   8040

tatctttata gtcctgtcgg gtttcgccac ctctgacttg agcgtcgatt tttgtgatgc   8100

tcgtcagggg ggcggagcct atggaaaaac gccagcaacg cggccttttt acggttcctg   8160

gccttttgct ggccttttgc tcacatgttc tttcctgcgt tatcccctga ttctgtggat   8220

aaccgtatta ccgcctttga gtgagctgat accgctcgcc gcagccgaac gaccgagcgc   8280

agcgagtcag tgagcgagga agcggaaga                                     8309
```

<210> SEQ ID NO 22
<211> LENGTH: 8083
<212> TYPE: DNA
<213> ORGANISM: Artificial
<220> FEATURE:
<223> OTHER INFORMATION: Designed plasmid DNA, pUC-pBAD-CrtIN304P-CrtY-CrtX-CrtZBD

<400> SEQUENCE: 22

```
gcgcccaata cgcaaaccgc ctctccccgc gcgttggccg attcattaat gcagctggca     60

cgacaggttt cccgactgga aagcgccatg gttatgacaa cttgacggct acatcattca    120

ctttttcttc acaaccggca cggaactcgc tcgggctggc cccggtgcat tttttaaata    180

cccgcgagaa atagagttga tcgtcaaaac caacattgcg accgacggtg gcgataggca    240

tccgggtggt gctcaaaagc agcttcgcct ggctgatacg ttggtcctcg cgccagctta    300

agacgctaat ccctaactgc tggcggaaaa gatgtgacag acgcgacggc gacaagcaaa    360

catgctgtgc gacgctggcg atatcaaaat tgctgtctgc caggtgatcg ctgatgtact    420

gacaagcctc gcgtacccga ttatccatcg gtggatggag cgactcgtta atcgcttcca    480

tgcgccgcag taacaattgc tcaagcagat ttatcgccag cagctccgaa tagcgccctt    540

ccccttgccc ggcgttaatg atttgcccaa acaggtcgct gaaatgcggc tggtgcgctt    600

catccgggcg aaagaacccc gtattggcaa atattgacgg ccagttaagc cattcatgcc    660

agtaggcgcg cggacgaaag taaacccact ggtgatacca ttcgcgagcc tccggatgac    720

gaccgtagtg atgaatctct cctggcggga acagcaaaat atcacccggt cggcaaacaa    780

attctcgtcc ctgatttttc accacccccct gaccgcgaat ggtgagattg agaatataac    840

ctttcattcc cagcggtcgg tcgataaaaa aatcgagata accgttggcc tcaatcggcg    900

ttaaacccgc caccagatgg gcattaaacg agtatcccgg cagcagggga tcattttgcg    960
```

```
cttcagccat acttttcata ctcccgccat tcagagaaga aaccaattgt ccatattgca   1020
tcagacattg ccgtcactgc gtcttttact ggctcttctc gctaaccaaa ccggtaaccc   1080
cgcttattaa aagcattctg taacaaagcg ggaccaaagc catgacaaaa acgcgtaaca   1140
aaagtgtcta taatcacggc agaaaagtcc acattgatta tttgcacggc gtcacacttt   1200
gctatgccat agcattttta tccataagat tagcggatcc tacctgacgc tttttatcgc   1260
aactctctac tgtttctcca tacccgtttg aattctctag actcgagagg aggattacaa   1320
aatgaaacca actacggtaa ttggtgcagg cttcggtggc ctggcactgg caattcgtct   1380
acaagctgcg gggatccccg tcttactgct tgaacaacgt gataaacccg gcggtcgggc   1440
ttatgtctac gaggatcagg ggtttacctt tgatgcaggc ccgacggtta tcaccgatcc   1500
cagtgccatt gaagaactgt ttgcactggc aggaaaacag ttaaaagagt atgtcgaact   1560
gctgccggtt acgccgtttt accgcctgtg ttgggagtca gggaaggtct ttaattacga   1620
taacgatcaa acccggctcg aagcgcagat tcagcagttt aatccccgcg atgtcgaagg   1680
ttatcgtcag tttctggact attcacgcgc ggtgtttaaa gaaggctatc taaagctcgg   1740
tactgtccct ttttatcgt tcagagacat gcttcgcgcc gcacctcaac tggcgaaact   1800
gcaggcatgg agaagcgttt acagtaaggt tgccagttac atcgaagatg aacatctgcg   1860
ccaggcgttt tctttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt ccttctctgt ttgtgctcta ttttggtttg aatcaccatc atgatcagct   2280
cgcgcatcac acggtttgtt tcggcccgcg ttaccgcgag ctgattgacg aaatttttaa   2340
tcatgatggc ctcgcagagg acttctcact ttatctgcac gcgccctgtg tcacggattc   2400
gtcactggcg cctgaaggtt gcggcagtta ctatgtgttg gcgccggtgc cacatttagg   2460
caccgcgaac ctcgactgga cggttgaggg gccaaaacta cgcgaccgta tttttgcgta   2520
ccttgagcag cattacatgc ctggcttacg gagtcagctg gtcacgcacc ggatgtttac   2580
gccgtttgat tttcgcgacc agcttaatgc ctatcatggc tcagcctttt ctgtggagcc   2640
cgttcttacc cagagcgcct ggtttcggcc gcataaccgc gataaaacca ttactaatct   2700
ctacctggtc ggcgcaggca cgcatcccgg cgcaggcatt cctggcgtca tcggctcggc   2760
aaaagcgaca gcaggtttga tgctggagga tctgatttga gggcccgtgt aggaggatta   2820
caaaatgcaa ccgcattatg atctgattct cgtgggggct ggactcgcga atggccttat   2880
cgccctgcgt cttcagcagc agcaacctga tatgcgtatt ttgcttatcg acgccgcacc   2940
ccaggcgggc gggaatcata cgtggtcatt tcaccacgat gatttgactg agagccaaca   3000
tcgttggata gctccgctgg tggttcatca ctggcccgac tatcaggtac gctttcccac   3060
acgccgtcgt aagctgaaca gcggctactt ttgtattact tctcagcgtt tcgctgaggt   3120
tttacagcga cagtttggcc cgcacttgtg gatggatacc gcggtcgcag aggttaatgc   3180
ggaatctgtt cggttgaaaa agggtcaggt tatcggtgcc cgcgcggtga ttgacgggcg   3240
gggttatgcg gcaaattcag cactgagcgt gggcttccag gcgtttattg gccaggaatg   3300
```

-continued

```
gcgattgagc cacccgcatg gtttatcgtc tcccattatc atggatgcca cggtcgatca   3360
gcaaaatggt tatcgcttcg tgtacagcct gccgctctcg ccgaccagat tgttaattga   3420
agacacgcac tatattgata atgcgacatt agatcctgaa tgcgcgcggc aaaatatttg   3480
cgactatgcc gcgcaacagg gttggcagct tcagacactg ctgcgagaag aacagggcgc   3540
cttacccatt actctgtcgg gcaatgccga cgcattctgg cagcagcgcc ccctggcctg   3600
tagtggatta cgtgccggtc tgttccatcc taccaccggc tattcactgc cgctggcggt   3660
tgccgtggcc gaccgcctga gtgcacttga tgtctttacg tcggcctcaa ttcaccatgc   3720
cattacgcat tttgcccgcg agcgctggca gcagcagggc tttttccgca tgctgaatcg   3780
catgctgttt ttagccggac ccgccgattc acgctggcgg gttatgcagc gtttttatgg   3840
tttacctgaa gatttaattg cccgttttta tgcgggaaaa ctcacgctga ccgatcggct   3900
acgtattctg agcggcaagc cgcctgttcc ggtattagca gcattgcaag ccattatgac   3960
gactcatcgt taaactagat aactagtagg aggattacaa atgagccatt tcgcggcgat   4020
cgcaccgcct ttttacagcc atgttcgcgc attacagaat ctcgctcagg aactggtcgc   4080
gcgcggtcat cgggtgacct ttattcagca atacgatatt aaacacttga tcgatagcga   4140
aaccattgga tttcattccg tcgggacaga cagccatccc cccggcgcgt taacgcgcgt   4200
gctacacctg gcggctcatc ctctggggcc gtcaatgctg aagctcatca atgaaatggc   4260
gcgcaccacc gatatgctgt gccgcgaact cccccaggca tttaacgatc tggccgtcga   4320
tggcgtcatt gttgatcaaa tggaaccggc aggcgcgctc gttgctgaag cactgggact   4380
gccgtttatc tctgtcgcct gcgcgctgcc tctcaatcgt gaaccggata tgcccctggc   4440
ggttatgcct ttcgaatacg ggaccagcga cgcggctcgc gaacgttatg ccgccagtga   4500
aaaaatttat gactggctaa tgcgtcgtca tgaccgtgtc attgccgaac acagccacag   4560
aatgggctta gccccccggc aaaagcttca ccagtgtttt tcgccactgg cgcaaatcag   4620
ccagcttgtt cctgaactgg attttccccg caaagcgtta ccggcttgtt ttcatgccgt   4680
cgggcctctg cgcgaaacgc acgcaccgtc aacgtcttca tcccgttatt ttacatcctc   4740
agaaaaaccc cggattttcg cctcgctggg cacgcttcag ggacaccgtt atgggctgtt   4800
taaaacgata gtgaaagcct gtgaagaaat tgacggtcag ctcctgttag cccactgtgg   4860
tcgtcttacg gactctcagt gtgaagagct ggcgcgaagc cgtcatacac aggtggtgga   4920
ttttgccgat cagtcagccg cgctgtctca ggcgcagctg gcgatcaccc acggcggcat   4980
gaatacggta ctggacgcga ttaattaccg gacgcccctt ttagcgcttc cgctggcctt   5040
tgatcagccc ggcgtcgcgt cacgcatcgt ttatcacggc atcggcaagc gtgcttcccg   5100
ctttaccacc agccatgctt tggctcgtca gatgcgttca ttgctgacca acgtcgactt   5160
tcagcagcgc atggcgaaaa tccagacagc ccttcgtttg gcagggggca ccatggccgc   5220
tgccgatatc attgagcagg ttatgtgcac cggtcagcct gtcttaagtg ggagcggcta   5280
tgcaaccgca ttatgatcta gtaatcgatt cactgtataa cattaagaag gaggattaca   5340
aaatggcatg gctgacctgg atcgcactgt tcctgaccgc attcctgggt atggaggctt   5400
tcgcgtggat catgcaccgt tatgtcatgc acggtttctt gtggtcgtgg catcgtagcc   5460
atcacgagcc gcacgaccac ccgctggaaa agaacgacct gtttgccgtt gtctttgccg   5520
ctccggcgat tgttatggtg gcggtgggtc tgcacctgtg gccttgggcc ttgccggtcg   5580
gtctgggtat tactgcgtac ggcatggttt acttcttctt tcatgatggc ctggtgcatc   5640
gtcgtttccc gacgggcttt agcggtcgca gcggcttttg gacccgtcgc atccaggcgc   5700
```

-continued accgtctgca ccatgcagtc cgcacgcgtg agggctgcgt gtcctttggc ttcttgtggg 5760
ttcgcagcgc gcgtgccctg aaagcggaac tggcgcaaaa acgcggtagc agcagctctg 5820
gtgcataaaa gctttatcta gttgctgatg cggtattttc tccttacgca tctgtgcggt 5880
atttcacacc gcatatatgg tgcactctca gtacaatctg ctctgatgcc gcatagttaa 5940
gccagccccg acacccgcca acacccgctg acgcgccctg acgggcttgt ctgctcccgg 6000
catccgctta cagacaagct gtgaccgtct ccgggagctg catgtgtcag aggttttcac 6060
cgtcatcacc gaaacgcgcg agacgaaagg gcctcgtgat acgcctattt ttataggtta 6120
atgtcatgat aataatggtt tcttagacgt caggtggcac ttttcgggga aatgtgcgcg 6180
gaacccctat ttgtttattt ttctaaatac attcaaatat gtatccgctc atgagacaat 6240
aaccctgata aatgcttcaa taatattgaa aaaggaagag tatgagtatt caacatttcc 6300
gtgtcgccct tattcccttt tttgcggcat tttgccttcc tgtttttgct cacccagaaa 6360
cgctggtgaa agtaaaagat gctgaagatc agttgggtgc acgagtgggt tacatcgaac 6420
tggatctcaa cagcggtaag atccttgaga gttttcgccc cgaagaacgt tttccaatga 6480
tgagcacttt taaagttctg ctatgtggcg cggtattatc ccgtattgac gccgggcaag 6540
agcaactcgg tcgccgcata cactattctc agaatgactt ggttgagtac tcaccagtca 6600
cagaaaagca tcttacggat ggcatgacag taagagaatt atgcagtgct gccataacca 6660
tgagtgataa cactgcggcc aacttacttc tgacaacgat cggaggaccg aaggagctaa 6720
ccgctttttt gcacaacatg ggggatcatg taactcgcct tgatcgttgg gaaccggagc 6780
tgaatgaagc cataccaaac gacgagcgtg acaccacgat gcctgtagca atggcaacaa 6840
cgttgcgcaa actattaact ggcgaactac ttactctagc ttcccggcaa caattaatag 6900
actggatgga ggcggataaa gttgcaggac cacttctgcg ctcggccctt ccggctggct 6960
ggtttattgc tgataaatct ggagccggtg agcgtgggtc tcgcggtatc attgcagcac 7020
tggggccaga tggtaagccc tcccgtatcg tagttatcta cacgacgggg agtcaggcaa 7080
ctatggatga acgaaataga cagatcgctg agataggtgc ctcactgatt aagcattggt 7140
aactgtcaga ccaagtttac tcatatatac tttagattga tttaaaactt catttttaat 7200
ttaaaaggat ctaggtgaag atcctttttg ataatctcat gaccaaaatc ccttaacgtg 7260
agttttcgtt ccactgagcg tcagaccccg tagaaaagat caaaggatct tcttgagatc 7320
ctttttttct gcgcgtaatc tgctgcttgc aaacaaaaaa accaccgcta ccagcggtgg 7380
tttgtttgcc ggatcaagag ctaccaactc tttttccgaa ggtaactggc ttcagcagag 7440
cgcagatacc aaatactgtc cttctagtgt agccgtagtt aggccaccac ttcaagaact 7500
ctgtagcacc gcctacatac ctcgctctgc taatcctgtt accagtggct gctgccagtg 7560
gcgataagtc gtgtcttacc gggttggact caagacgata gttaccggat aaggcgcagc 7620
ggtcgggctg aacggggggt tcgtgcacac agcccagctt ggagcgaacg acctacaccg 7680
aactgagata cctacagcgt gagctatgag aaagcgccac gcttcccgaa gggagaaagg 7740
cggacaggta tccggtaagc ggcagggtcg gaacaggaga gcgcacgagg gagcttccag 7800
ggggaaacgc ctggtatctt tatagtcctg tcgggtttcg ccacctctga cttgagcgtc 7860
gatttttgtg atgctcgtca ggggggcgga gcctatggaa aaacgccagc aacgcggcct 7920
ttttacggtt cctggccttt tgctggcctt ttgctcacat gttctttcct gcgttatccc 7980
ctgattctgt ggataaccgt attaccgcct ttgagtgagc tgataccgct cgccgcagcc 8040
gaacgaccga gcgcagcgag tcagtgagcg aggaagcgga aga 8083

<210> SEQ ID NO 23
<211> LENGTH: 8831
<212> TYPE: DNA
<213> ORGANISM: Artificial
<220> FEATURE:
<223> OTHER INFORMATION: Designed plasmid DNA, pUC-pBAD-CrtIN304P-CrtY-
CrtX-CrtWBD-CrtZBD

<400> SEQUENCE: 23
gcgcccaata cgcaaaccgc ctctccccgc gcgttggccg attcattaat gcagctggca 60
cgacaggttt cccgactgga aagcgccatg gttatgacaa cttgacggct acatcattca 120
ctttttcttc acaaccggca cggaactcgc tcgggctggc cccggtgcat tttttaaata 180
cccgcgagaa atagagttga tcgtcaaaac caacattgcg accgacggtg gcgataggca 240
tccgggtggt gctcaaaagc agcttcgcct ggctgatacg ttggtcctcg cgccagctta 300
agacgctaat ccctaactgc tggcggaaaa gatgtgacag acgcgacggc gacaagcaaa 360
catgctgtgc gacgctggcg atatcaaaat tgctgtctgc caggtgatcg ctgatgtact 420
gacaagcctc gcgtacccga ttatccatcg gtggatggag cgactcgtta atcgcttcca 480
tgcgccgcag taacaattgc tcaagcagat ttatcgccag cagctccgaa tagcgccctt 540
ccccttgccc ggcgttaatg atttgcccaa acaggtcgct gaaatgcggc tggtgcgctt 600
catccgggcg aaagaacccc gtattggcaa atattgacgg ccagttaagc cattcatgcc 660
agtaggcgcg cggacgaaag taaacccact ggtgatacca ttcgcgagcc tccggatgac 720
gaccgtagtg atgaatctct cctggcggga acagcaaaat atcacccggt cggcaaacaa 780
attctcgtcc ctgatttttc accacccccct gaccgcgaat ggtgagattg agaatataac 840
ctttcattcc cagcggtcgg tcgataaaaa aatcgagata accgttggcc tcaatcggcg 900
ttaaacccgc caccagatgg gcattaaacg agtatcccgg cagcagggga tcattttgcg 960
cttcagccat acttttcata ctcccgccat tcagagaaga aaccaattgt ccatattgca 1020
tcagacattg ccgtcactgc gtcttttact ggctcttctc gctaaccaaa ccggtaaccc 1080
cgcttattaa aagcattctg taacaaagcg ggaccaaagc catgacaaaa acgcgtaaca 1140
aaagtgtcta taatcacggc agaaaagtcc acattgatta tttgcacggc gtcacacttt 1200
gctatgccat agcattttta tccataagat tagcggatcc tacctgacgc tttttatcgc 1260
aactctctac tgtttctcca tacccgtttg aattctctag actcgagagg aggattacaa 1320
aatgaaacca actacggtaa ttggtgcagg cttcggtggc ctggcactgg caattcgtct 1380
acaagctgcg gggatccccg tcttactgct tgaacaacgt gataaacccg gcggtcgggc 1440
ttatgtctac gaggatcagg ggtttacctt tgatgcaggc ccgacggtta tcaccgatcc 1500
cagtgccatt gaagaactgt ttgcactggc aggaaaacag ttaaaagagt atgtcgaact 1560
gctgccggtt acgccgtttt accgcctgtg ttgggagtca gggaaggtct ttaattacga 1620
taacgatcaa acccggctcg aagcgcagat tcagcagttt aatccccgcg atgtcgaagg 1680
ttatcgtcag tttctggact attcacgcgc ggtgtttaaa gaaggctatc taaagctcgg 1740
tactgtccct tttttatcgt tcagagacat gcttcgcgcc gcacctcaac tggcgaaact 1800
gcaggcatgg agaagcgttt acagtaaggt tgccagttac atcgaagatg aacatctgcg 1860
ccaggcgttt tctttccact cgctgttggt gggcggcaat cccttcgcca cctcatccat 1920
ttatacgttg atacacgcgc tggagcgtga gtggggcgtc tggtttccgc gtggcggcac 1980

-continued

```
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt ccttctctgt ttgtgctcta ttttggtttg aatcaccatc atgatcagct   2280
cgcgcatcac acggtttgtt tcggcccgcg ttaccgcgag ctgattgacg aaatttttaa   2340
tcatgatggc ctcgcagagg acttctcact ttatctgcac gcgccctgtg tcacggattc   2400
gtcactggcg cctgaaggtt gcggcagtta ctatgtgttg gcgccggtgc cacatttagg   2460
caccgcgaac ctcgactgga cggttgaggg gccaaaacta cgcgaccgta tttttgcgta   2520
ccttgagcag cattacatgc ctggcttacg gagtcagctg gtcacgcacc ggatgtttac   2580
gccgtttgat tttcgcgacc agcttaatgc ctatcatggc tcagcctttt ctgtggagcc   2640
cgttcttacc cagagcgcct ggtttcggcc gcataaccgc gataaaacca ttactaatct   2700
ctacctggtc ggcgcaggca cgcatcccgg cgcaggcatt cctggcgtca tcggctcggc   2760
aaaagcgaca gcaggtttga tgctggagga tctgatttga gggcccgtgt aggaggatta   2820
caaaatgcaa ccgcattatg atctgattct cgtgggggct ggactcgcga atggccttat   2880
cgccctgcgt cttcagcagc agcaacctga tatgcgtatt ttgcttatcg acgccgcacc   2940
ccaggcgggc gggaatcata cgtggtcatt tcaccacgat gatttgactg agagccaaca   3000
tcgttggata gctccgctgg tggttcatca ctggcccgac tatcaggtac gctttcccac   3060
acgccgtcgt aagctgaaca gcggctactt ttgtattact tctcagcgtt tcgctgaggt   3120
tttacagcga cagtttggcc cgcacttgtg gatggatacc gcggtcgcag aggttaatgc   3180
ggaatctgtt cggttgaaaa agggtcaggt tatcggtgcc cgcgcggtga ttgacgggcg   3240
gggttatgcg gcaaattcag cactgagcgt gggcttccag gcgtttattg gccaggaatg   3300
gcgattgagc cacccgcatg gtttatcgtc tcccattatc atggatgcca cggtcgatca   3360
gcaaaatggt tatcgcttcg tgtacagcct gccgctctcg ccgaccagat tgttaattga   3420
agacacgcac tatattgata atgcgacatt agatcctgaa tgcgcgcggc aaaatatttg   3480
cgactatgcc gcgcaacagg gttggcagct tcagacactg ctgcgagaag aacagggcgc   3540
cttacccatt actctgtcgg gcaatgccga cgcattctgg cagcagcgcc ccctggcctg   3600
tagtggatta cgtgccggtc tgttccatcc taccaccggc tattcactgc cgctggcggt   3660
tgccgtggcc gaccgcctga gtgcacttga tgtctttacg tcggcctcaa ttcaccatgc   3720
cattacgcat tttgcccgcg agcgctggca gcagcagggc tttttccgca tgctgaatcg   3780
catgctgttt ttagccggac ccgccgattc acgctggcgg gttatgcagc gtttttatgg   3840
tttacctgaa gatttaattg cccgtttttta tgcgggaaaa ctcacgctga ccgatcggct   3900
acgtattctg agcggcaagc cgcctgttcc ggtattagca gcattgcaag ccattatgac   3960
gactcatcgt taaactagat aactagtagg aggattacaa atgagccatt tcgcggcgat   4020
cgcaccgcct ttttacagcc atgttcgcgc attacagaat ctcgctcagg aactggtcgc   4080
gcgcggtcat cgggtgacct ttattcagca atacgatatt aaacacttga tcgatagcga   4140
aaccattgga tttcattccg tcgggacaga cagccatccc cccggcgcgt taacgcgcgt   4200
gctacacctg gcggctcatc ctctggggcc gtcaatgctg aagctcatca atgaaatggc   4260
gcgcaccacc gatatgctgt gccgcgaact cccccaggca tttaacgatc tggccgtcga   4320
tggcgtcatt gttgatcaaa tggaaccggc aggcgcgctc gttgctgaag cactgggact   4380
```

gccgtttatc tctgtcgcct gcgcgctgcc tctcaatcgt gaaccggata tgcccctggc 4440
ggttatgcct ttcgaatacg ggaccagcga cgcggctcgc gaacgttatg ccgccagtga 4500
aaaaatttat gactggctaa tgcgtcgtca tgaccgtgtc attgccgaac acagccacag 4560
aatgggctta gcccccggc aaaagcttca ccagtgtttt tcgccactgg cgcaaatcag 4620
ccagcttgtt cctgaactgg attttccccg caaagcgtta ccggcttgtt ttcatgccgt 4680
cgggcctctg cgcgaaacgc acgcaccgtc aacgtcttca tcccgttatt ttacatcctc 4740
agaaaaaccc cggattttcg cctcgctggg cacgcttcag ggacaccgtt atgggctgtt 4800
taaaacgata gtgaaagcct gtgaagaaat tgacggtcag ctcctgttag cccactgtgg 4860
tcgtcttacg gactctcagt gtgaagagct ggcgcgaagc cgtcatacac aggtggtgga 4920
ttttgccgat cagtcagccg cgctgtctca ggcgcagctg gcgatcaccc acggcggcat 4980
gaatacggta ctggacgcga ttaattaccg gacgcccctt ttagcgcttc cgctggcctt 5040
tgatcagccc ggcgtcgcgt cacgcatcgt ttatcacggc atcggcaagc gtgcttcccg 5100
ctttaccacc agccatgctt tggctcgtca gatgcgttca ttgctgacca acgtcgactt 5160
tcagcagcgc atggcgaaaa tccagacagc ccttcgtttg gcagggggca ccatggccgc 5220
tgccgatatc attgagcagg ttatgtgcac cggtcagcct gtcttaagtg ggagcggcta 5280
tgcaaccgca ttatgatcta gtaggaggat tacaaaatga ccgcagctgt cgcagaacct 5340
cgcattgtac cgcgccaaac ctggatcggc ctgaccctgg cgggtatgat tgtggcgggc 5400
tggggttctc tgcacgtgta cggtgtgtac ttccaccgtt ggggcaccag cagcctggtt 5460
atcgtcccgg ctatcgtggc cgttcagacg tggttgtcgg ttggcctgtt tattgtcgca 5520
catgacgcca tgcacggttc cctggcccca ggccgtccgc gcctgaacgc agcggtgggt 5580
cgtctgacgc tgggtctgta tgcaggcttc cgtttcgatc gcttgaaaac ggcgcaccac 5640
gcgcatcatg cggctccggg taccgcagat gacccggact tttacgcgcc tgcgccacgc 5700
gccttcctgc cgtggttttt gaactttttc cgtacctatt tcggttggcg cgagatggcg 5760
gttctgaccg cgctggtcct gatcgcgctg tttggcttgg gtgcccgtcc ggcgaatctg 5820
ttgacttttt gggccgcacc ggcgctgctg agcgcgctgc aactgttcac gtttggcacc 5880
tggctgccgc accgtcacac ggaccagccg ttcgcggatg ctcatcatgc acgcagcagc 5940
ggttatggtc cggttctgag cctgctgacc tgctttcatt tcggtcgtca tcacgagcac 6000
cacctgacgc cgtggcgtcc gtggtggcgt ttgtggcgtg gtgaaagcta aatcgattca 6060
ctgtataaca ttaagaagga ggattacaaa atggcatggc tgacctggat cgcactgttc 6120
ctgaccgcat tcctgggtat ggaggctttc gcgtggatca tgcaccgtta tgtcatgcac 6180
ggtttcttgt ggtcgtggca tcgtagccat cacgagccgc acgaccaccc gctggaaaag 6240
aacgacctgt ttgccgttgt ctttgccgct ccggcgattg ttatggtggc ggtgggtctg 6300
cacctgtggc cttgggcctt gccggtcggt ctgggtatta ctgcgtacgg catggtttac 6360
ttcttctttc atgatggcct ggtgcatcgt cgtttcccga cgggctttag cggtcgcagc 6420
ggcttttgga cccgtcgcat ccaggcgcac cgtctgcacc atgcagtccg cacgcgtgag 6480
ggctgcgtgt cctttggctt cttgtgggtt cgcagcgcgc gtgccctgaa agcggaactg 6540
gcgcaaaaac gcggtagcag cagctctggt gcataaaagc tttatctagt tgctgatgcg 6600
gtattttctc cttacgcatc tgtgcggtat ttcacaccgc atatatggtg cactctcagt 6660
acaatctgct ctgatgccgc atagttaagc cagccccgac acccgccaac acccgctgac 6720

-continued

```
gcgccctgac gggcttgtct gctcccggca tccgcttaca gacaagctgt gaccgtctcc   6780
gggagctgca tgtgtcagag gttttcaccg tcatcaccga aacgcgcgag acgaaagggc   6840
ctcgtgatac gcctattttt ataggttaat gtcatgataa taatggtttc ttagacgtca   6900
ggtggcactt ttcggggaaa tgtgcgcgga acccctattt gtttattttt ctaaatacat   6960
tcaaatatgt atccgctcat gagacaataa ccctgataaa tgcttcaata atattgaaaa   7020
aggaagagta tgagtattca acatttccgt gtcgccctta ttcccttttt tgcggcattt   7080
tgccttcctg tttttgctca cccagaaacg ctggtgaaag taaaagatgc tgaagatcag   7140
ttgggtgcac gagtgggtta catcgaactg gatctcaaca gcggtaagat ccttgagagt   7200
tttcgccccg aagaacgttt tccaatgatg agcactttta aagttctgct atgtggcgcg   7260
gtattatccc gtattgacgc cgggcaagag caactcggtc gccgcataca ctattctcag   7320
aatgacttgg ttgagtactc accagtcaca gaaaagcatc ttacggatgg catgacagta   7380
agagaattat gcagtgctgc cataaccatg agtgataaca ctgcggccaa cttacttctg   7440
acaacgatcg gaggaccgaa ggagctaacc gcttttttgc acaacatggg ggatcatgta   7500
actcgccttg atcgttggga accggagctg aatgaagcca taccaaacga cgagcgtgac   7560
accacgatgc ctgtagcaat ggcaacaacg ttgcgcaaac tattaactgg cgaactactt   7620
actctagctt cccggcaaca attaatagac tggatggagg cggataaagt tgcaggacca   7680
cttctgcgct cggcccttcc ggctggctgg tttattgctg ataaatctgg agccggtgag   7740
cgtgggtctc gcggtatcat tgcagcactg gggccagatg gtaagccctc ccgtatcgta   7800
gttatctaca cgacggggag tcaggcaact atggatgaac gaaatagaca gatcgctgag   7860
ataggtgcct cactgattaa gcattggtaa ctgtcagacc aagtttactc atatatactt   7920
tagattgatt taaaacttca tttttaattt aaaaggatct aggtgaagat cctttttgat   7980
aatctcatga ccaaaatccc ttaacgtgag ttttcgttcc actgagcgtc agaccccgta   8040
gaaaagatca aaggatcttc ttgagatcct ttttttctgc gcgtaatctg ctgcttgcaa   8100
acaaaaaaac caccgctacc agcggtggtt tgtttgccgg atcaagagct accaactctt   8160
tttccgaagg taactggctt cagcagagcg cagataccaa atactgtcct tctagtgtag   8220
ccgtagttag gccaccactt caagaactct gtagcaccgc ctacatacct cgctctgcta   8280
atcctgttac cagtggctgc tgccagtggc gataagtcgt gtcttaccgg gttggactca   8340
agacgatagt taccggataa ggcgcagcgg tcgggctgaa cggggggttc gtgcacacag   8400
cccagcttgg agcgaacgac ctacaccgaa ctgagatacc tacagcgtga gctatgagaa   8460
agcgccacgc ttcccgaagg gagaaaggcg gacaggtatc cggtaagcgg cagggtcgga   8520
acaggagagc gcacgaggga gcttccaggg ggaaacgcct ggtatcttta tagtcctgtc   8580
gggtttcgcc acctctgact tgagcgtcga tttttgtgat gctcgtcagg ggggcggagc   8640
ctatggaaaa acgccagcaa cgcggccttt ttacggttcc tggccttttg ctggcctttt   8700
gctcacatgt tctttcctgc gttatcccct gattctgtgg ataaccgtat taccgccttt   8760
gagtgagctg ataccgctcg ccgcagccga acgaccgagc gcagcgagtc agtgagcgag   8820
gaagcggaag a                                                        8831
```

<210> SEQ ID NO 24
<211> LENGTH: 6689
<212> TYPE: DNA
<213> ORGANISM: Artificial
<220> FEATURE:
<223> OTHER INFORMATION: Designed plasmid DNA, pAC-hexPS

<400> SEQUENCE: 24
gaattccgga tgagcattca tcaggcgggc aagaatgtga ataaaggccg gataaaactt 60
gtgcttattt ttctttacgg tctttaaaaa ggccgtaata tccagctgaa cggtctggtt 120
ataggtacat tgagcaactg actgaaatgc ctcaaaatgt tctttacgat gccattggga 180
tatatcaacg gtggtatatc cagtgatttt tttctccatt ttagcttcct tagctcctga 240
aaatctcgat aactcaaaaa atacgcccgg tagtgatctt atttcattat ggtgaaagtt 300
ggaacctctt acgtgccgat caacgtctca ttttcgccaa aagttggccc agggcttccc 360
ggtatcaaca gggacaccag gatttattta ttctgcgaag tgatcttccg tcacaggtat 420
ttattcggcg caaagtgcgt cgggtgatgc tgccaactta ctgatttagt gtatgatggt 480
gtttttgagg tgctccagtg gcttctgttt ctatcagctg tccctcctgt tcagctactg 540
acggggtggt gcgtaacggc aaaagcaccg ccggacatca gcgctagcgg agtgtatact 600
ggcttactat gttggcactg atgagggtgt cagtgaagtg cttcatgtgg caggagaaaa 660
aaggctgcac cggtgcgtca gcagaatatg tgatacagga tatattccgc ttcctcgctc 720
actgactcgc tacgctcggt cgttcgactg cggcgagcgg aaatggctta cgaacggggc 780
ggagatttcc tggaagatgc caggaagata cttaacaggg aagtgagagg gccgcggcaa 840
agccgttttt ccataggctc cgcccccctg acaagcatca cgaaatctga cgctcaaatc 900
agtggtggcg aaacccgaca ggactataaa gataccaggc gtttcccctg gcggctccct 960
cgtgcgctct cctgttcctg cctttcggtt taccggtgtc attccgctgt tatggccgcg 1020
tttgtctcat tccacgcctg acactcagtt ccgggtaggc agttcgctcc aagctggact 1080
gtatgcacga accccccgtt cagtccgacc gctgcgcctt atccggtaac tatcgtcttg 1140
agtccaaccc ggaaagacat gcaaaagcac cactggcagc agccactggt aattgattta 1200
gaggagttag tcttgaagtc atgcgccggt taaggctaaa ctgaaaggac aagttttggt 1260
gactgcgctc ctccaagcca gttacctcgg ttcaaagagt tggtagctca gagaaccttc 1320
gaaaaaccgc cctgcaaggc ggttttttcg ttttcagagc aagagattac gcgcagacca 1380
aaacgatctc aagaagatca tcttattaat cagataaaat atttcaagat ttcagtgcaa 1440
tttatctctt caaatgtagc acctgaagtc agccccatac gatataagtt gtaattctca 1500
tgtttgacag cttatcatcg ataagcttta atgcggtagt ttatcacagt taaattgcta 1560
acgcagtcag gcaccgtgta tgaaatctaa caatgcgctc atcgtcatcc tcggcaccgt 1620
caccctggat gctgtaggca taggcttggt tatgccggta ctgccgggcc tcttgcggga 1680
tatcgtccat tccgacagca tcgccagtca ctatggcgtg ctgctagcgc tatatgcgtt 1740
gatgcaattt ctatgcgcac ccgttctcgg agcactgtcc gaccgctttg gccgccgccc 1800
agtcctgctc gcttcgctac ttggagccac tatcgactac gcgatcatgg cgaccacacc 1860
cgtcctgtgg atcccgtgga ggtttcccga ctggaaagcg ggcagtgagc gcaacgcaat 1920
taatgtgagt tagctcactc attaggcacc ccaggcttta cactttatgc ttccggctcg 1980
tatgttgtgt ggaattgtga gcggataaca atttcacaca ggaaacacat atggaattca 2040
ggaggtagat caatgcgtta tttacataaa attgaactag aattaaaccg acttacaagt 2100
cgatatccat ttttcaaaaa aattgcattt gatgctgaaa tcataaagct cgttgatgac 2160
ctaaatgtcg atgaaaatgt aaaatgtgcg attgttgcca ttgacacgag tatgcgtatg 2220
caggatttta tcaatgaaga taataaagac agttttgtac tatcaacgga tgttttgagt 2280

-continued

```
gctttatttt ataagtattt atcacagcca ttttatcagc atgatttttt agtactgacg   2340
gattgtgtaa gtcgtatcaa tgaattaaaa tcaataagag caacgattac agacgaaatt   2400
gctttgcata atattaataa acaaattcat tatatgttca tacaacctta tatgaacaat   2460
gagaaagtgg tgtcttatga gtaaacagtt aaatggacag gaaaaaagtg agcttgtaca   2520
taatgtattc cagaatgtat cgacaaagta tgaccgcctc aacgatatca taagttttaa   2580
tcagcataaa tcctggcgta aatatacgat gaaacagatg aatgttaaaa aagggtcgaa   2640
agcacttgat gtatgctgcg gtacaggcga ctggacaatt cagatggcac aggctgtcgg   2700
taaaaatggt catgttattg gtcttgattt cagtgagaat atgttaagtg ttgcacaagg   2760
aaaaacgaat catatacaaa atattgaatt aattcatggt aatgcgatgg aattaccatt   2820
tgaagataat atatttgatt atacaacgat tggttttggt ttacgtaact taccggatta   2880
taaaaaagga ttagaagaaa tgtatcgtgt attaaaacct ggcggcatga ttgttgtttt   2940
agaaacgagc catccaacaa tgccagtatt taaacaaggt tacaaattat atttcaaata   3000
cgttatgccc ctgtttggga aagtatttgc taagtctatg aaggaatata gctggttaca   3060
gcaaagtgct tttgaatttc ctgataagta cacgttagca cttttaatgg ctgaaactgg   3120
atttacacac attaaattta aaggttttac tggtggcgtg agtgcgatgc atcttgcata   3180
caagccgaaa gaaaaataga atggatgatt gctttgagtt ataaagcgtt tttaaaccca   3240
tatatcattg aagttgaaaa aaggttatat gagtgtattc agagtgattc tgaaacgata   3300
aacaaggcgg cacaccatat tttaagttca ggaggaaagc gcgtacgtcc gatgtttgta   3360
ttattaagtg gttttctgaa tgatacacaa aaggatgact tgattcgtac agcagtatct   3420
ctggagctcg ttcatatggc aagtctcgtt catgatgatt acatcgataa tagtgatatg   3480
cgtcgtggta atacttcggt tcatatagct tttgataaag acacagcaat tcgcacagga   3540
catttttat tagcacgtgc gttacaaaat attgcaacta tcaataattc gaaattccat   3600
caaattttta gtaaaacgat acttgaagtt tgttttggtg aatttgacca gatggcagat   3660
cgatttaatt atcctgtatc ctttactgca tatttaagac gtattaatcg taaaacagcg   3720
atactgatag aagcaagctg tcatttaggg gctctcagct cacagcttga tgaacaatct   3780
acatatcata taaaacaatt tgggcattgt attggaatga gttatcaaat tattgatgat   3840
attctcgatt acacgagtga cgaagcaaca ctcggtaaac ctgtcggtag cgatataaga   3900
aacggtcata ttacgtatcc gcttatggcc gctatcgcta atttgaaaga gcaagatgac   3960
gataaacttg aagcagttgt taaacattta acatcaacat cagatgatga agtgtatcaa   4020
tatattgttt cgcaagttaa acaatatgga attgaacctg cagaattgct gagcagaaaa   4080
tatggtgata aagcgaaata tcacttgagt caattacagg atagtaatat taaagattat   4140
ttagaagaaa tccacgaaaa aatgttaaaa cgtgtttatt aatctagact cgaggggccc   4200
ggcgcctgat gcggtatttt ctccttacgc atctgtgcgg tatttcacgt gcgctcgagg   4260
ggcccggcgc ctgatgcggt attttctcct tacgcatctg tgcggtattt cacggatcct   4320
ctacgccgga cgcatcgtgg ccggcatcac cggcgccaca ggtgcggttg ctggcgccta   4380
tatcgccgac atcaccgatg gggaagatcg ggctcgccac ttcgggctca tgagcgcttg   4440
tttcggcgtg ggtatggtgg caggccccgt ggccggggga ctgttgggcg ccatctcctt   4500
gcatgcacca ttccttgcgg cggcggtgct caacggcctc aacctactac tgggctgctt   4560
cctaatgcag gagtcgcata agggagagcg tcgaccgatg cccttgagag ccttcaaccc   4620
agtcagctcc ttccggtggg cgcggggcat gactatcgtc gccgcactta tgactgtctt   4680
```

```
ctttatcatg caactcgtag gacaggtgcc ggcagcgctc tgggtcattt tcggcgagga   4740
ccgctttcgc tggagcgcga cgatgatcgg cctgtcgctt gcggtattcg gaatcttgca   4800
cgccctcgct caagccttcg tcactggtcc cgccaccaaa cgtttcggcg agaagcaggc   4860
cattatcgcc ggcatggcgg ccgacgcgct gggctacgtc ttgctggcgt tcgcgacgcg   4920
aggctggatg gccttcccca ttatgattct tctcgcttcc ggcggcatcg ggatgcccgc   4980
gttgcaggcc atgctgtcca ggcaggtaga tgacgaccat cagggacagc ttcaaggatc   5040
gctcgcggct cttaccagcc taacttcgat cactggaccg ctgatcgtca cggcgattta   5100
tgccgcctcg gcgagcacat ggaacgggtt ggcatggatt gtaggcgccg ccctatacct   5160
tgtctgcctc cccgcgttgc gtcgcggtgc atggagccgg gccacctcga cctgaatgga   5220
agccggcggc acctcgctaa cggattcacc actccaagaa ttggagccaa tcaattcttg   5280
cggagaactg tgaatgcgca aaccaaccct tggcagaaca tatccatcgc gtccgccatc   5340
tccagcagcc gcacgcggcg catctcgggc agcgttgggt cctggccacg ggtgcgcatg   5400
atcgtgctcc tgtcgttgag gacccggcta ggctggcggg gttgccttac tggttagcag   5460
aatgaatcac cgatacgcga gcgaacgtga agcgactgct gctgcaaaac gtctgcgacc   5520
tgagcaacaa catgaatggt cttcggtttc cgtgtttcgt aaagtctgga aacgcggaag   5580
tcccctacgt gctgctgaag ttgcccgcaa cagagagtgg aaccaaccgg tgataccacg   5640
atactatgac tgagagtcaa cgccatgagc ggcctcattt cttattctga gttacaacag   5700
tccgcaccgc tgtccggtag ctccttccgg tgggcgcggg gcatgactat cgtcgccgca   5760
cttatgactg tcttctttat catgcaactc gtaggacagg tgccggcagc gcccaacagt   5820
cccccggcca cggggcctgc caccataccc acgccgaaac aagcgccctg caccattatg   5880
ttccggatct gcatcgcagg atgctgctgg ctaccctgtg gaacacctac atctgtatta   5940
acgaagcgct aaccgttttt atcaggctct gggaggcaga ataaatgatc atatcgtcaa   6000
ttattacctc cacggggaga gcctgagcaa actggcctca ggcatttgag aagcacacgg   6060
tcacactgct tccggtagtc aataaaccgg taaaccagca atagacataa gcggctattt   6120
aacgaccctg ccctgaaccg acgaccgggt cgaatttgct ttcgaatttc tgccattcat   6180
ccgcttatta tcacttattc aggcgtagca ccaggcgttt aagggcacca ataactgcct   6240
taaaaaaatt acgccccgcc ctgccactca tcgcagtact gttgtaattc attaagcatt   6300
ctgccgacat ggaagccatc acagacggca tgatgaacct gaatcgccag cggcatcagc   6360
accttgtcgc cttgcgtata atatttgccc atggtgaaaa cgggggcgaa gaagttgtcc   6420
atattggcca cgtttaaatc aaaactggtg aaactcaccc agggattggc tgagacgaaa   6480
aacatattct caataaaccc tttagggaaa taggccaggt tttcaccgta acacgccaca   6540
tcttgcgaat atatgtgtag aaactgccgg aaatcgtcgt ggtattcact ccagagcgat   6600
gaaaacgttt cagtttgctc atggaaaacg gtgtaacaag ggtgaacact atcccatatc   6660
accagctcac cgtctttcat tgccatacg                                    6689
```

<210> SEQ ID NO 25
<211> LENGTH: 6249
<212> TYPE: DNA
<213> ORGANISM: Artificial
<220> FEATURE:
<223> OTHER INFORMATION: Designed plasmid DNA, pAC-FDSI78G,Y81A-idi

<400> SEQUENCE: 25

-continued

```
gaattccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttggccc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttccccctg gcggctccct    960
cgtgcgctct cctgttcctg cctttcggtt taccggtgtc attccgctgt tatggccgcg   1020
tttgtctcat tccacgcctg acactcagtt ccgggtaggc agttcgctcc aagctggact   1080
gtatgcacga accccccgtt cagtccgacc gctgcgcctt atccggtaac tatcgtcttg   1140
agtccaaccc ggaaagacat gcaaaagcac cactggcagc agccactggt aattgattta   1200
gaggagttag tcttgaagtc atgcgccggt taaggctaaa ctgaaaggac aagttttggt   1260
gactgcgctc ctccaagcca gttacctcgg ttcaaagagt tggtagctca gagaaccttc   1320
gaaaaaccgc cctgcaaggc ggttttttcg ttttcagagc aagagattac gcgcagacca   1380
aaacgatctc aagaagatca tcttattaat cagataaaat atttcaagat ttcagtgcaa   1440
tttatctctt caaatgtagc acctgaagtc agccccatac gatataagtt gtaattctca   1500
tgtttgacag cttatcgtga ggtttcccga ctggaaagcg ggcagtgagc gcaacgcaat   1560
taatgtgagt tagctcactc attaggcacc ccaggcttta cactttatgc ttccggctcg   1620
tatgttgtgt ggaattgtga gcggataaca atttcacaca ggaaacacat atggaattct   1680
ctagaaggag gattacaaaa tgcaaacgga acacgtcatt ttattgaatg cacagggagt   1740
tcccacgggt acgctggaaa agtatgccgc acacacggca gacacccgct tacatctcgc   1800
gttctccagt tggctgttta atgccaaagg acaattatta gttacccgcc gcgcactgag   1860
caaaaaagca tggcctggcg tgtggactaa ctcggtttgt gggcacccac aactgggaga   1920
aagcaacgaa gacgcagtga tccgccgttg ccgttatgag cttggcgtgg aaattacgcc   1980
tcctgaatct atctatcctg actttcgcta ccgcgccacc gatccgagtg gcattgtgga   2040
aaatgaagtg tgtccggtat ttgccgcacg caccactagt gcgttacaga tcaatgatga   2100
tgaagtgatg gattatcaat ggtgtgattt agcagatgta ttacacggta ttgatgccac   2160
gccgtgggcg ttcagtccgt ggatggtgat gcaggcgaca aatcgcgaag ccagaaaacg   2220
attatctgca tttacccagc ttaaataact cgaggggccc ggcgcctgat gcggtatttt   2280
ctccttacgc atctgtgcgg tatttcactg catcgataag ctttaatgcg gtagtttatc   2340
acagttaaat tgctaacgca gtcaggcacc gtgtatgaaa tctaacaatg cgctcatcgt   2400
```

-continued

```
catcctcggc accgtcaccc tggatgctgt aggcataggc ttggttatgc cggtactgcc   2460
gggcctcttg cgggatatcg tccattccga cagcatcgcc agtcactatg gcgtgctgct   2520
agcgctatat gcgttgatgc aatttctatg cgcacccgtt ctcggagcac tgtccgaccg   2580
ctttggccgc cgcccagtcc tgctcgcttc gctacttgga gccactatcg actacgcgat   2640
catggcgacc acacccgtcc tgtggatccc gtggaggttt cccgactgga aagcgggcag   2700
tgagcgcaac gcaattaatg tgagttagct cactcattag gcaccccagg ctttacactt   2760
tatgcttccg gctcgtatgt tgtgtggaat tgtgagcgga taacaatttc acacaggaaa   2820
cacatatgga attctctaga aggaggagta agcgatggcg cagctttcag ttgaacagtt   2880
tctcaacgag caaaaacagg cggtggaaac agcgctctcc cgttatatag agcgcttaga   2940
agggccggcg aagctgaaaa aggcgatggc gtactcattg gaggccggcg gcaaacgaat   3000
ccgtccgttg ctgcttctgt ccaccgttcg ggcgctcggc aaagacccgg cggtcggatt   3060
gcccgtcgcc tgcgcgattg aaatgggtca tacggcatct ttgatccatg atgatttgcc   3120
gagcatggac aacgatgatt tgcggcgcgg caagccgacg aaccataaag tgttcggcga   3180
ggcgatggcc atcttggcgg gggacgggtt gttgacgtac gcgtttcaat tgatcaccga   3240
aatcgacgat gagcgcatcc ctccttccgt ccggcttcgg ctcatcgaac ggctggcgaa   3300
agcggccggt ccggaaggga tggtcgccgg tcaggcagcc gatatggaag gagaggggaa   3360
aacgctgacg ctttcggagc tcgaatacat tcatcggcat aaaaccggga aaatgctgca   3420
atacagcgtg cacgccggcg ccttgatcgg cggcgctgat gcccggcaaa cgcgggagct   3480
tgacgaattc gccgcccatc taggccttgc ctttcaaatt cgcgatgata ttctcgatat   3540
tgaaggggca gaagaaaaaa tcggcaagcc ggtcggcagc gaccaaagca acaacaaagc   3600
gacgtatcca gcgttgctgt cgcttgccgg cgcgaaggaa aagttggcgt tccatatcga   3660
ggcggcgcag cgccatttac ggaacgctga cgttgacggc gccgcgctcg cctatatttg   3720
cgaactggtc gccgcccgcg accattaact cgaggggccc ggcgcctgat gcggtatttt   3780
ctccttacgc atctgtgcgg tatttcacgt gcgctcgagg ggcccggcgc ctgatgcggt   3840
attttctcct tacgcatctg tgcggtattt cacggatcct ctacgccgga cgcatcgtgg   3900
ccggcatcac cggcgccaca ggtgcggttg ctggcgccta tatcgccgac atcaccgatg   3960
gggaagatcg ggctcgccac ttcgggctca tgagcgcttg tttcggcgtg ggtatggtgg   4020
caggccccgt ggccggggga ctgttgggcg ccatctcctt gcatgcacca ttccttgcgg   4080
cggcggtgct caacggcctc aacctactac tgggctgctt cctaatgcag gagtcgcata   4140
agggagagcg tcgaccgatg cccttgagag ccttcaaccc agtcagctcc ttccggtggg   4200
cgcggggcat gactatcgtc gccgcactta tgactgtctt ctttatcatg caactcgtag   4260
gacaggtgcc ggcagcgctc tgggtcattt tcggcgagga ccgctttcgc tggagcgcga   4320
cgatgatcgg cctgtcgctt gcggtattcg gaatcttgca cgccctcgct caagccttcg   4380
tcactggtcc cgccaccaaa cgtttcggcg agaagcaggc cattatcgcc ggcatggcgg   4440
ccgacgcgct gggctacgtc ttgctggcgt tcgcgacgcg aggctggatg gccttcccca   4500
ttatgattct tctcgcttcc ggcggcatcg ggatgcccgc gttgcaggcc atgctgtcca   4560
ggcaggtaga tgacgaccat cagggacagc ttcaaggatc gctcgcggct cttaccagcc   4620
taacttcgat cactggaccg ctgatcgtca cggcgattta tgccgcctcg gcgagcacat   4680
ggaacgggtt ggcatggatt gtaggcgccg ccctatacct tgtctgcctc cccgcgttgc   4740
```

-continued

```
gtcgcggtgc atggagccgg gccacctcga cctgaatgga agccggcggc acctcgctaa   4800

cggattcacc actccaagaa ttggagccaa tcaattcttg cggagaactg tgaatgcgca   4860

aaccaaccct tggcagaaca tatccatcgc gtccgccatc tccagcagcc gcacgcggcg   4920

catctcgggc agcgttgggt cctggccacg ggtgcgcatg atcgtgctcc tgtcgttgag   4980

gacccggcta ggctggcggg gttgccttac tggttagcag aatgaatcac cgatacgcga   5040

gcgaacgtga agcgactgct gctgcaaaac gtctgcgacc tgagcaacaa catgaatggt   5100

cttcggtttc cgtgtttcgt aaagtctgga aacgcggaag tcccctacgt gctgctgaag   5160

ttgcccgcaa cagagagtgg aaccaaccgg tgataccacg atactatgac tgagagtcaa   5220

cgccatgagc ggcctcattt cttattctga gttacaacag tccgcaccgc tgtccggtag   5280

ctccttccgg tgggcgcggg gcatgactat cgtcgccgca cttatgactg tcttctttat   5340

catgcaactc gtaggacagg tgccggcagc gcccaacagt cccccggcca cggggcctgc   5400

caccataccc acgccgaaac aagcgccctg caccattatg ttccggatct gcatcgcagg   5460

atgctgctgg ctaccctgtg gaacacctac atctgtatta acgaagcgct aaccgttttt   5520

atcaggctct gggaggcaga ataaatgatc atatcgtcaa ttattacctc cacggggaga   5580

gcctgagcaa actggcctca ggcatttgag aagcacacgg tcacactgct tccggtagtc   5640

aataaaccgg taaaccagca atagacataa gcggctattt aacgaccctg ccctgaaccg   5700

acgaccgggt cgaatttgct ttcgaatttc tgccattcat ccgcttatta tcacttattc   5760

aggcgtagca ccaggcgttt aagggcacca ataactgcct taaaaaaatt acgccccgcc   5820

ctgccactca tcgcagtact gttgtaattc attaagcatt ctgccgacat ggaagccatc   5880

acagacggca tgatgaacct gaatcgccag cggcatcagc accttgtcgc cttgcgtata   5940

atatttgccc atggtgaaaa cgggggcgaa gaagttgtcc atattggcca cgtttaaatc   6000

aaaactggtg aaactcaccc agggattggc tgagacgaaa aacatattct caataaaccc   6060

tttagggaaa taggccaggt tttcaccgta acacgccaca tcttgcgaat atatgtgtag   6120

aaactgccgg aaatcgtcgt ggtattcact ccagagcgat gaaaacgttt cagtttgctc   6180

atggaaaacg gtgtaacaag ggtgaacact atcccatatc accagctcac cgtctttcat   6240

tgccatacg                                                           6249
```

```
<210> SEQ ID NO 26
<211> LENGTH: 3364
<212> TYPE: DNA
<213> ORGANISM: Artificial
<220> FEATURE:
<223> OTHER INFORMATION: Designed plasmid DNA, pUC-CrtMF26A,W38A,F233S

<400> SEQUENCE: 26

ttggccgatt cattaatgca gctggcacga caggtttccc gactggaaag cgggcagtga     60

gcgcaacgca attaatgtga gttagctcac tcattaggca ccccaggctt tacactttat    120

gcttccggct cgtatgttgt gtggaattgt gagcggataa caatttcaca caggaaacac    180

atatggaatt ctctagaagg aggattacaa aatgacaatg atgaatatga attttaaata    240

ttgtcataaa atcatgaaga aacattcaaa aagcttttct tacgctgcgg acttgttacc    300

agaagatcaa agaaaagcgg ttgcggcaat ttatgctgtg tgtcgtaaaa ttgatgacag    360

tatagatgtt tatggcgata ttcaattttt aaatcaaata aaagaagata tacaatctat    420

tgaaaaatac ccatatgaac atcatcactt tcaaagtgat cgtagaatca tgatggcgct    480

tcagcatgtt gcacaacata aaaatatcgc ctttcaatct tttataatc tcattgatac     540
```

```
tgtatataaa gatcaacatt ttacaatgtt tgaaacggac gctgaattat tcggatattg    600
ttatggtgtt gctggtacag taggtgaagt attgacgccg attttaagtg atcatgaaac    660
acatcagaca tacgatgtcg caagaagact tggtgaatcg ttgcaattga ttaatatatt    720
aagagatgtc ggtgaagatt ttgacaatga acggatatat tttagtaagc aacgattaaa    780
gcaatatgaa gttgatattg ctgaagtgta ccaaaatggt gttaataatc attatattga    840
cttatgggaa tattatgcag ctatcgcaga aaaagatttt caagatgtta tggatcaaat    900
caaagtatct agtattgaag cacaaccaat catagaatta gcagcacgta tatatattga    960
aatactggac gaagtgagac aggctaacta tacattacat gaacgtgttt ttgtggataa   1020
gaggaaaaag gcaaagttgt ttcatgaaat aaatagtaaa tatcatagaa tatagctcga   1080
ggggcccggc gcctgatgcg gtattttctc cttacgcatc tgtgcggtat ttcacaccgc   1140
atatatggtg cactctcagt acaatctgct ctgatgccgc atagttaagc cagccccgac   1200
acccgccaac acccgctgac gcgccctgac gggcttgtct gctcccggca tccgcttaca   1260
gacaagctgt gaccgtctcc gggagctgca tgtgtcagag gttttcaccg tcatcaccga   1320
aacgcgcgag acgaaagggc ctcgtgatac gcctattttt ataggttaat gtcatgataa   1380
taatggtttc ttagacgtca ggtggcactt ttcggggaaa tgtgcgcgga acccctattt   1440
gtttattttt ctaaatacat tcaaatatgt atccgctcat gagacaataa ccctgataaa   1500
tgcttcaata atattgaaaa aggaagagta tgagtattca acatttccgt gtcgccctta   1560
ttcccttttt tgcggcattt tgccttcctg tttttgctca cccagaaacg ctggtgaaag   1620
taaaagatgc tgaagatcag ttgggtgcac gagtgggtta catcgaactg gatctcaaca   1680
gcggtaagat ccttgagagt tttcgccccg aagaacgttt tccaatgatg agcactttta   1740
aagttctgct atgtggcgcg gtattatccc gtattgacgc cgggcaagag caactcggtc   1800
gccgcataca ctattctcag aatgacttgg ttgagtactc accagtcaca gaaaagcatc   1860
ttacggatgg catgacagta agagaattat gcagtgctgc cataaccatg agtgataaca   1920
ctgcggccaa cttacttctg acaacgatcg gaggaccgaa ggagctaacc gcttttttgc   1980
acaacatggg ggatcatgta actcgccttg atcgttggga accggagctg aatgaagcca   2040
taccaaacga cgagcgtgac accacgatgc ctgtagcaat ggcaacaacg ttgcgcaaac   2100
tattaactgg cgaactactt actctagctt cccggcaaca attaatagac tggatggagg   2160
cggataaagt tgcaggacca cttctgcgct cggcccttcc ggctggctgg tttattgctg   2220
ataaatctgg agccggtgag cgtgggtctc gcggtatcat tgcagcactg gggccagatg   2280
gtaagccctc ccgtatcgta gttatctaca cgacggggag tcaggcaact atggatgaac   2340
gaaatagaca gatcgctgag ataggtgcct cactgattaa gcattggtaa ctgtcagacc   2400
aagtttactc atatatactt tagattgatt taaaacttca tttttaattt aaaaggatct   2460
aggtgaagat cctttttgat aatctcatga ccaaaatccc ttaacgtgag ttttcgttcc   2520
actgagcgtc agaccccgta gaaaagatca aaggatcttc ttgagatcct ttttttctgc   2580
gcgtaatctg ctgcttgcaa acaaaaaaac caccgctacc agcggtggtt tgtttgccgg   2640
atcaagagct accaactctt tttccgaagg taactggctt cagcagagcg cagataccaa   2700
atactgtcct tctagtgtag ccgtagttag gccaccactt caagaactct gtagcaccgc   2760
ctacatacct cgctctgcta atcctgttac cagtggctgc tgccagtggc gataagtcgt   2820
gtcttaccgg gttggactca agacgatagt taccggataa ggcgcagcgg tcgggctgaa   2880
```

-continued

```
cggggggttc gtgcacacag cccagcttgg agcgaacgac ctacaccgaa ctgagatacc   2940

tacagcgtga gctatgagaa agcgccacgc ttcccgaagg gagaaaggcg gacaggtatc   3000

cggtaagcgg cagggtcgga acaggagagc gcacgaggga gcttccaggg ggaaacgcct   3060

ggtatcttta tagtcctgtc gggtttcgcc acctctgact tgagcgtcga tttttgtgat   3120

gctcgtcagg ggggcggagc ctatggaaaa acgccagcaa cgcggccttt ttacggttcc   3180

tggccttttg ctggcctttt gctcacatgt tctttcctgc gttatcccct gattctgtgg   3240

ataaccgtat taccgccttt gagtgagctg ataccgctcg ccgcagccga acgaccgagc   3300

gcagcgagtc agtgagcgag gaagcggaag agcgcccaat acgcaaaccg cctctccccg   3360

cgcg                                                                3364
```

<210> SEQ ID NO 27
<211> LENGTH: 492
<212> TYPE: PRT
<213> ORGANISM: Artificial
<220> FEATURE:
<223> OTHER INFORMATION: Pantoea ananatis crtI mutant (N304P)

<400> SEQUENCE: 27

```
Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Leu Glu Gln
            20                  25                  30

Arg Asp Lys Pro Gly Gly Arg Ala Tyr Val Tyr Glu Asp Gln Gly Phe
        35                  40                  45

Thr Phe Asp Ala Gly Pro Thr Val Ile Thr Asp Pro Ser Ala Ile Glu
    50                  55                  60

Glu Leu Phe Ala Leu Ala Gly Lys Gln Leu Lys Glu Tyr Val Glu Leu
65                  70                  75                  80

Leu Pro Val Thr Pro Phe Tyr Arg Leu Cys Trp Glu Ser Gly Lys Val
                85                  90                  95

Phe Asn Tyr Asp Asn Asp Gln Thr Arg Leu Glu Ala Gln Ile Gln Gln
            100                 105                 110

Phe Asn Pro Arg Asp Val Glu Gly Tyr Arg Gln Phe Leu Asp Tyr Ser
        115                 120                 125

Arg Ala Val Phe Lys Glu Gly Tyr Leu Lys Leu Gly Thr Val Pro Phe
    130                 135                 140

Leu Ser Phe Arg Asp Met Leu Arg Ala Ala Pro Gln Leu Ala Lys Leu
145                 150                 155                 160

Gln Ala Trp Arg Ser Val Tyr Ser Lys Val Ala Ser Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
    210                 215                 220

Gln Gly Met Ile Lys Leu Phe Gln Asp Leu Gly Gly Glu Val Val Leu
225                 230                 235                 240

Asn Ala Arg Val Ser His Met Glu Thr Thr Gly Asn Lys Ile Glu Ala
                245                 250                 255

Val His Leu Glu Asp Gly Arg Arg Phe Leu Thr Gln Ala Val Ala Ser
            260                 265                 270
```

-continued

```
Asn Ala Asp Val Val His Thr Tyr Arg Asp Leu Leu Ser Gln His Pro
        275                 280                 285

Ala Ala Val Lys Gln Ser Asn Lys Leu Gln Thr Lys Arg Met Ser Pro
    290                 295                 300

Ser Leu Phe Val Leu Tyr Phe Gly Leu Asn His His His Asp Gln Leu
305                 310                 315                 320

Ala His His Thr Val Cys Phe Gly Pro Arg Tyr Arg Glu Leu Ile Asp
                325                 330                 335

Glu Ile Phe Asn His Asp Gly Leu Ala Glu Asp Phe Ser Leu Tyr Leu
            340                 345                 350

His Ala Pro Cys Val Thr Asp Ser Ser Leu Ala Pro Glu Gly Cys Gly
        355                 360                 365

Ser Tyr Tyr Val Leu Ala Pro Val Pro His Leu Gly Thr Ala Asn Leu
    370                 375                 380

Asp Trp Thr Val Glu Gly Pro Lys Leu Arg Asp Arg Ile Phe Ala Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Gln Leu Asn Ala Tyr His
            420                 425                 430

Gly Ser Ala Phe Ser Val Glu Pro Val Leu Thr Gln Ser Ala Trp Phe
        435                 440                 445

Arg Pro His Asn Arg Asp Lys Thr Ile Thr Asn Leu Tyr Leu Val Gly
    450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490
```

<210> SEQ ID NO 28
<211> LENGTH: 1479
<212> TYPE: DNA
<213> ORGANISM: Artificial
<220> FEATURE:
<223> OTHER INFORMATION: Pantoea ananatis crtI mutant (N304P)

<400> SEQUENCE: 28

```
atgaaaccaa ctacggtaat tggtgcaggc ttcggtggcc tggcactggc aattcgtcta     60

caagctgcgg ggatccccgt cttactgctt gaacaacgtg ataaacccgg cggtcgggct    120

tatgtctacg aggatcaggg gtttaccttt gatgcaggcc cgacggttat caccgatccc    180

agtgccattg aagaactgtt tgcactggca ggaaaacagt taaaagagta tgtcgaactg    240

ctgccggtta cgccgtttta ccgcctgtgt tgggagtcag ggaaggtctt taattacgat    300

aacgatcaaa cccggctcga agcgcagatt cagcagttta atccccgcga tgtcgaaggt    360

tatcgtcagt ttctggacta ttcacgcgcg gtgtttaaag aaggctatct aaagctcggt    420

actgtccctt ttttatcgtt cagagacatg cttcgcgccg cacctcaact ggcgaaactg    480

caggcatgga gaagcgttta cagtaaggtt gccagttaca tcgaagatga acatctgcgc    540

caggcgtttt ctttccactc gctgttggtg ggcggcaatc ccttcgccac ctcatccatt    600

tatacgttga tacacgcgct ggagcgtgag tggggcgtct ggtttccgcg tggcggcacc    660

ggcgcattag ttcaggggat gataaagctg tttcaggatc tgggtggcga agtcgtgtta    720

aacgccagag tcagccatat ggaaacgaca ggaaacaaga ttgaagccgt gcatttagag    780

gacggtcgca ggttcctgac gcaagccgtc gcgtcaaatg cagatgtggt tcatacctat    840
```

-continued

```
cgcgacctgt taagccagca ccctgccgcg gttaagcagt ccaacaaact gcagactaag    900

cgcatgagtc cttctctgtt tgtgctctat tttggtttga atcaccatca tgatcagctc    960

gcgcatcaca cggtttgttt cggcccgcgt taccgcgagc tgattgacga aatttttaat   1020

catgatggcc tcgcagagga cttctcactt tatctgcacg cgccctgtgt cacggattcg   1080

tcactggcgc ctgaaggttg cggcagttac tatgtgttgg cgccggtgcc acatttaggc   1140

accgcgaacc tcgactggac ggttgagggg ccaaaactac gcgaccgtat ttttgcgtac   1200

cttgagcagc attacatgcc tggcttacgg agtcagctgg tcacgcaccg gatgtttacg   1260

ccgtttgatt ttcgcgacca gcttaatgcc tatcatggct cagccttttc tgtggagccc   1320

gttcttaccc agagcgcctg gtttcggccg cataaccgcg ataaaaccat tactaatctc   1380

tacctggtcg gcgcaggcac gcatcccggc gcaggcattc ctggcgtcat cggctcggca   1440

aaagcgacag caggtttgat gctggaggat ctgatttga                          1479
```

METHOD FOR PRODUCING CAROTENOIDS EACH HAVING 50 CARBON ATOMS

This application is a National Stage Application of PCT/JP2012/064817, filed Jun. 8, 2012, which claims priority from Japanese Patent Application No. 2011-130326, filed Jun. 10, 2011.

TECHNICAL FIELD

The present invention relates to a production method for a carotenoid having 50 carbon atoms, including the step of culturing, in a medium, a cell transformed with a mutant phytoene desaturase gene.

BACKGROUND ART

There exist various carotenoids in nature. Approximately 750 kinds of carotenoids have been identified heretofore, and many of the carotenoids have been shown to have useful physiological functions and industrial applicability such as an antioxidant activity or an antitumor activity, or a use as a functional pigment molecule. In general, carotenoids are compounds classified as tetraterpenes formed of an isoprene backbone of 30 or 40 carbon atoms. In nature, a linear backbone of 30 or 40 carbon atoms is formed as a basic backbone and then subjected to various modifications such as cyclization. Structural diversity of the carotenoids is attributed to diversity of such modifications. Further, carotenoids are known to have physiological activities greatly varying depending on structural differences based on the diversity of the modifications.

A large number of carotenoids have been obtained by isolation and extraction from nature such as plants, or by chemical synthesis. Recently, however, production utilizing microbial fermentation has also been performed. In order to establish biosynthetic pathways for rare carotenoids, which exist in nature in only trace amounts, and unnatural carotenoids, which do not exist in nature, research has been made by many researchers (Non Patent Literatures 1 to 8 and Patent Literature 1). In Non Patent Literatures 1 to 6, carotenoids having various structures have been obtained by synthesis based on the so-called combinatorial biosynthesis technique. The combinatorial biosynthesis is a technology involving altering biosynthetic pathways of microorganisms using a genetic engineering technique and allowing the microorganisms to produce a compound of interest. Modifying enzymes that provide various structures to carotenoids have the "locally specific" nature of recognizing and acting on only part of substrates. Based on such nature of the modified substrates, the combinatorial biosynthesis of the carotenoids has been performed (Non Patent Literature 9). Meanwhile, in Non Patent Literatures 7, 8, and 11 and Patent Literature 1, biosynthesis of various unnatural carotenoids has been achieved by a method involving constructing a metabolic pathway using an activity of an enzyme that cannot be found in nature and is created using protein engineering.

As described above, the carotenoids that exist in nature have backbones of 30 carbon atoms and 40 carbon atoms. The former is derived from 4,4'-diapophytoene, which is synthesized via head-to-head condensation of two molecules of farnesyl diphosphate ($C_{15}PP$). The latter is derived from phytoene (carotenoid backbone compound of 40 carbon atoms), which is synthesized via head-to-head condensation of two molecules of geranylgeranyl diphosphate ($C_{20}PP$). The former is a key component of biosynthetic pathways for 10-odd kinds of carotenoids known to exist in nature, and the latter is a key component of biosynthetic pathways for about 700 or more kinds of carotenoids.

Further, there is a report that a carotenoid having a backbone of 50 carbon atoms, which is larger than that of 40 carbon atoms, exists in nature (Patent Literature 2). The carotenoid having a backbone of 50 carbon atoms is synthesized by binding an isoprene unit to a carotenoid having 40 carbon atoms "as addition" so as to increase the total number of carbon atoms to 45 and 50 (Non Patent Literature 10). In a synthetic pathway for a backbone of 40 or more carbon atoms, such as a backbone of 50 carbon atoms or 60 carbon atoms, synthesis is performed by using, for example, geranylfarnesyl diphosphate ($C_{25}PP$) or hexaprenyl diphosphate ($C_{30}PP$) as a raw material. Although the carotenoid having a backbone of 40 or more carbon atoms is expected to have many potentialities for physiological and pigment functions and the like different from conventional ones, there is no detailed report on its synthetic pathways in nature, and there are few reports on its artificial biosynthetic pathways.

Dr. Umeno, one of the inventors of the present invention, developed an enzyme having a function of synthesizing a carotenoid backbone compound of 50 carbon atoms via condensation of two molecules of geranylfarnesyl diphosphate ($C_{25}PP$) by altering a synthase (CrtM) for a carotenoid having 30 carbon atoms derived from *Staphylococcus aureus*. In addition, Dr. Umeno succeeded for the first time in the world in co-expressing the enzyme with an appropriate precursor synthase in *Escherichia coli* to produce 16,16'-diisopentenylphytoene, a carotenoid backbone compound of 50 carbon atoms (Non Patent Literature 7). However, in the synthetic pathway in Non Patent Literature 7, carotenoids having backbones of, for example, 30 carbon atoms, 40 carbon atoms, and 45 carbon atoms were synthesized simultaneously with that having a backbone of 50 carbon atoms. Even when a wild-type phytoene desaturase was added in this pathway, about 75% of the carotenoid backbone compound of 50 carbon atoms still remained without being desaturated, resulting in poor synthetic efficiency (Non Patent Literature 8).

CITATION LIST

Patent Literature

[PTL 1] US 2002/0051998 A

[PTL 2] JP 07-132096 A

Non Patent Literature

[NPL 1] Takaichi S. et al., Eur J Biochem 241, 291-6 (1996)

[NPL 2] Yokoyama A. et al., Tetrahedron Lett. 39, 3709-12 (1998)

[NPL 3] Albrecht M. et al., Nat. Biotechnol. 18, 843-6 (2000)

[NPL 4] Lee P. C. et al., Chem. Biol. 10, 453-462 (2003)

[NPL 5] Mijts B. N. et al., Chem. Biol. 12, 453-460 (2005)

[NPL 6] Umeno D. et al., Appl Environ Microbiol 69, 3573-3579 (2003)

[NPL 7] Umeno D. et al., J Bacteriol, 186, 1531-1536 (2004)

[NPL 8] Tobias A. V. et al., Biochim Biophys Acta, 1761, 235-246 (2006)

[NPL 9] Umeno D. et al., Microbiol Mol Biol Rev 69, 51-78 (2005)

[NPL 10] Krubasik P. et al., Eur J Biochem 268, 3702-3708 (2001)

[NPL 11] Schmidt-Dannert C. et al., Nature Biotech. 18, 750-753 (2000)

SUMMARY OF INVENTION

Technical Problem

A carotenoid having 50 carbon atoms has a large backbone as compared to a carotenoid having 40 carbon atoms, and hence has such superiority as a substance that conjugated double bonds having a large size can be accommodated. It is considered that, when a carotenoid backbone compound of 50 carbon atoms can be synthesized and desaturated as in the synthetic pathway for the carotenoid having 40 carbon atoms in nature, the resultant product can be used in combination with various modifying enzymes to produce carotenoids having 50 carbon atoms having a great variety of structures and physiological activities. An object of the present invention is to provide a production method for various carotenoids having 50 carbon atoms, including efficiently desaturating a carotenoid backbone compound of 50 carbon atoms.

Solution to Problem

The inventors of the present invention have made intensive studies in order to achieve the object. Consequently, the inventors have found that a carotenoid backbone compound of 50 carbon atoms can be efficiently desaturated with a mutant phytoene desaturase obtained by introducing a mutation into a phytoene desaturase (CrtI), and have focused attention on the fact that a carotenoid having 50 carbon atoms can be efficiently and simply synthesized by culturing a cell having introduced therein a mutant phytoene desaturase gene, thus achieving the present invention.

That is, the present invention relates to the following items.

1. A method of producing a carotenoid having 50 carbon atoms, comprising: culturing, in a medium, a cell transformed with a mutant phytoene desaturase gene; and obtaining the carotenoid having 50 carbon atoms from a culture after the culturing, wherein the mutant phytoene desaturase gene has an introduced mutation to encode a mutant phytoene desaturase having an enhanced activity to desaturate a carotenoid backbone compound of 50 carbon atoms.

2. The method of producing a carotenoid having 50 carbon atoms according to the above-described item 1, wherein the mutant phytoene desaturase gene has an introduced mutation to encode a mutant phytoene desaturase having an enhanced activity to desaturate a carotenoid backbone compound of 50 carbon atoms has been introduced, and the mutation causes a substitution of an amino acid corresponding to at least one amino acid selected from asparagine at position 304, phenylalanine at position 339, isoleucine at position 338, aspartic acid at position 395, and isoleucine at position 228 in an amino acid sequence set forth in SEQ ID NO: 1.

3. The method of producing a carotenoid having 50 carbon atoms according to the above-described item 1 or 2, wherein the mutant phytoene desaturase gene has an introduced mutation to encode a mutant phytoene desaturase having an enhanced activity to desaturate a carotenoid backbone compound of 50 carbon atoms has been introduced, and the mutation causes at least a substitution of an amino acid corresponding to asparagine at position 304 in SEQ ID NO: 1 by proline or serine.

4. The method of producing a carotenoid having 50 carbon atoms according to any one of the above-described items 1 to 3, wherein the mutant phytoene desaturase gene has an introduced mutation to encode a mutant phytoene desaturase having an enhanced activity to desaturate a carotenoid backbone compound of 50 carbon atoms has been introduced, and the mutant phytoene desaturase gene is obtained by introducing the mutation into a phytoene desaturase gene derived from *Pantoea ananatis*.

5. The method of producing a carotenoid having 50 carbon atoms according to any one of the above-described items 1 to 4, wherein the cell is *Escherichia coli* or yeast.

6. The method of producing a carotenoid having 50 carbon atoms according to any one of the above-described items 1 to 5, wherein the cell transformed with the mutant phytoene desaturase gene is further transformed with a gene encoding an enzyme that synthesizes the carotenoid backbone compound of 50 carbon atoms via condensation of two molecules of geranylfarnesyl diphosphate.

7. The method of producing a carotenoid having 50 carbon atoms according to any one of the above-described items 1 to 6, wherein the cell as defined in any one of the above-described items 1 to 6 is further transformed with a gene encoding an enzyme that synthesizes geranylfarnesyl diphosphate from farnesyl diphosphate and/or geranylgeranyl diphosphate.

8. The method of producing a carotenoid having 50 carbon atoms according to any one of the above-described items 1 to 7, wherein the cell as defined in any one of the above-described items 1 to 7 is further transformed with a gene encoding an enzyme that cyclizes ends of a desaturated carotenoid having 50 carbon atoms obtained by desaturating the carotenoid backbone compound of 50 carbon atoms.

9. The method of producing a carotenoid having 50 carbon atoms according to the above-described item 8, wherein the cyclization as defined in the above-described item 8 comprises β-cyclization, and the cell as defined in the above-described item 8 is further transformed with a gene encoding an enzyme that hydroxylates a β-ring and/or an enzyme that ketolates a β-ring in a carotenoid having 50 carbon atoms and having the β-ring at an end thereof.

10. The method of producing a carotenoid having 50 carbon atoms according to any one of the above-described items 1 to 7, wherein the cell as defined in any one of the above-described items 1 to 7 is further transformed with a gene encoding an enzyme that oxidizes a desaturated carotenoid having 50 carbon atoms obtained by desaturating the carotenoid backbone compound of 50 carbon atoms.

11. A mutant phytoene desaturase gene, into which a mutation to encode a mutant phytoene desaturase having an enhanced activity to desaturate a carotenoid backbone compound of 50 carbon atoms has been introduced.

12. The mutant phytoene desaturase gene according to the above-described item 11, wherein the mutation to encode a mutant phytoene desaturase having an enhanced activity to desaturate a carotenoid backbone compound of 50 carbon atoms causes a substitution of an amino acid corresponding to at least one amino acid selected from asparagine at position 304, phenylalanine at position 339, isoleucine at position 338, aspartic acid at position 395, and isoleucine at position 228 in an amino acid sequence set forth in SEQ ID NO: 1.

13. The mutant phytoene desaturase gene according to the above-described item 11 or 12, wherein the mutation of the mutant phytoene desaturase gene causes at least a substitution of an amino acid corresponding to asparagine at position 304 in SEQ ID NO: 1 by proline or serine.

14. A mutant phytoene desaturase, which is encoded by the mutant phytoene desaturase gene according to any one of the above-described items 11 to 13.

15. A cell producing a carotenoid having 50 carbon atoms by desaturating a carotenoid backbone compound of 50 carbon atoms, which is transformed with the mutant phytoene desaturase gene according to any one of the above-described items 11 to 13.

Advantageous Effects of Invention

The production method of the present invention allows the carotenoid backbone compound of 50 carbon atoms to be efficiently desaturated, and thus the carotenoids having 50 carbon atoms having a great variety of structures can be produced. Some enzymes including a wild-type phytoene desaturase exhibited a desaturation efficiency of only about several % at maximum for the carotenoid backbone compound f 50 carbon atoms. In contrast, the production method of the present invention has provided drastically increased desaturation efficiency. Thus, a desaturated carotenoid having 50 carbon atoms can be delivered to downstream modifying enzymes, and thereby a great variety of carotenoids having 50 carbon atoms can be produced.

A carotenoid backbone compound of 40 carbon atoms (30 carbon atoms in certain species of bacteria) free of oxygen and the like undergoes various modifications such as oxygenation. As a result, carotenoids acquire a great variety of structures. The most major carotene in nature is β-carotene having a β-ring, and various enzymes that modify the β-ring exist in nature. According to the production method of the present invention, a carotenoid having 50 carbon atoms and a β-ring can be synthesized. In addition, a great variety of carotenoids can be produced by using various enzymes that modify the β-ring.

The carotenoid having 50 carbon atoms produced by the production method of the present invention is expected to, for example, have the following potentialities: an antioxidant function improved as compared to a conventional carotenoid; a color gamut as a pigment extended to a range that has not been reported heretofore; and property of hardly undergoing destructive metabolism.

Further, in the production method of the present invention, conventional culture media and conditions may be used, and hence the carotenoid having 50 carbon atoms can be simply synthesized.

In addition, the production method of the present invention can be utilized for carrying out the highly efficient synthesis of a desaturated $C_{55}$ carotenoid, a desaturated $C_{60}$ carotenoid, and the like.

BRIEF DESCRIPTION OF THE DRAWINGS

FIG. 2(*a*) illustrates pAC-$fds_{Y81A,V157A}$-$crtM_{F26A,W38A,F233S}$, which was produced by inserting lac promoter/operator (lacPO)-crt $M_{F26A,W38A,F233S}$ and lac promoter/operator (lacPO)-$fds_{Y81A,\ V157A}$ into a pACmod vector. FIG. 2(*b*) illustrates pUC-pBAD-crtI*, which was produced by removing the lac promoter/operator from a pUC18Nm vector, inserting an araCgene/araBAD promoter sequence (derived from a pBADHisA vector), and inserting crtI variants (crtI*) downstream of the promoter. FIG. 2(*c*) illustrates pUC-pBAD-crtI*-crtY, which was produced by inserting crtY downstream of the crtI variants in pUC-pBAD-crtI*. FIG. 2(*d*) illustrates pUC-pBAD-crtI*-crtWZY, which was produced by inserting crtW, crtZ, and crtY downstream of the crtI variants in pUC-pBAD-crtI*. FIG. 2(*e*) illustrates pUC-pBAD-crtI*-crtA, which was produced by inserting crtA downstream of the crtI variants in pUC-pBAD-crtI*. FIG. 2(*f*) illustrates pUC-$fds_{Y81A,V157A}$, which was produced by inserting an $fds_{Y81A,V157A}$ gene downstream of lacPO in a pUC18Nm vector. FIG. 2(*g*) illustrates pAC-crt $M_{F26A,W38A,F233S}$, which was produced by inserting laCPO-$crtM_{MF26A,W38A,F233S}$ into the BamHI site of a pACmod vector. FIG. 2(*h*) illustrates pAC-$crtM_{F26A,\ W38A,\ F233S}$-idi, which was produced by inserting lacPO-idi upstream of the ClaI site of pAC-$crtM_{F26A,W38A,F233S}$.

FIG. 4(*a*) illustrates an overview of procedures of a screening experiment system, and FIG. 4(*b*) illustrates a screening principle.

In FIG. 20, (b) shows that C50-caloxanthin (peak 3) and C50-nostoxanthin (peak 2) were produced by the additional expression of CrtG, and (c) shows that C50-zeaxanthin-β-D-diglucoside (peak 5) was produced by the additional expression of CrtX.

DETAILED DESCRIPTION OF THE INVENTION

Figure 1:
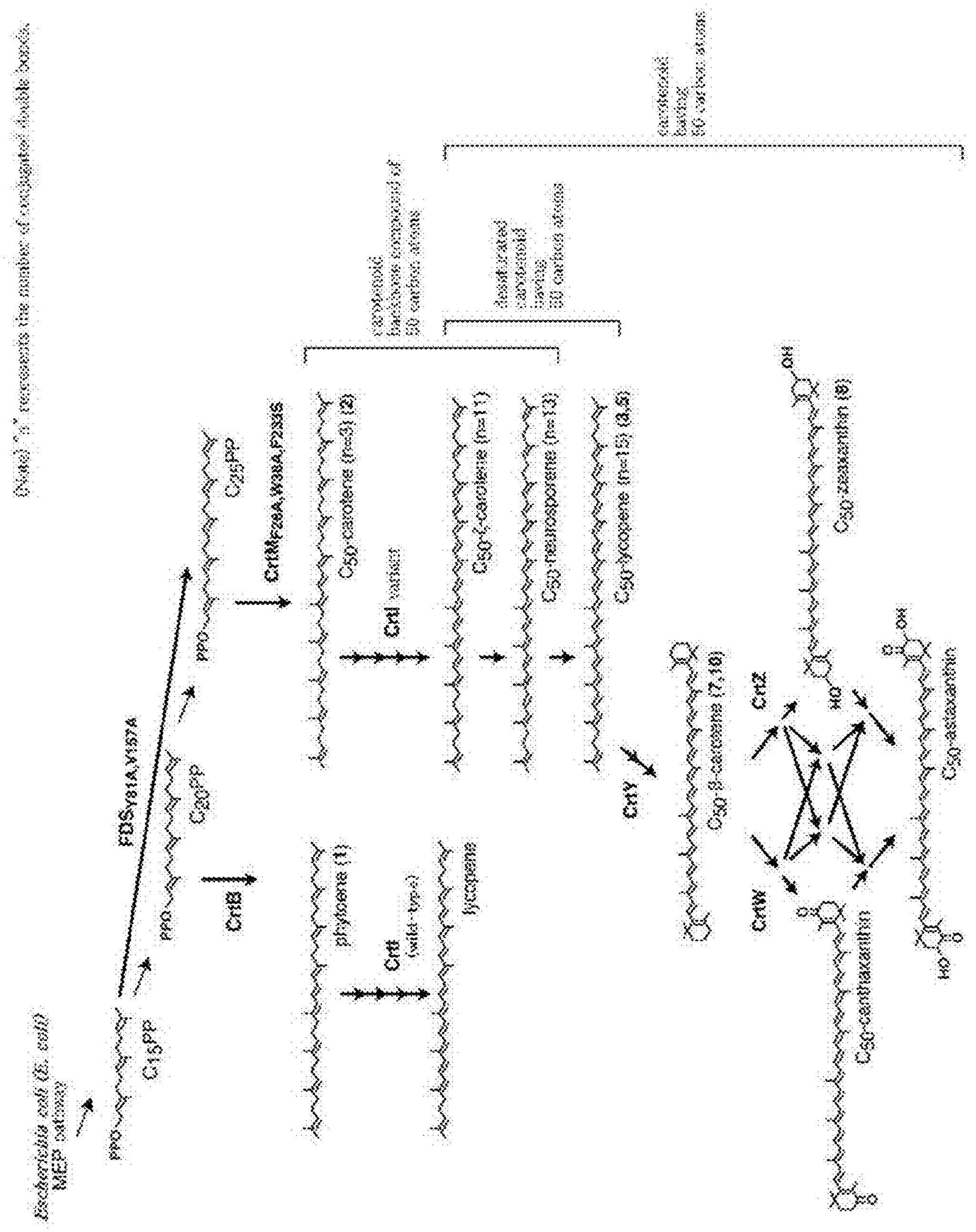
FIG. 1 illustrates functions of enzymes involved in carotenoid biosynthesis, and carotenoid biosynthetic pathways. Abbreviations for the enzymes that catalyze the corresponding reactions are given beside respective arrows. Further, numerals given in parentheses following compound names correspond to numbers of peaks of HPLC analysis in FIG. 6.

First, carotenoid biosynthetic pathways are described (see FIG. 1). Carotenoids are biosynthesized from mevalonic acid or pyruvic acid in nature. First, isopentenyl diphosphate (hereinafter referred to as "IPP") and dimethylallyl diphosphate (hereinafter referred to as "DMAPP"), a compound obtained by the isomerization of IPP, are synthesized through a mevalonate pathway or a non-mevalonate pathway (MEP pathway in FIG. 1). Next, geranyl diphosphate (hereinafter referred to as "$C_{10}$PP") is synthesized by condensation of IPP and DMAPP. Then, farnesyl diphosphate (hereinafter referred to as "$C_{15}$PP") and geranylgeranyl diphosphate (hereinafter referred to as "$C_{20}$PP") are synthesized by the sequential addition of two molecules of IPP. $C_{15}$PP is synthesized by a farnesyl diphosphate synthase, and $C_{20}$PP is synthesized by a geranylgeranyl diphosphate synthase.

In a pathway for synthesizing a carotenoid having 40 carbon atoms, phytoene is synthesized by condensation of two molecules of $C_{20}$PP with a phytoene synthase (CrtB), and serves as a precursor for a carotenoid (carotenoid backbone compound).

Phytofluene, ζ-carotene, neurosporene, lycopene, tetradehydrolycopene, and the like are synthesized by sequential desaturation of phytoene. Various carotenoids such as α-carotene, β-carotene, γ-carotene, δ-carotene, ϵ-carotene, lutein, zeaxanthin, canthaxanthin, fucoxanthin, astaxanthin, antheraxanthin, and violaxanthin are synthesized by modification of the ends of lycopene through cyclization or oxidation. It should be noted that carotenoids constructed only of carbon and hydrogen are classified as carotenes, while carotenoids containing an oxygen element in addition to carbon and hydrogen are classified as xanthophylls.

The present invention enables production of a carotenoid having 50 carbon atoms by alteration of biosynthetic pathways for carotenoids present in nature, and is directed to a production method for a carotenoid having 50 carbon atoms, wherein the production method comprises: culturing, in a medium, a cell transformed with a mutant phytoene desaturase gene; and obtaining a carotenoid having 50 carbon atoms from a culture after the culturing. It should be noted that, in this description, "50 carbon atoms" is sometimes simply referred to as "$C_{50}$", and the same applies to, for example, 35, 40, 45, 55, and 60 carbon atoms.

In this description, the "carotenoid having 50 carbon atoms" is distinguished from a "carotenoid backbone compound of 50 carbon atoms" to be desaturated by a mutant phytoene desaturase, and refers to a compound whose number of double bonds has been increased by one or more by the desaturation of the carotenoid backbone compound of 50 carbon atoms. The carotenoid having 50 carbon atoms may undergo any modification, and also includes, for example, one having a β ring or an ϵ ring at its ends, and one having a functional group containing an element other than carbon and hydrogen, such as a hydroxyl group or a keto group. Further, the carotenoid having 50 carbon atoms may be any carotenoid as long as the number of carbon atoms derived from a backbone compound is 50, and also includes, for example, one in which the total number of carbon atoms is 50 or more as a result of the addition of a functional group containing carbon, such as a methyl group or an acetyl group, by modification.

The "carotenoid backbone compound of 50 carbon atoms" is a precursor for the carotenoid having 50 carbon atoms, which may be desaturated by a mutant phytoene desaturase. Specific examples of the carotenoid backbone compound of 50 carbon atoms include: $C_{50}$-carotene (n=3) (16,16'-diisopentenylphytoene); and compounds in which the number of conjugated double bonds in $C_{50}$-carotene (n=3) is increased by 1 to 5. Specific examples of the compounds in which the number of the double bonds in $C_{50}$-carotene (n=3) is increased by 1 to 5 include: $C_{50}$-carotene (n=5), which is obtained by increasing the number of the double bonds by 1; $C_{50}$-carotene (n=7), which is obtained by increasing the number of the double bonds by 2; and $C_{50}$-ζ-carotene (n=11) and $C_{50}$-neurosporene (n=13) in FIG. 1. It should be noted that, in this description, "n", which is described, for example, following common names for compounds, represents the number of conjugated double bonds.

In this description, the carotenoid backbone compound of 50 carbon atoms that has been desaturated by a mutant phytoene desaturase but has not undergone any modification afterwards is referred to as "desaturated carotenoid having 50 carbon atoms." The desaturated carotenoid having 50 carbon atoms is a linear compound that does not have any functional group except for that derived from a backbone compound. The desaturated carotenoid having 50 carbon atoms is encompassed by the carotenoid having 50 carbon atoms. Specific examples of the desaturated carotenoid having 50 carbon atoms include compounds in which the number of double bonds in $C_{50}$-carotene (n=3) is increased by 1 to 6, and do not include $C_{50}$-carotene (n=3) itself. It should be noted that the compound in which the number of the double bonds in $C_{50}$-carotene (n=3) is increased by 6 is $C_{50}$-lycopene (n=15).

Further, in this description, the term "compound having a carotenoid backbone of 50 carbon atoms" is used in some cases as a concept including all of the carotenoid having 50 carbon atoms, the carotenoid backbone compound of 50 carbon atoms, the desaturated carotenoid having 50 carbon atoms, and the like.

The mutant phytoene desaturase that catalyzes a reaction for desaturating the carotenoid backbone compound of 50 carbon atoms is obtained by inducing a mutation in a wild-type phytoene desaturase (CrtI). The phytoene desaturase (CrtI) is an enzyme that desaturates phytoene having 40 carbon atoms. In nature, CrtI catalyzes a synthesis reaction of lycopene that contains 11 conjugated double bonds, by desaturating phytoene that contains 3 conjugated double bonds to sequentially introduce double bonds. The mutant phytoene desaturase in the present invention has an enhanced activity to desaturate the $C_{50}$ carotenoid backbone compound as compared to the wild-type phytoene desaturase by virtue of the introduction of a mutation.

The mutant phytoene desaturase in the present invention may be derived from any organisms including plants, bacteria, and the like as long as the mutant phytoene desaturase has an enhanced activity to desaturate the $C_{50}$ carotenoid backbone compound by virtue of a mutation. The mutant phytoene desaturase is preferably derived from microorganisms, more preferably derived from bacteria belonging to the genus *Pantoea* (formerly named the genus *Erwinia*), still more preferably derived from *Pantoea ananatis* (formerly named *Erwinia uredovora*). The amino acid sequence of the wild-type phytoene desaturase (CrtI) derived from *Pantoea ananatis* is set forth in SEQ ID NO: 1 of the sequence listing.

In the present invention, a mutant phytoene desaturase gene (crtI*) encodes the mutant phytoene desaturase. A mutation in the mutant phytoene desaturase gene may be any mutation as long as it achieves the object of the present invention. The mutation preferably causes a substitution of an amino acid corresponding to at least one amino acid selected from asparagine at position 304, phenylalanine at position 339, isoleucine at position 338, aspartic acid at position 395, and isoleucine at position 228 in the amino acid sequence set forth in SEQ ID NO: 1, more preferably causes at least a substitution of an amino acid corresponding to asparagine at position 304 in SEQ ID NO: 1 by proline or serine, still more preferably causes at least a substitution of an amino acid corresponding to asparagine at position 304 in SEQ ID NO: 1 by proline. Herein, the "amino acid corresponding to an amino acid at position X in SEQ ID NO: 1" defines that an amino acid as a target of the mutation is at position X counting from the N-terminus in SEQ ID NO: 1, but encompasses that the position X is expressed with a different numerical value in a phytoene desaturase having an amino acid sequence different from the amino acid sequence set forth in SEQ ID NO: 1.

The mutant phytoene desaturase gene is specifically exemplified by a phytoene desaturase gene derived from *Pantoea ananatis* (nucleotide sequence set forth in SEQ ID NO: 2 of the sequence listing), the nucleotide sequence having introduced therein a mutation causing a desired amino acid substitution. The mutant phytoene desaturase gene is exemplified by a gene having a nucleotide sequence of SEQ ID NO: 3 in which adenine (A) at position 911 is substituted by guanine (G) in the nucleotide sequence of SEQ ID NO: 2. The substitution of the nucleotide at position 911 causes a substitution of asparagine at position 304 in the amino acid sequence of SEQ ID NO: 1 by serine. It should be noted that SEQ ID NO: 2 has introduced therein non-synonymous mutations G1131A and A1476T. Further, the mutant phytoene desaturase gene is exemplified by a gene having a nucleotide sequence in which the nucleotide sequence AAC at positions 910 to 912 in the nucleotide sequence of SEQ ID NO: 2 is substituted by CCT, CCC, CCA, or CCG, more preferably CCT (nucleotide sequence set forth in SEQ ID NO: 28 of the sequence listing). The substitution of such bases causes a substitution of asparagine at position 304 in the amino acid sequence of SEQ ID NO: 1 by proline (amino acid sequence set forth in SEQ ID NO: 27 of the sequence listing). It should be noted that SEQ ID NO: 28 has introduced therein non-synonymous mutations G1131A and A1476T.

The nucleotide sequence of the mutant phytoene desaturase gene may be determined by producing a mutant gene library and screening a gene encoding an enzyme that has a function of interest from the library. The screening may be performed by, for example, a method described in Examples. Once the nucleotide sequence is determined, the mutant phytoene desaturase gene may be obtained by, for example, chemical synthesis, PCR using a cloned probe as a template, or a site-directed mutagenesis method.

The present invention includes the step of culturing, in a medium, a cell to be transformed with a mutant phytoene desaturase gene. The cell may be one originally harboring any other carotenoid biosynthetic gene, or may be one transformed with any other carotenoid biosynthetic gene. The other carotenoid biosynthetic gene is involved in a reaction upstream or downstream of a desaturating reaction for the $C_{50}$ carotenoid backbone compound. The upstream reaction corresponds to a pathway for supplying the $C_{50}$ carotenoid backbone compound, and the downstream reaction corresponds to a pathway for further modifying the $C_{50}$ desaturated carotenoid.

The pathway for supplying the $C_{50}$ carotenoid backbone compound is described. IPP, DMAPP, $C_{10}$PP, $C_{15}$PP, and $C_{20}$PP can be originally synthesized in many cells, in particular, all microorganisms. It is preferred that the cell in the present invention can synthesize geranylfarnesyl diphosphate (hereinafter sometimes referred to as "$C_{25}$PP") from $C_{15}$PP and/or $C_{20}$PP, and can synthesize the $C_{50}$ carotenoid backbone compound via the condensation of two molecules of $C_{25}$PP. It is more preferred that the cell in the present invention be transformed with at least one of a gene encoding an enzyme that synthesizes $C_{25}$PP from $C_{15}$PP and/or $C_{20}$PP or a gene encoding an enzyme that synthesizes the $C_{50}$ carotenoid backbone compound via the condensation of two molecules of $C_{25}$PP.

The gene encoding the enzyme that synthesizes $C_{25}$PP from $C_{15}$PP and/or $C_{20}$PP may be any gene having a function of interest. Such gene is exemplified by a mutant gene of a farnesyl diphosphate synthase (FDS) derived from *Geobacillus stearothermophillus*, a moderate thermophilic bacterium belonging to the genus *Geobacillus* (Ohnuma, S. et al., J Biol Chem 271, 30748-30754 (1996), JP 2010-258989). The mutant gene is exemplified by a gene encoding a double mutant of FDS ($FDS_{Y81A,\ V157A}$) in which tyrosine at position 81 is substituted by alanine (Y81A) and valine at position 157 is substituted by alanine (V157A) ($fds_{Y81A,\ V157A}$: SEQ ID NO: 4 of the sequence listing).

The gene encoding the enzyme that synthesizes the $C_{50}$ carotenoid backbone compound via the condensation of two molecules of $C_{25}$PP may be any gene having a function of interest. Such gene is exemplified by a mutant gene of a diapophytoene synthase (CrtM) derived from *Staphylococcus aureus*, which synthesizes a $C_{30}$ carotenoid backbone compound via the condensation of two molecules of $C_{15}$PP. The mutant gene is exemplified by a gene encoding a triple mutant of CrtM ($CrtM_{F26A,W38A,F233S}$) in which phenylalanine at position 26 and tryptophan at position 38 are substituted by alanine (F26A and W38A) and phenylalanine at position 233 is substituted by serine (F233S) $CrtM_{F26A,W38A,F233S}$: SEQ ID NO: 5 of the sequence listing). It has been found that $CrtM_{F26A,W38A,F233S}$ synthesizes the $C_{50}$ carotenoid backbone compound in an extremely efficient manner.

The cell of the present invention is preferably transformed with both of the gene encoding the enzyme that synthesizes $C_{25}$PP from $C_{15}$PP and/or $C_{20}$PP and the gene encoding the enzyme that synthesizes the $C_{50}$ carotenoid backbone compound from two molecules of $C_{25}$PP because the cell can produce the $C_{50}$ carotenoid backbone compound with high efficiency. In addition, the cell of the present invention may be transformed with a gene (idi) encoding an enzyme that isomerizes IPP into DMAPP (e.g., an isopentenyl diphosphate isomerase (Idi)) in addition to the above-mentioned genes. When the cell is transformed with the gene encoding the enzyme that isomerizes IPP into DMAPP, the production amount of the $C_{50}$ carotenoid backbone compound and the specificity can be further improved.

The pathway for further modifying the $C_{50}$ desaturated carotenoid is described. The $C_{50}$ desaturated carotenoid is considered to correspond to lycopene or tetradehydrolycopene in nature, and it is predicted that the $C_{50}$ desaturated carotenoid may be modified by various enzymes involved in the modification of lycopene. The cell in the present invention may contain a gene encoding an enzyme that cyclizes the ends of the $C_{50}$ desaturated carotenoid and/or a gene encoding an enzyme that oxidizes the $C_{50}$ desaturated carotenoid by oxygenation. In addition, when the cell in the present invention has the gene encoding the enzyme that cyclizes the ends of the $C_{50}$ desaturated carotenoid (in particular, β-cyclization), the cell may be transformed with a gene encoding an enzyme that hydroxylates a cyclic moiety (in particular, a β-ring) and/or a gene encoding an enzyme that ketolates a cyclic moiety (in particular, a β-ring). It should be noted that the β-ring has the same meaning as a β-ionone ring.

The gene encoding the enzyme that cyclizes the ends of the $C_{50}$ desaturated carotenoid may be any gene having a function of interest. Such gene is exemplified by a gene (crtY) encoding a lycopene cyclase (CrtY) derived from *Pantoea ananatis*, which synthesizes β-carotene from lycopene (Misawa N. et al., J Bacteriol 172, 6704-6712 (1990)).

In a carotenoid having β-cyclized ends, a gene encoding an enzyme that hydroxylates the β-ring and/or a gene encoding an enzyme that ketolates the β-ring may be any gene having a function of interest. Such gene is exemplified by a β-ionone ring-3-hydroxylase (CrtZ) gene (crtZ) or β-ionone ring-4-ketolase (β-ionone ring-4-oxygenase) (CrtW) gene (crtW) derived from a marine bacterium *Paracoccus* sp. strain N81106 (formerly named *Agrobacterium aurantiacum*) or derived from a marine bacterium *Brevundimonas* sp. strain SD-212 (Misawa N. et al., J Bacteriol 177, 6575-6584 (1995); Nishida, Y. et al., Appl Environ Microbiol 71, 4286-4296 (2005)). A nucleotide sequence in which crtZ and crtW derived from *Paracoccus* sp. strain N81106 and crtY described above are combined is set forth in SEQ ID NO: 6. A β-ionone ring-3-hydroxylase catalyzes a reaction for hydroxylating carbon at the 3-position of a β-ring, and a β-ionone ring-4-ketolase catalyzes a reaction for oxygenating carbon at the 4-position of a β-ring to form a carbonyl group (keto group).

The gene encoding the enzyme that oxidizes the $C_{50}$ desaturated carotenoid may be any gene having a function of interest. Such gene is exemplified by a spheroidene monooxygenase (CrtA) gene (crtA) derived from *Rhodobacter sphearoides* (SEQ ID NO: 7). A spheroidene monooxygenase is an enzyme that catalyzes an oxidation reaction for converting spheroidene into spheroidenone by inserting an oxygen atom.

The cell of the present invention may be transformed with genes encoding various enzymes involved in the pathway for modifying the $C_{50}$ desaturated carotenoid other than those described above, depending on the kind of a carotenoid to be produced. For example, when the cell is transformed with a β-ionone ring-2-hydroxylase (CrtG) gene (expressed as "CrtV" in WO 2005/049643 A1) derived from *Brevundimonas* sp. strain SD-212 (Nishida, Y. et al, Appl Environ Microbiol 71, 4286-4296, 2005), a $C_{50}$ carotenoid having a β-ring hydroxylated at the 2-position and the 2'-position, the organic synthesis of which has been considered to be difficult, can also be produced. Further, when the cell is transformed with a zeaxanthin glucosyl transferase (crtX) gene derived from *Pantoea ananatis* (Misawa N, J Bacteriol 172, 6704-6712, 1990), a $C_{50}$ carotenoid in which hydroxyl groups at the 3-position and 3'-position of a β-ring are glycosidized can also be produced.

A cell capable of producing a $C_{50}$ carotenoid in the present invention may be produced by selecting an appropriate expression vector and employing a known foreign gene introduction and expression method (e.g., Sambrook, J., Russel, D. W., Molecular Cloning A Laboratory Manual, 3rd Edition, CSHL Press, 2001). The cell is obtained by: preparing a gene to be introduced into the cell by transformation by using a conventional method such as a PCR method; incorporating the gene into an expression vector suitable for a host by using a conventional method; selecting a vector of interest; and transforming a host cell with the vector by using a conventional method. When transforming a cell with two or more kinds of genes, the cell may be transformed with the plurality of genes incorporated into the same expression vector, or may be cotrans formed with the plurality of genes incorporated into different expression vectors.

The cell serving as the host is not limited, but microorganisms such as *E. coli, Bacillus subtilis*, and yeast are preferred in view of shortening of a culturing time and ease of cloning. In particular, *E. coli* and yeast are preferred. Suitable examples of the *E. coli* include: cloning strains such as *Escherichia coli* XL1-Blue (hereinafter simply referred to as "*E. coli* XL1-Blue"); expression strains such as HB101 and BL21; and gene knockout strains in which the synthesis amount of a terpene precursor is large, such as JW1750 ΔgdhA (glutamate dehydrogenase-deficient) and JW0110 ΔaceE (pyruvate dehydrogenase-deficient) (Baba, T. et al.; Mol Syst Biol 2, 2006 0008 (2006)). Suitable examples of the yeast include standard budding yeast INVSc1 (invitrogen) and YPH499 (stratagene).

The expression vector into which the gene is applied is not particularly limited and may be a vector to be generally used. For example, when the host is *E. coli*, there are given ones derived from pUC18, pACYC184, and the like. When the host is *Bacillus subtilis*, there are given pUB110, pE194, pC194, pHY300PLK DNA, and the like. And when the host is yeast, there are given pRS303, YEp213, TOp2609, and the like.

Whether or not a gene of interest is introduced into the host cell may be confirmed by a conventional method such as a PCR method, a Southern hybridization method, or a northern hybridization method.

The production method for a $C_{50}$ carotenoid of the present invention includes the step of culturing, in a medium, the cells as the transformants obtained as described above. The medium may be any medium containing a substance that may serve as a supply source for the $C_{50}$ carotenoid backbone compound, and may be any medium containing an ingredient to be generally used for cell culturing. For cells in which the $C_{50}$ carotenoid backbone compound is synthesized by the metabolism of IPP and DMAPP, the medium may be any medium containing a carbon source that may serve as a supply source for IPP and DMAPP. Examples of such carbon source include a variety of sugars such as glucose.

A temperature at the time of the culturing is not particularly limited but is set to preferably 18 to 30° C., more preferably 20 to 30° C.

Culture period is also not particularly limited but the culturing is performed for preferably 12 to 72 hours, more preferably 24 to 48 hours after the expression of the gene introduced by the transformation.

The $C_{50}$ carotenoid can be collected from the culture after the culturing in accordance with a method to be generally employed for obtaining a product such as a carotenoid from cells of microorganisms or the like. It may also be possible to separate only the cells from the culture and obtain the carotenoid from the cells.

It should be noted that the present invention is also directed to a mutant phytoene desaturase gene, a mutant phytoene desaturase encoded by the mutant phytoene desaturase gene, and a cell capable of desaturating a $C_{50}$ carotenoid backbone compound to produce a $C_{50}$ carotenoid, which is transformed with the mutant phytoene desaturase gene.

Further, the present invention can be utilized in the highly efficient synthesis of a desaturated $C_{55}$ carotenoid, a desaturated $C_{60}$ carotenoid, or the like. For example, the desaturated $C_{55}$ carotenoid as well as the C50 carotenoid can be produced with high efficiency by utilizing the present invention using a double mutant of a farnesyl diphosphate synthase (FDS) ($FDS_{I78G,Y81A}$) in which isoleucine at position 78 is substituted by glycine (I78G) and tyrosine at position 81 is substituted by alanine (Y81A) in FDS (Ohnuma S et al., J Biol Chem 273, 26705-26713, 1998). Further, the desaturated $C_{60}$ carotenoid can be produced with high efficiency by utilizing the present invention using a $C_{30}PP$ synthase (HexPS) derived from *Micrococcus luteus* (Shimizu N et al, J Bacteriol 180, 1578-1581, 1998), that is, by co-expressing $FDS_{I78G,Y81A}$ or HexPS with the CrtM variant.

EXAMPLES

Hereinafter, the present invention is specifically described by way of Examples. However, the present invention is by no means limited thereto.

Reference Example 1

Synthesis of $C_{50}$ Carotenoid Backbone Compound (1) Supply of $C_{50}$ Carotenoid Raw Material, $C_{25}PP$ A mutant gene $fds_{Y81A,\ V157A}$ was used in order to efficiently synthesize $C_{25}PP$ in *E. coli*. $fds_{Y81A,\ V157A}$ is a mutant of a farnesyl diphosphate synthase (FDS) derived from *Geobacillus stearothermophillus*. The mutation Y81A is derived from Ohnuma, S. et al., J Biol Chem 271, 30748-30754 (1996). Further, the inventors of the present invention produced $fds_{Y81A,V157A}$ encoding a mutant enzyme having further shifted size specificity for a substrate by further introducing a mutation into a mutant gene $fds_{Y81A}$ through the use of the screening method for a terpene synthase gene disclosed in JP 2010-258989.

(2) Synthesis of $C_{50}$ Carotenoid Backbone Compound

A mutant gene $crtM_{F26A,W38A,233S}$ was used for the synthesis of a $C_{50}$ carotenoid backbone compound (16,16'-diisopentenylphytoene) via the condensation of two molecules of $C_{25}PP$. A diapophytoene synthase (CrtM) derived from *Staphylococcus aureus* is originally an enzyme that synthesizes a $C_{30}$ backbone carotenoid via the condensation of two molecules of $C_{15}PP$. The inventors of the present invention introduced a mutation into a crtM gene in order to produce an enzyme having improved size selectivity for a substrate (Umeno et al., J Bacteriol 184, 6690-6699 (2002), Umeno et al., Nucleic Acids Res 31, e91 (2003)). It was found that a $C_{50}$ carotenoid backbone compound was synthesized in a trace amount by feeding $C_{25}PP$ to a double mutant of CrtM having mutations F26A and W38A (Non Patent Literature 7).

The inventors also found that a triple mutant of CrtM having introduced therein mutations F26A, W38A, and F233S synthesized a $C_{50}$ carotenoid backbone compound from two molecules of $C_{25}PP$ in an extremely efficient manner, and synthesized a $C_{60}$ carotenoid backbone compound, though in a trace amount, when $C_{30}PP$ was fed (Maiko Furubayashi, Mayu Ikezumi, Kyoichi Saito, Daisuke Umeno. Activity evolution of unnatural carotenoid synthetic pathways, Annual Meeting of the Kanto Branch of the Japan Society for Bioscience, Biotechnology, and Agrochemistry, 2010, Oct. 9, 2010: Daisuke Umeno, Maiko Furubayashi, Mayu Ikezumi, Akinori Katabami, Ling Li, Jun Kajiwara. Creation and development of unnatural biosynthetic pathways, The Third Annual Meeting of the Japanese Society for Cell Synthesis Research, Institute of Industrial Science, the University of Tokyo, Nov. 12, 2010: Furubayashi M, Saito K, Umeno D, In-laboratory genetic drift of carotenoid synthase and its evolution of size specificity. The international chemical congress of Pacific basin societies, Hawaii, USA, Dec. 17, 2010: Maiko Furubayashi, Mayu Ikezumi, Kyoichi Saito, Daisuke Umeno. Selective synthesis of unnatural carotenoid by combinatorial expression of enzyme mutant, Annual Meeting of the Japan Society for Bioscience, Biotechnology, and Agrochemistry, 2011, March 2011). It was found that $C_{50}$-carotene (n=3), a $C_{50}$ carotenoid backbone compound, was efficiently (about 61%) produced by co-expressing $fds_{Y81A,\ V187A}$ for supplying $C_{25}PP$ and $crtM_{F26A,W38A,F233S}$ in *E. coli* XL1-Blue.

(3) It should be Noted that the Transformation of *E. Coli* XL1-Blue with $fds_{Y81A,V157A}$ and $crtM_{F26A,W38A,F233S}$ was performed by producing plasmids pAC-$crtM_{F26A,W38A,F233S}$ (FIG. 2(*g*): SEQ ID NO: 8) and pUC-$fds_{Y81A,V157A}$ (FIG. 2(*f*): SEQ ID NO: 9) in accordance with a conventional method.

pAC-$crtM_{F26A,W38A,F233S}$ was produced by inserting lac promoter/operator (lacPO)-$crtM_{MF26A,W38A,F233S}$ into the BamHI site of a pACmod vector (Claudia Schmidt-Dannert et al., Nat. Biotechnol., 18: 750-753 (2000)).

pUC-$fds_{Y81A,V157A}$ was produced by inserting an $fds_{Y81A,V157A}$ gene downstream of lacPO of a pUC18Nm vector (Umeno D. et al, J Bacteriol 184, 6690-6699 (2002)).

The transformed *E. coli* was cultured in accordance with the technique disclosed in Non Patent Literature 7.

The analysis of the produced carotenoid was performed by HPLC also in accordance with the method disclosed in Non Patent Literature 7.

Example 1

Improved Synthesis of $C_{50}$ Carotenoid Backbone Compound

In addition to $fds_{Y81A,\ V157A}$ and $crtM_{F26A,W38A,F233S}$, a gene (derived from *E. coli* genome) encoding an isopentenyl diphosphate isomerase (Idi) was expressed in *E. coli* XL1-Blue, and the *E. coli* was cultured. The transformation of *E. coli* XL1-Blue with $fds_{Y81A,\ V157A}$ and $crtM_{F26A,W38A,F233S}$ was performed by producing plasmids pAC-crt $M_{F26A,W38A,F233S}$-idi (FIG. 2(*h*): SEQ ID NO: 10) and pUC-$fds_{Y81A,V157A}$ (FIG. 2(*f*): SEQ ID NO: 9) in accordance with a conventional method. pAC-$crt_{MF26A,W38A,F233S}$-idi was produced by inserting lacPO-idi upstream of the ClaI site of pAC-$crt_{MF26A,W38A,F233S}$. pUC-$fds_{Y81A,V157A}$ was produced in the same manner as in Reference Example 1. The culturing of the transformed *E. coli* and the analysis of the produced carotenoid were performed in the same manner as in Reference Example 1.

Figure 3:
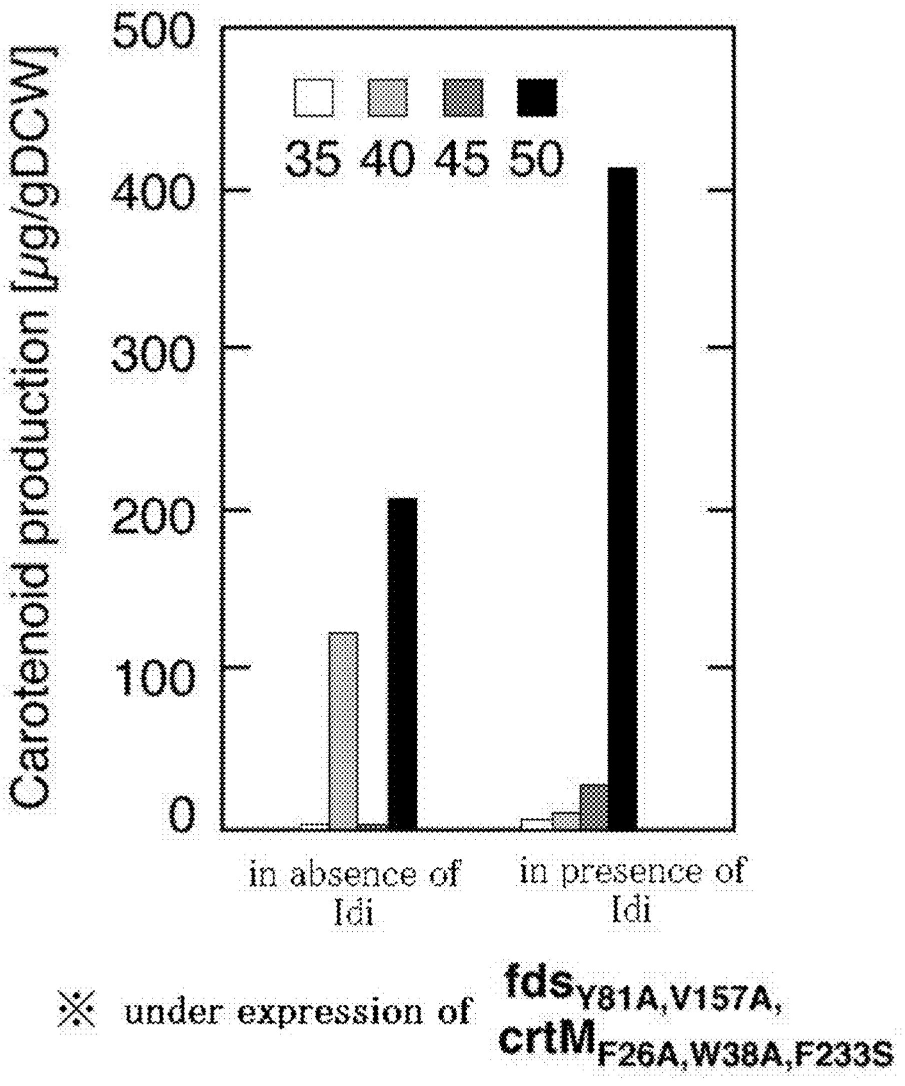
FIG. 3 shows the synthesis amount of a $C_{50}$ carotenoid backbone compound in the case where Idi is co-expressed in a metabolic pathway constructed with $FDS_{Y81A,\ V157A}$ and $CrtM_{F26A,\ W38A,\ F233S}$ (Example 1). "Absence of idi" and "Presence of idi" represent the synthesis amounts of a compound having a $C_{35}$ carotenoid backbone (35), a compound having a $C_{40}$ carotenoid backbone (40), a compound having a $C_{45}$ carotenoid backbone (45), and a compound having a $C_{50}$ carotenoid backbone (50) obtained by subjecting acetone extracts from *E. coli* transformed with various genes to HPLC analysis. Specifically, in FIG. 3, "35" represents 4-apophytoene, "40" represents phytoene, "45" represents 16-isopentenylphytoene, and "50" represents $C_{50}$-carotene (n=3).

FIG. 3 shows the results. The production amount of $C_{50}$-carotene (n=3), a $C_{50}$ carotenoid backbone compound, was increased in the case of introducing Idi as compared to the case of not introducing Idi. Further, phytoene, a $C_{40}$ carotenoid backbone compound, was synthesized in a large amount in the case of not introducing Idi, whereas the production amount of phytoene was decreased and the specificity of the production of $C_{50}$-carotene (n=3) was improved in the case of introducing Idi. The synthetic efficiency of $C_{50}$-carotene (n=3) was found to be improved (about 90%) in the case of introducing Idi.

Reference Example 2

Desaturation of $C_{50}$ Carotenoid Backbone Compound by Wild-Type CrtI

The inventors of the present invention found that a carotenoid having a $C_{50}$ carotenoid backbone compound was desaturated by CrtI (phytoene desaturase encoded by a gene having a nucleotide sequence of SEQ ID NO: 2 (having introduced therein non-synonymous mutations G1131A and A1476T)) (Non Patent Literature 9). However, it was found that its production amount is extremely small and only 25% of the $C_{50}$ carotenoid backbone compound was desaturated (Non Patent Literature 8).

Meanwhile, the inventors of the present invention found that the constitutive expression of wild-type CrtI using a lac promoter (lacP) or the like remarkably inhibited cell growth, and remarkably destabilized cell pigmentation. However, no clear cytotoxicity was observed in cells having a pathway to the synthesis/accumulation of the $C_{50}$ carotenoid backbone compound (e.g., the cells obtained in Reference Example 1 and Example 1).

The inventors of the present invention attempted to ligate crtI downstream of an araBAD promoter capable of reducing leaky expression (low-level expression occurring without any induction) and express the ligation product in *E. coli* XL1-Blue. A group of carotenoid biosynthetic genes upstream of crtI were constitutively expressed by lacP. After the density/number of the cells had reached sufficient levels, it was attempted to make pigment in the cells by inducing the expression of crtI to desaturate the $C_{50}$ carotenoid backbone compound.

Figure 2:
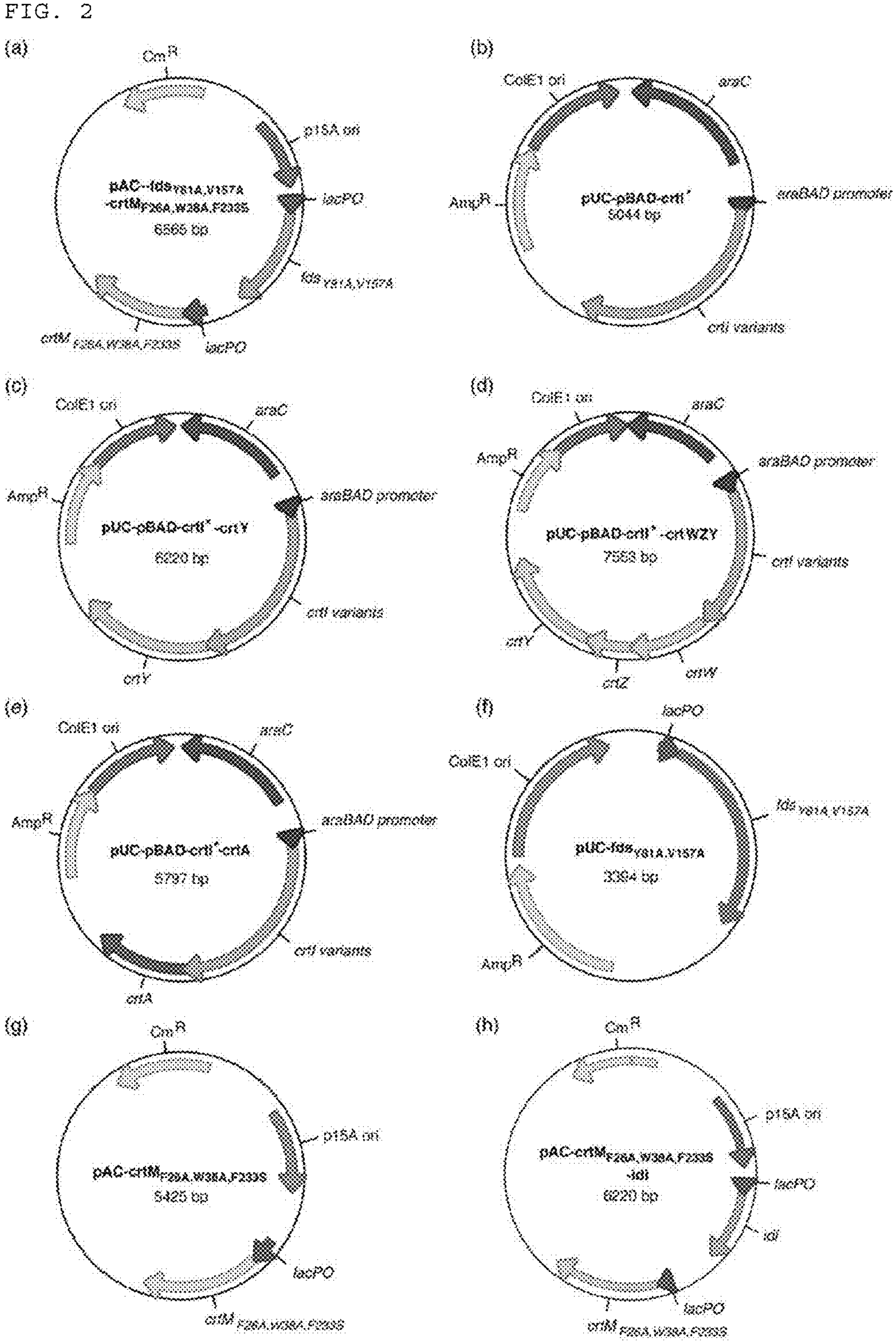
FIG. 2 illustrates plasmid maps (a)~(h) used in Examples 1 to and Reference Examples 1 and 2.

The plasmid used is pUC-pBAD-crtI (having crtI introduced into the crtI variant part in FIG. 2(*b*)). The lac promoter/operator (lacPO) of a pUC18Nm vector (Umeno D. et al, J Bacteriol 184, 6690-6699 (2002)) was removed, and an araC gene/araBAD promoter sequence derived from a pBADHisA vector (invitrogen) was inserted. crtI was inserted into the XhoI-ApaI site downstream of the promoter. crtI is a gene encoding a wild-type phytoene desaturase derived from *Pantoea ananatis* (Misawa N. et al., J Bacteriol 172, 6704-6712 (1990)).

The problem of the cytotoxicity was overcome in *E. coli* transformed with pUC-pBAD-crtI. However, the $C_{50}$ carotenoid backbone compound was desaturated with extremely low efficiency, which was almost unrecognizable.

Example 2

Acquisition of crtI Variant Desaturating $C_{50}$ Carotenoid Backbone Compound

Figure 4:
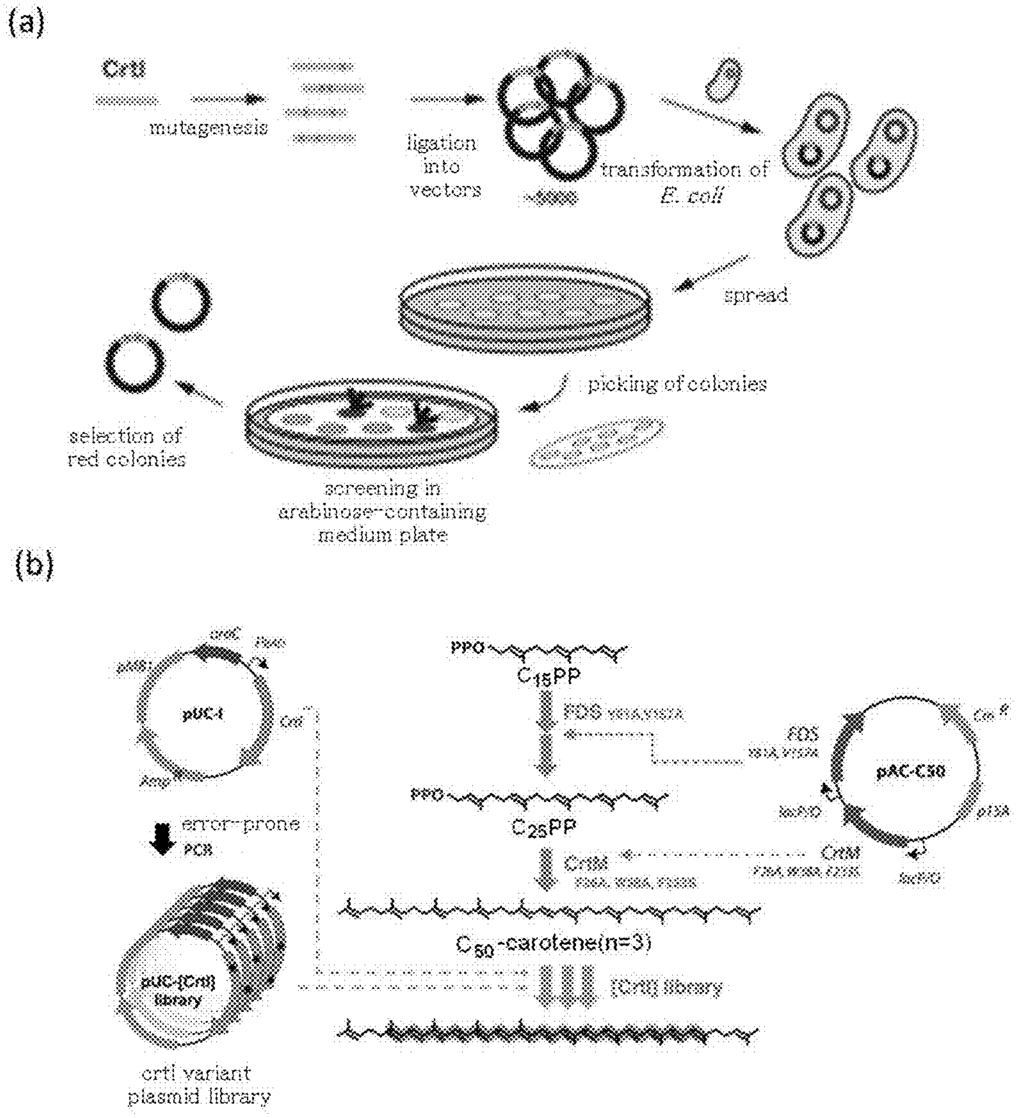
FIG. 4 illustrates the screening of a mutant phytoene desaturase capable of efficiently desaturating a carotenoid backbone compound of 50 carbon atoms (Example 2).

Based on the evolutionary engineering of a phytoene desaturase (CrtI), it was attempted to acquire a crtI variant that desaturates more efficiently the $C_{50}$ carotenoid backbone compound. FIG. 4(*a*) illustrates an overview of procedures of this example, and FIG. 4(*b*) illustrates a screening principle.

First, a plasmid pUC-pBAD-crtI containing wild-type crtI (represented by "pUC-I" in FIG. 4(*b*)) was used as a template, and a random mutation was introduced into crtI by an error-prone PCR method using $MnCl_2$ (Cadwell et al.: PCR Methods Appl 2, 28-33 (1992)). The obtained PCR product was digested with restriction enzymes XhoI and ApaI, and ligated into the restriction enzyme sites of XhoI and ApaI downstream of an araBAD promoter in a pUC-pBAD vector. *E. coli* XL10-Gold (Stragatene) was transformed with the ligation product, and part thereof was spread on a Luria Bertani (LB) solid medium. The remaining transformed *E. coli* was added to 10 mL of an LB liquid medium and cultured at 37° C. overnight. After that, a plasmid was extracted from 2 mL of the culture and used as a "crtI variant plasmid library." Further, the number of the transformed cells (library size), which was calculated from the number of the colonies formed on the solid medium, was $10^5$ cfu/transformation.

*E. coli* XL1-Blue harboring a plasmid pAC-crt$M_{F26A,W38A,F233S}$-fds$_{Y81A,V157A}$ (represented by "pAC-$C_{50}$" in FIG. 4(*b*) SEQ ID NO: 11) was transformed with the thus obtained plasmid library and spread on an LB solid medium (containing 50 μg/mL carbenicillin and 30 μg/mL chloramphenicol) on which a nitrocellulose filter was mounted. The cells were cultured at 37° C. for 24 hours until the colonies were formed, and then left to stand still at room temperature for an additional 48 hours.

As a control, *E. coli* XL1-Blue was transformed with pUC-pBAD-crtI containing wild-type crtI. In this case, the colonies developed a flesh color. In the group of about 2,000 colonies obtained by transformation with the crtI variant plasmid library, 8 colonies developing a particularly intense reddish violet color were visually detected. The colonies were named CrtI-m1, m2, . . . , and m8, respectively. As illustrated in FIG. 4(*b*), $C_{50}$-lycopene (n=15), a $C_{50}$ desaturated carotenoid, is a pigment developing a reddish violet color, and it is estimated that, as a result of the efficient synthesis of such compound, the colonies developed a reddish violet color.

The bacterial strain of each of the colonies was cultured in an LB liquid medium at 37° C. for 12 hours to extract a plasmid, and the nucleotide sequence of a crtI variant contained in the plasmid was analyzed by a dideoxy method. Table 1 below shows the analysis results.

TABLE 1

Analysis results of gene mutations in CrtI variants

| Sample names | Gene mutations (amino acid mutations are shown in parentheses) |
|---|---|
| CrtI-m1 | A195G, A594G, T1016C (F339S) |
| CrtI-m2 | A911G (N304S) |
| CrtI-m3 | None |
| CrtI-m4 | T1015C (F339L), G1183A (D395N) |
| CrtI-m5 | None |
| CrtI-m6 | A682G (I228V), A1012G (I338V) |
| CrtI-m7 | T144C, A1012G (I338V) |
| CrtI-m8 | A911G (N304S), T1017C |

It was found that CrtI-m2 and CrtI-m8 had the same mutation in which asparagine (N) at position 304 was substituted by serine (S) (N304S). Further, CrtI-m1 and CrtI-m4 each had a mutation in which phenylalanine (F) at position 339 was substituted by serine (S) or leucine (L) (F339S or F339L), and CrtI-m6 and CrtI-m7 each had a mutation in which isoleucine (I) at position 338 was substituted by valine (V) (1338V). It was estimated that the CrtI variants each had an enhanced ability to desaturate a $C_{50}$ carotenoid backbone compound by virtue of those mutations.

Example 3

Synthesis of Desaturated $C_{50}$ Carotenoid by CrtI Variant

Of the colonies obtained in Example 2, each of CrtI-m1, m2, m4, m6, and m8, which showed enhanced pigmentation as compared to wild-type CrtI, was confirmed for its ability to desaturate a $C_{50}$ carotenoid backbone compound.

*E. coli* XL1-Blue harboring pAC-crt$M_{F26A,W38A,F233S}$-fds$_{Y81A,V157A}$ was transformed with each of the plasmids pUC-pBAD-CrtI-m1, m2, m4, m6, and m8. The transformant was spread on an LB agar medium on which a nitrocellulose (NC) membrane was contracted, and cultured at 37° C. for 24 hours. The plasmids pUC-pBAD-CrtI-m1, m2, m4, m6, and m8 have various mutant genes mut1, mut2, mut4, mut6, and mut8 inserted into the crtI* part in pUC-pBAD-crtI*-crtY of FIG. 2(*c*), respectively, and the nucleotide sequence of the plasmid having inserted therein mut2 is set forth in SEQ ID NO: 12.

After the formation of the colonies, the NC membrane with the colonies was transferred onto an LB agar medium containing 0.2% arabinose, followed by incubation at room temperature. The colonies were inoculated into 2 mL of an LB medium (containing 50 μg/mL carbenicillin and 30 μg/mL chloramphenicol) and cultured at 37° C. overnight. 300 μL of the culture medium were inoculated into 30 mL of a TB medium (containing 50 μg/mL carbenicillin and 30 μg/mL chloramphenicol), followed by incubation under shaking at 30° C. and 200 rpm. After the incubation under shaking for 24 hours, 20% arabinose was added to the culture medium so as to have a final concentration of 0.2%, followed by incubation under shaking (30° C.) for an additional 48 hours.

The culture medium was measured for its $OD_{600}$, and the cells were harvested by centrifugation. The pellet obtained by harvesting the cells was washed with physiological saline, and a lipid-soluble fraction was extracted with 10 mL of acetone. A 300-μL aliquot was fractionated from the extract and measured for its absorbance spectrum with Spectra Max 384 (Molecular Device).

Figure 5:
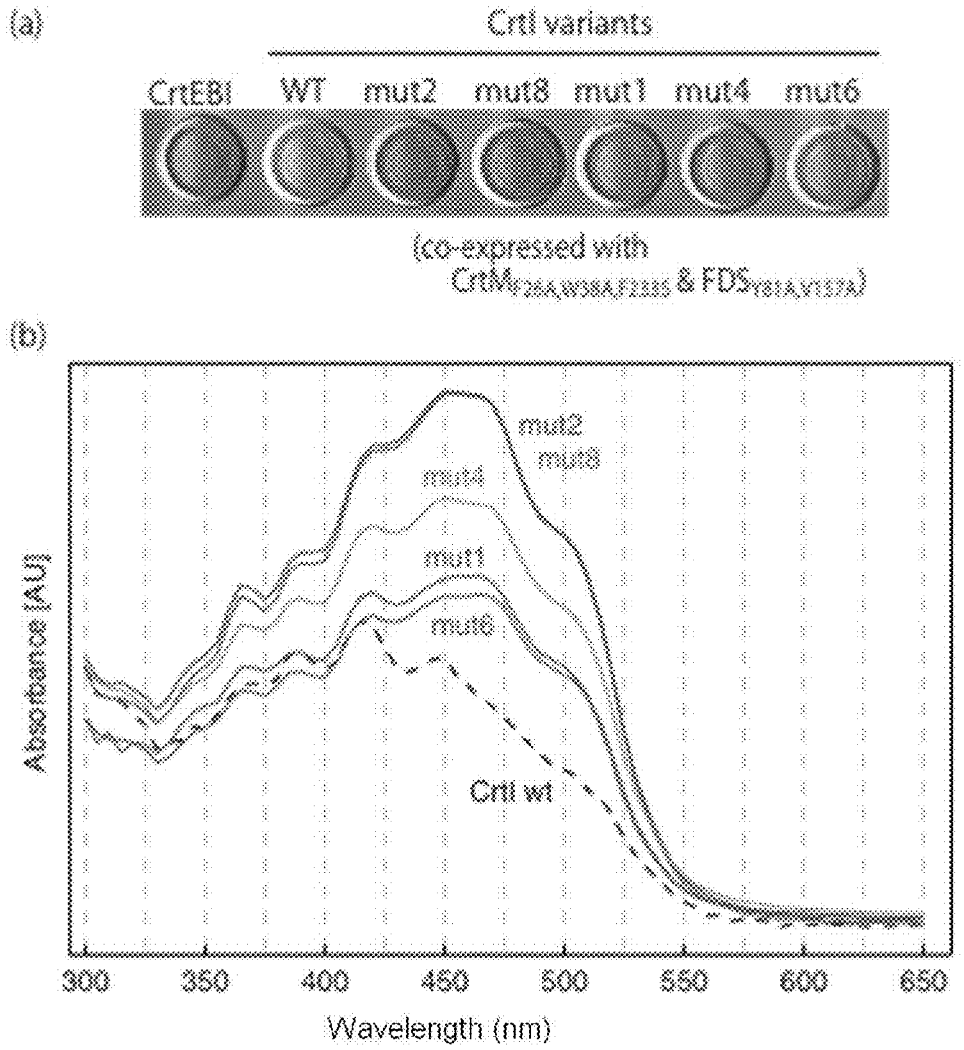
FIG. 5(*a*) shows the actual colors of acetone extracts of 6 colonies out of 8 colonies obtained by screening, and FIG. 5(*b*) shows the absorption spectra of the acetone extracts (Example 3). CrtEBI, a control, shows the result of the colony of *E. coli* transformed with a plasmid pAC-EBI containing crtE, crtB, and crtI derived from *Pantoea ananatis*. WT (or CrtIwt) shows the result of the colony of *E. coli* transformed with wild-type crtI, while mut1, mut2, mut8, mut4, and mut6 shows the results of the colonies of CrtI-m1, CrtI-m2, CrtI-m8, CrtI-m4, and CrtI-m6, respectively. It should be noted that the transformed *E. coli* synthesized lycopene.

FIGS. 5(*a*) and 5(*b*) show the results. FIG. 5(*a*) is a photograph showing the actual color of each acetone extract. The absorbance of the acetone extract at around 500 to 600 nm was increased in *E. coli* expressing mut2, mut8, mutt, mut4, or mut6 as compared to *E. coli* expressing wild-type crtI (WT) (FIG. 5(*b*)). In particular, CrtI-m2 and CrtI-m8 having crtI variants with N304S exhibited intense colors and absorbances. In the case of expressing those CrtI variants, a peak (shoulder) on the rightmost side is located at about 540 nm, indicating that a six-step desaturated product (15 conjugated double bonds) is contained in a large amount. The synthesis amount of the $C_{50}$ desaturated carotenoid was the largest in the case of introducing CrtI-m2 or CrtI-m8.

Next, the carotenoid synthesized in the case of CrtI-m2 was subjected to HPLC analysis. 1 mL of hexane and 35 mL of 10% NaCl were added to the acetone extract to extract a carotenoid fraction into a hexane phase. 75% of the hexane extract were collected and dehydrated with addition of a small amount of $MgSO_4$. The hexane solvent was removed by nitrogen, and the carotenoid fraction was finally concentrated into 100 μL of hexane. Thus, a carotenoid extract was obtained. 25 μL (75%×25%=19% of the total volume, corresponding to 7.3 mL of the medium) of the resultant carotenoid extract were injected into an HPLC-photodiode-array system. HPLC analysis was performed in accordance with the conditions of Takaichi, S. Photosynth Res, 65, 93-99 (2000) (column: Waters Spherisorb™ 5.0 μm ODS2 4.6 mm×250 mm Column, eluent: acetonitrile/tetrahydrofuran/metanol (58:7:35) 2 mL/min, detector: photodiode array (190 to 800 nm)). Further, the mass spectrometry of a sample fractionated by HPLC was performed through the use of an M-2500 Hitachi double-focusing mass spectrometer (Hitachi, Ltd.) at a field desorption mode (Takaichi (1993) Org. Mass Spectrom. 28: 785-788)).

Figure 6:
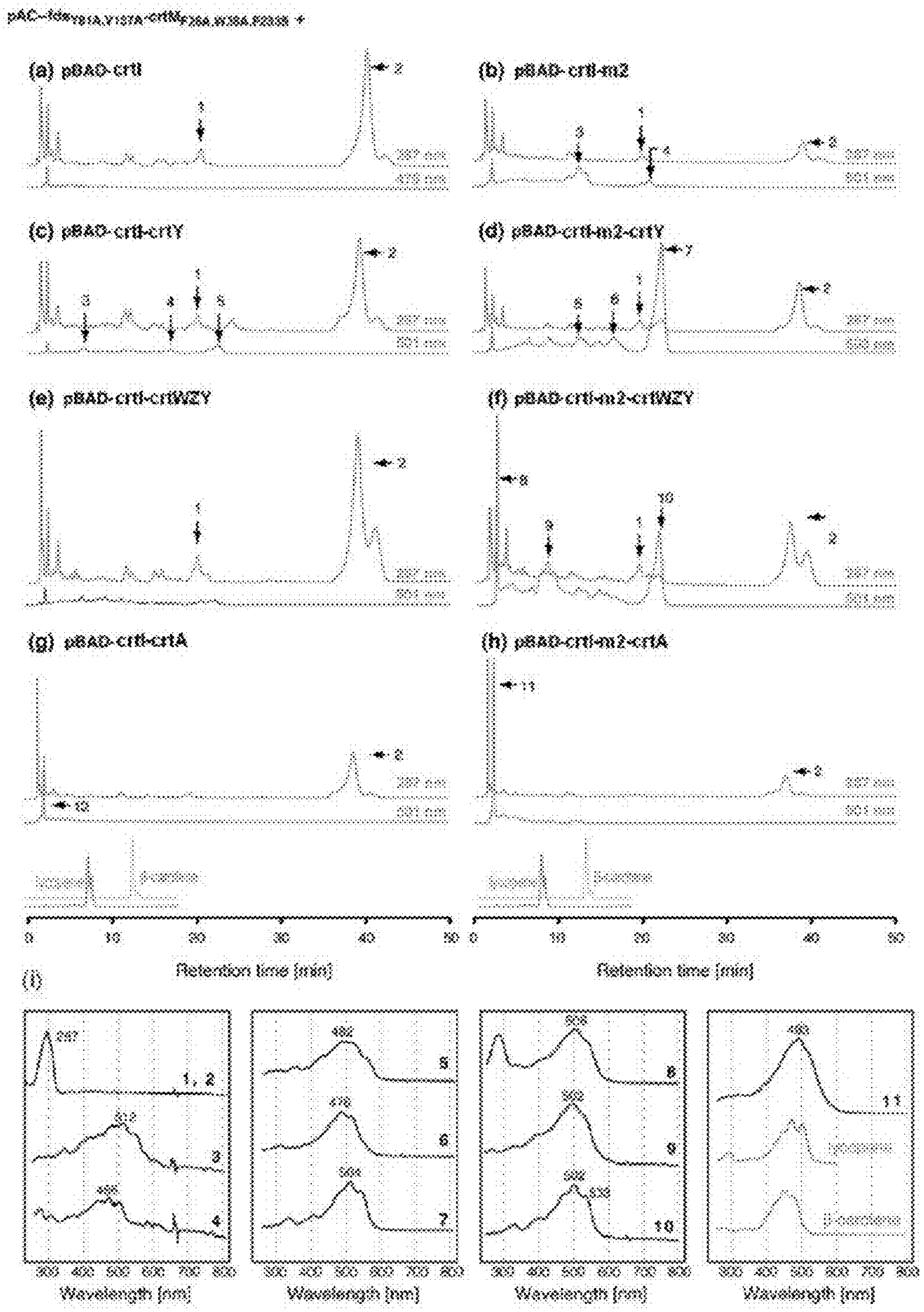
FIG. 6 shows the results of HPLC analysis of carotenoids produced by culturing *E. coli* that was co-transformed with pAC-$fds_{Y81A,V157A}$-$crtM_{F26A,W38A,F233S}$ and various plasmids (Examples 3 to 6). (a) to (h) show chromatograms obtained from HPLC analysis when introducing various plasmids. (i) shows the absorption spectra of compounds forming respective peaks. In (i), the rightmost numerical values correspond to the numbers of the peaks in the chromatograms, and the three-digit numerical values are values for maximum absorption wavelengths.

As a result, it was found that, in CrtI-m2, a compound ($C_{50}$-lycopene) obtained by the six-step desaturation of the $C_{50}$ carotenoid backbone compound was synthesized in a large amount (peak 3 in FIG. 6(*b*)). On the other hand, it was found that, in the case of transformation with wild-type CrtI, almost no desaturated compound was synthesized (FIG. 6(*a*)).

The analysis results for peak 2 and peak 3 in FIG. 6(*b*) are shown below. $C_{50}$-carotene (n=3): A sample corresponding to peak 2 in FIG. 6 (*b*) was fractionated by HPLC and subjected to mass spectrometry. The sample showed a much longer HPLC elution time than that of a desaturated carotenoid having the same size, and hence was estimated to be a compound having a $C_{50}$ carotenoid backbone. The absorption spectrum was similar to that of phytoene (n=3). The mass number obtained by the mass spectrometry was 680, which was consistent with that of a putative structure (Compound No. 2 in FIG. 1).

$C_{50}$-lycopene (n=15): A sample corresponding to peak 3 in FIG. 6 (*b*) was fractionated by HPLC and subjected to mass spectrometry. The HPLC elution time was relatively short. The absorption spectrum was similar to the literature value of 3,4,3',4'-tetradehydrolycopene (n=15) (Karrer and Rutschmann (1945) Helv. Chim. Acta 28: 793-795), and the absorption spectrum had the feature of an acyclic carotenoid. The mass number obtained by the mass spectrometry was 668, which was consistent with that of a putative structure (Compound No. 3 in FIG. 1).

Example 4

Cyclization of Desaturated $C_{50}$ Carotenoid $C_{50}$-lycopene (n=15), a desaturated $C_{50}$ carotenoid, was cyclized by using a crtY gene encoding a lycopene cyclase, which synthesizes a β-carotenoid from lycopene.

A plasmid pUC-pBAD-crtI/CrtI-m2-crtY was used for transformation with the crtY gene. The plasmid was produced by inserting an SpeI site following an ApaI site in pUC-pBAD-crtI/CrtI-m2 and inserting the crtY gene into the ApaI/SpeI site. The crtY gene is a gene encoding a lycopene cyclase derived from *Pantoea ananatis* (Misawa N. et al., J Bacteriol 172, 6704-6712 (1990)). It should be noted that the expression "CrtI-m2" in the plasmid means that a mutant gene crt$I_{N304S}$ derived from CrtI-m2 has been inserted. The nucleotide sequence of pUC-pBAD-CrtI-m2-crtY is set forth in SEQ ID NO: 13.

*E. coli* XL1-Blue harboring pAC-crt$M_{F26A,W38A,F233S}$-fds$_{Y81A,V157A}$ was transformed with pUC-CrtI-m2-CrtY. As a control, transformation was performed with crtY together with wild-type crtI in place of crtI-m2. The *E. coli* was spread on an LB agar medium on which a nitrocellulose (NC) membrane was mounted, and cultured at 37° C. for 24 hours. After the formation of colonies, the NC membrane with the colonies was transferred onto an LB agar medium containing 0.2% arabinose, followed by incubation at room temperature. Then, the color of the colonies was observed.

Figure 7:
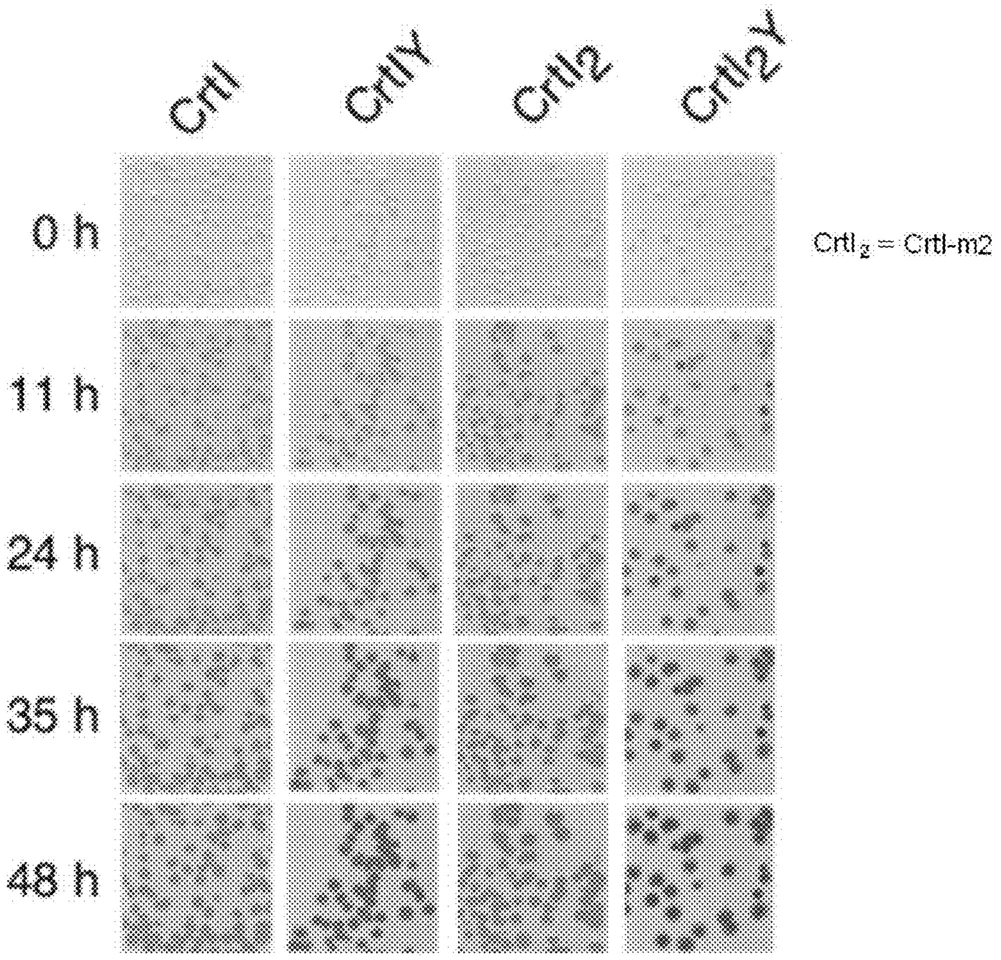
FIG. 7 shows the results of β-cyclic carotenoid synthesis through the cooperation of CrtI with CrtY. The photographs show colony colors in the 0 to 48 hours culture of cells into which various genes have been introduced (Example 4). CrtI shows the case where wild-type crtI was introduced into *E. coli*, CrtIY shows the case where both of wild-type crtI and crtY were introduced into *E. coli*, $CrtI_2$ shows the case where a crtI variant derived from CrtI-m2 was introduced into *E. coli*, and $CrtI_2Y$ shows the case where both of the crtI variant derived from CrtI-m2 and crtY were introduced into *E. coli*. It should be noted that in each *E. coli* pAC-$fds_{Y81A,V157A}$-$crtM_{F26A,W38A,F233S}$ has been introduced.

FIG. 7 shows the photographs of the transformed *E. coli* cultured for 0 to 48 hours. The *E. coli* transformed with a plasmid having crtY downstream of a crtI variant derived from CrtI-m2 ("CrtI$_2$Y" in FIG. 7) developed a very deep red color.

Further, the acetone extract was subjected to HPLC analysis and mass spectrometry by the same techniques as those of Example 3.

A carotenoid having a maximum absorption peak at 502 nm was detected by the HPLC analysis (peak 7 in FIG. 6(*d*)). This peak was confirmed in only a trace amount in the case of wild-type CrtI (peak 5 in FIG. 6(*c*)). FIG. 1 illustrates the putative structure of the thus obtained $C_{50}$ carotenoid and a synthetic pathway therefor. It should be noted that the numbers of the respective compounds in FIG. 1 correspond to numbers in the chromatograms of FIG. 6.

Figure 9:
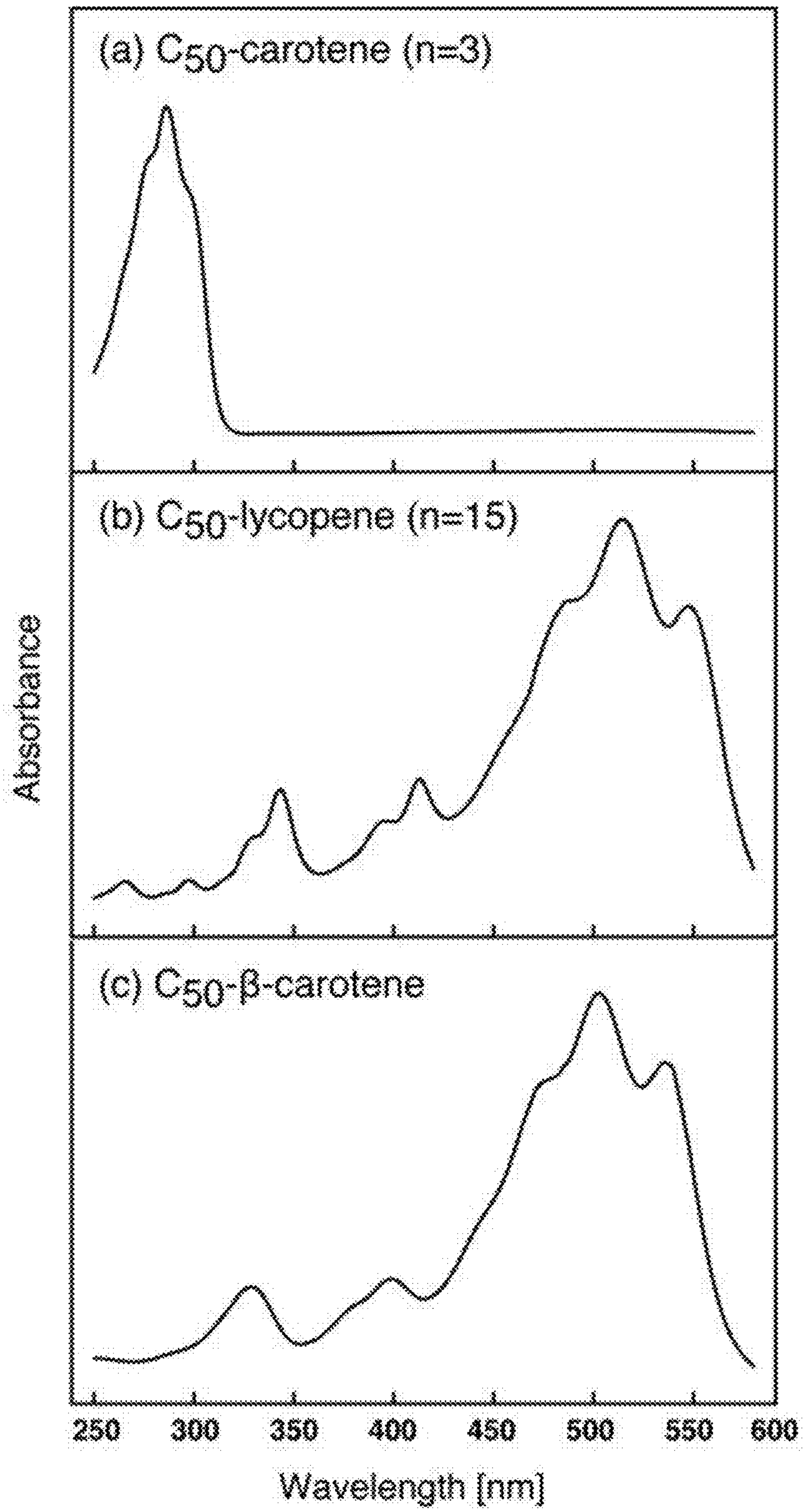
FIG. 9 shows the absorption spectra of $C_{50}$-carotene (n=3), $C_{50}$-lycopene (n=15), and $C_{50}$-β-carotene, respectively in (a), (b), and (c) (Examples 3 and 4).

$C_{50}$-β-carotene: A sample corresponding to peak 7 in FIG. 6(*d*) was fractionated by HPLC and subjected to mass spectrometry. The HPLC elution time was longer than that of $C_{50}$-lycopene. It is known that a similar behavior is shown in a $C_{40}$ carotenoid as well. The absorption spectrum was almost consistent with that of a chemically synthesized product (Khachik and Beecher (1985) J. Chromatogr. 346: 237-246) (FIG. 9(*c*)). The absorption spectrum was similar to one having the feature of a bicyclic carotenoid. The mass number obtained by mass spectrometry was 668, which was consistent with that of a putative structure (Compound No. 7 in FIG. 1).

Example 5

Extension of Cyclic $C_{50}$ Carotenoid Pathway by Additional Modification

An oxocarotenoid was synthesized by further extending the pathway for synthesizing a cyclic $C_{50}$ carotenoid confirmed in Example 4.

pUC-pBAD-crtI-crtWZY (FIG. 2(*d*): SEQ ID NO: 14), a plasmid containing crtW, crtZ, and crtY, was used. As for the plasmid, crtW, crtZ, and crtY of *Paracoccus* sp. strain N81106 (SEQ ID NO: 6) were amplified from a plasmid pAK32 (Misawa N. et al., J Bacteriol 177, 6575-6584 (1995)) by PCR. Through the use of crtW, crtZ, and crtY thus obtained, pUC-pBAD-crtI-crtWZY and pUC-pBAD-CrtI-m2-crtWZY were constructed. In the same manner as the technique of Example 4, the produced plasmids were introduced into *E. coli* (XL1-Blue) together with pAC-crtM$_{F26A,W38A,F233S}$-fds$_{Y81A,V157A}$, and the *E. coli* was cultured, followed by observing the color of colonies.

Figure 8:
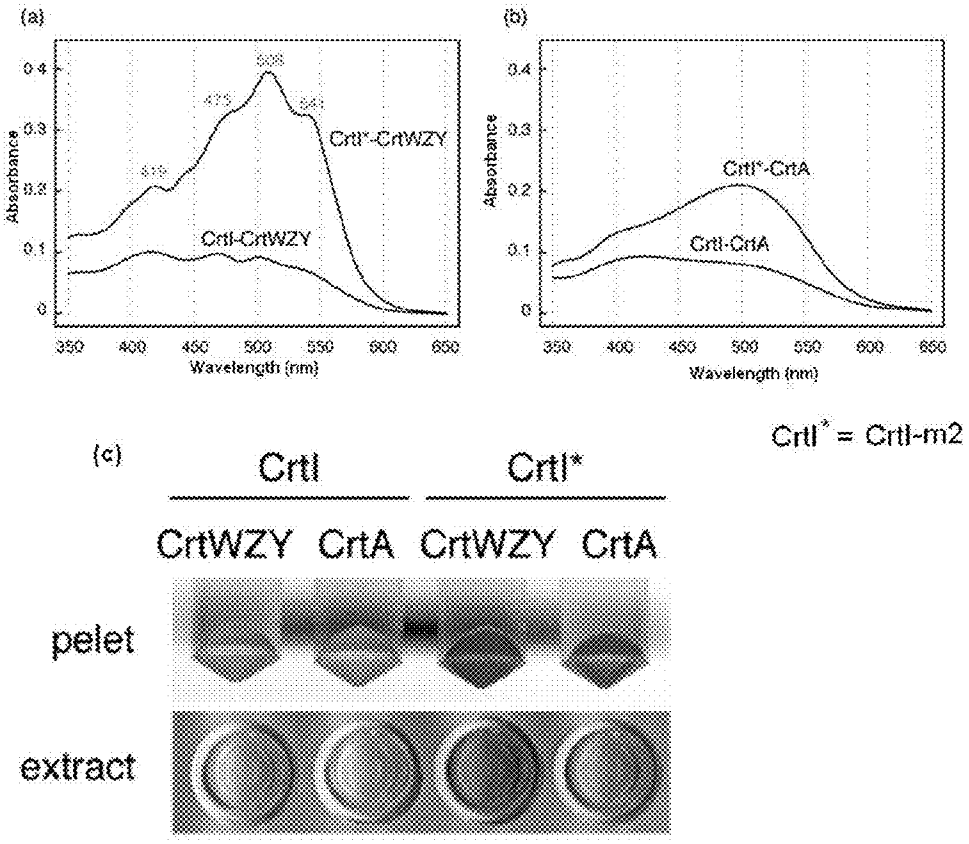
FIG. 8 shows the results of carotenoid synthesis through the cooperation of CrtI with CrtW, CrtZ, and CrtY, in (a), and the results of carotenoid synthesis through the cooperation of CrtI with CrtA, in (b) (Example 5). (a) and (b) show the absorption spectra of acetone extracts from *E. coli* transformed with various genes, and (c) is photographs showing the actual colors of cell pellets (upper row) and acetone extracts (lower row) in a similar case. CrtI* means that a crtI variant derived from CrtI-m2 was introduced into *E. coli*.

As a result, in a system having introduced therein pUC-pBAD-CrtI-m2-crtWZY, the colonies developed a vivid red color (the second line from the right in FIG. 8(*c*): CrtWZY in CrtI*).

The spectrum of the acetone extract was measured in the same manner as in Example 4. As a result, in the case of transformation with pUC-pBAD-CrtI-m2-crtWZY, an intense peak appeared at 508 nm (CrtI*-CrtWZY in FIG. 8(*a*)). On the other hand, in the case of using wild-type CrtI, only a trace amount of a pigment was accumulated (CrtI-CrtWZY in FIG. 7(*a*)). HPLC analysis was performed in the same manner as in Example 4. As a result, a novel carotenoid having high polarity and having a maximum absorption peak at 502 nm was obtained as a major peak (peak 9 in FIG. 6(*f*)). FIG. 1 illustrates the putative structure of the thus obtained carotenoid and a synthetic pathway therefor. It should be noted that the numbers of the respective compounds in FIG. 1 correspond to numbers in the chromatograms of FIG. 5.

Example 6

Oxidation of Desaturated $C_{50}$ Carotenoid

The total synthesis of crtA was performed by optimizing a codon for *E. coli* based on the amino acid sequence of CrtA derived from *Rhodobacter sphearoides* (SEQ ID NO: 7, commissioned to DNA2.0). Plasmids pUC-pBAD-crtI-crtA and pUC-pBAD-CrtI-m2-crtA were produced by using the synthesized gene (FIG. 2(*e*): SEQ ID NO: 15).

By the same techniques as those of Example 5, *E. coli* was transformed with the produced plasmids, and the *E. coli* was cultured, followed by observing the color of colonies and analyzing the spectrum of the acetone extract.

As a result, in the case of transformation with pUC-pBAD-CrtI-m2-crtA, the colonies developed a vivid color (the first line from the right in FIG. 8 (*c*): CrtA in CrtI*). Further, the acetone extract gave a broad absorption spectrum peculiar to an oxocarotenoid (CrtI*-CrtA in FIG. 8 (*b*)). In the case of co-expression of CrtA with wild-type CrtI, the colonies developed only a tint color. HPLC analysis was performed in the same manner as in Example 5. As a result, a novel carotenoid having high polarity appeared as a major peak (peak 11 in FIG. 6(*h*)).

Example 7

Acquisition of crtI Variant Having High Ability to Desaturate $C_{50}$ Carotenoid Backbone Compound The biosynthetic pathways for C50-lycopene and C50-β-carotene realized in Examples 3 and 4 left something to be improved in efficiency, because the C50 backbone (C50-carotene (n=3)) still remained. Thus, the acquisition of a CrtI variant having a higher ability to desaturate the C50 backbone was attempted. Of the CrtI variants obtained in Example 2, CrtI-m2 showed the highest C50 backbone desaturation efficiency. Thus, with attention focused on the amino acid substitution N304S of CrtI-m2, the site-directed total substitution of an amino acid at position 304 was performed to search a variant having higher desaturation efficiency.

First, a plasmid pUC-pBAD-crtI containing wild-type CrtI was used as a template, and a library was prepared by PCR using a primer having a randomized amino acid at position 304 (NNK codon) and the subsequent cloning. The resultant plasmid library was screened by the same method as that described in Example 2. Colonies developing a redder color than those of wild-type CrtI were searched to isolate plasmids of CrtI variants. Those CrtI variants were screened again. As a result, products substituted by glycine (G), serine (S), asparagine (N), proline (P), and alanine (A) gave particularly red colonies. Of those, a product substituted by P (codon: CCT) gave the reddest colonies. The amino acid sequence of CrtI having the product substituted by P is set forth in SEQ ID NO: 27 of the sequence listing, and a nucleotide sequence encoding the amino acid sequence is set forth in SEQ ID NO: 28.

Next, the synthesis amounts of C50-lycopene by CrtI-m2 and CrtI$_{N304P}$ were analyzed by HPLC. *E. coli* XL1-Blue was transformed with pUC-pBAD-crtI-m2 or pUC-pBAD-crtI$_{N304P}$ together with pAC-crtM$_{F26A,W38A,F233S}$-fds$_{Y81A,V157A}$. After the formation of colonies, an NC membrane with the colonies was transferred onto an LB agar medium containing 0.2% arabinose, followed by incubation at room temperature. The colonies were inoculated into 2 mL of an LB medium (containing 50 μg/mL carbenicillin and 30 μg/mL chrolamphenicol) and cultured at 37° C. overnight. 300 μL of the culture medium were inoculated into 30 mL of a TB medium (containing 50 μg/mL carbenicillin and 30 μg/mL chrolamphenicol), followed by incubation under shaking at 30° C. and 200 rpm. After the incubation under shaking for 36 hours, 20% arabinose was added to the culture medium so as to have a final concentration of 0.2%, followed by incubation under shaking (30° C.) for an additional 36 hours. HPLC analysis was performed by the method shown in Example 3.

Figure 10:
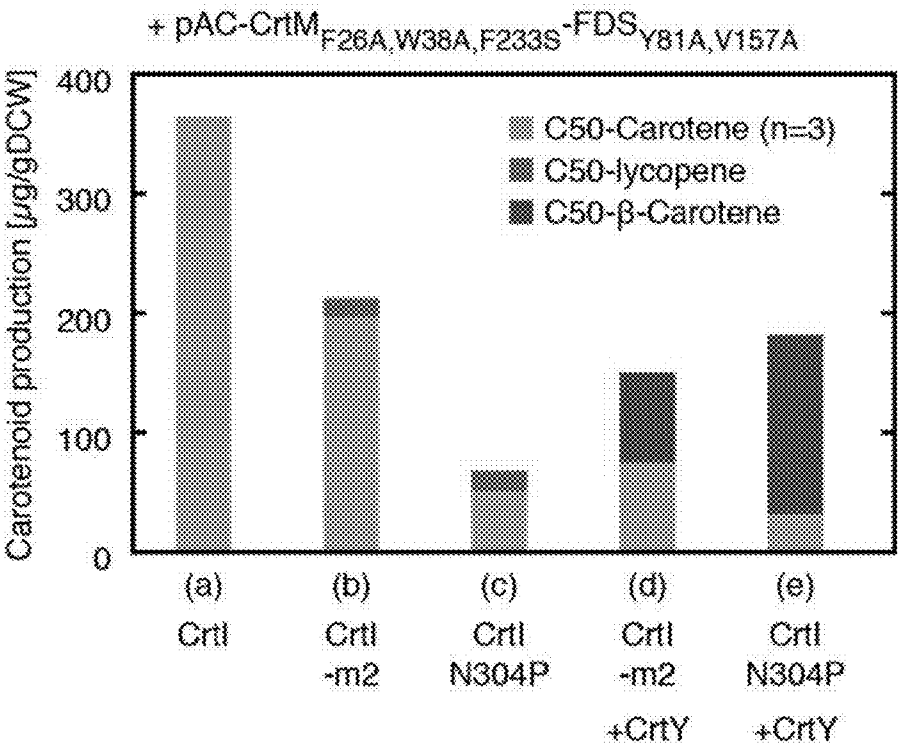
FIG. 10 shows the results of HPLC analysis of synthesis amounts of $C_{50}$-carotene (n=3), $C_{50}$-lycopene, and $C_{50}$-β-carotene by CrtI-m2 and $CrtI_{N304P}$ (Example 7). (a), (b), (c), (d), and (e) show the results of *E. coli* transformed with pUC-pBAD-CrtI, *E. coli* transformed with pUC-pBAD-CrtI-m2, *E. coli* transformed with pUC-pBAD-$CrtI_{N304P}$, *E. coli* transformed with pUC-pBAD-CrtI-m2-CrtY, and *E. coli* transformed with pUC-pBAD-$CrtI_{N304P}$-CrtY, respectively. Only $C_{50}$-carotene (n=3) was synthesized in (a), $C_{50}$-carotene (n=3) and $C_{50}$-lycopene were synthesized in (b) and (c), and $C_{50}$-carotene (n=3) and $C_{50}$-β-carotene were synthesized in (d) and (e).

FIG. 10 shows the results. In the case of using $CrtI_{N304P}$, the synthesis amount of C50-lycopene accumulated in the cells showed substantially no increase, whereas the production amount of C50-carotene (n=3) showed a clear decrease as compared to CrtIm2. This is probably because most of C50-lycopene undergoes decomposition because of its low intracellular stability, although the biosynthesis amount of C50-lycopene (desaturation efficiency of C50-carotene) is large (high).

Next, whether or not C50-β-carotene was increased more by using $CrtI_{N304P}$ was investigated. First, a pUC-pBAD-$crtI_{N304P}$-crtY plasmid was prepared. *E. coli* XL1-Blue was transformed with the plasmid and pUC-pBAD-crtI-m2-crtY together with pAC-$crtM_{F26A,W38A,F233S}$-$fds_{Y81A,V157A}$, and culturing, extraction, and HPLC analysis were performed in the same manner as in the above-mentioned sections.

As a result, C50-carotene (n=3) was decreased and C50-lycopene was increased in the case of using $CrtI_{N304P}$ as compared to the case of using CrtI-m2 (FIG. 10).

Example 8

Study on Use of CrtW and CrtZ Derived from *Brevundimonas* sp. Strain SD-212

In Example 5, it was attempted to produce C50-astaxanthin, in addition to C50-β-carotene, by the use of CrtW and CrtZ derived from *Paracoccus* sp. strain N81106. A polar peak appeared, but most of C50-β-carotene remained without any modification by CrtW or CrtZ. Thus, the synthesis of C50-astaxanthin and its intermediates C50-zeaxanthin and C50-canthaxanthin was attempted by the use of CrtW and CrtZ having higher efficiency.

Figure 11:
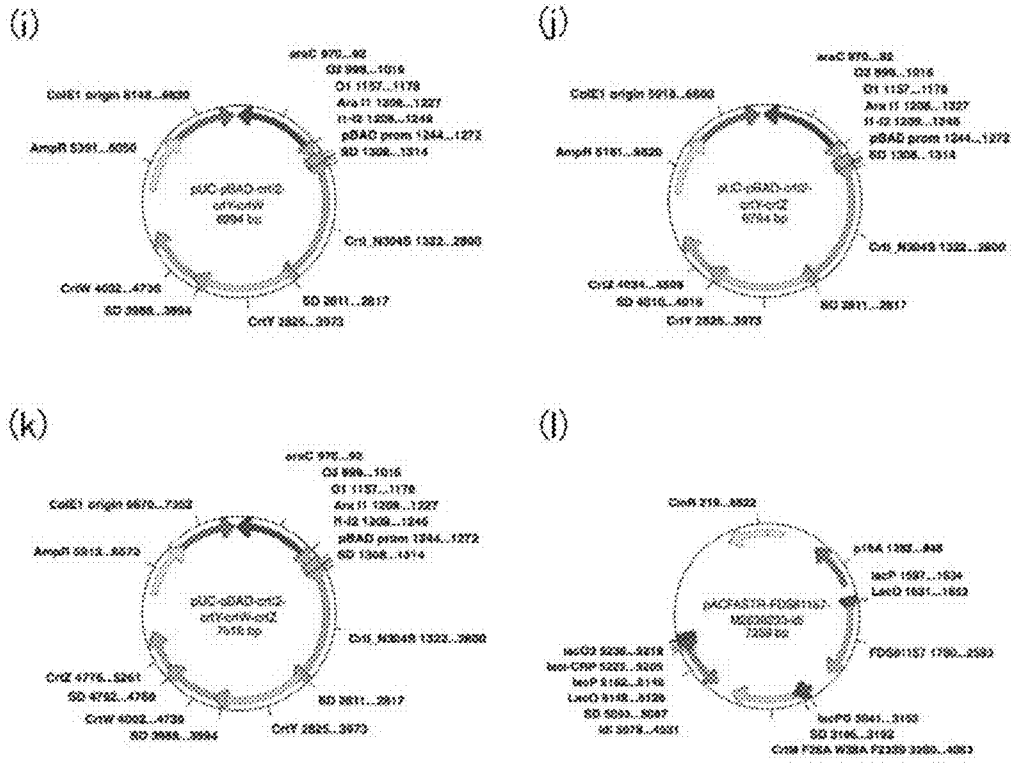
FIG. 11 illustrates plasmid maps (i)~(l) used in Examples 8 and 9. The plasmids contain CrtW and/or CrtZ derived from *Brevundimonas* sp. strain SD-212. (i) illustrates pUC-pBAD-$CrtI_{N304P}$-CrtY-$CrtW_{BD}$-$CrtZ_{BD}$. (j) illustrates pUC-pBAD-CrtI-m2-CrtY-$CrtW_{BD}$. (k) illustrates pUC-pBAD-CrtI-m2-CrtY-$CrtZ_{BD}$. (l) illustrates pAC-crt $M_{F26A,W38A,F233S}$-$fds_{Y81A,V157A}$-idi.

As previously reported (Choi S. et al., Mar Biotechnol 7, 515-522 (2005), Choi S. et al., Appl Microbiol Biotechnol 72, 1238-1246 (2006)), it has been found that CrtW and CrtZ derived from *Brevundimonas* sp. strain SD-212 are a β-carotene ketolase and β-carotene hydroxylase having high efficiency, respectively. In the synthesis of a natural (C40 type) astaxanthin, the enzymes are the best choices that are currently available. Thus, the total synthesis of those genes was performed with codon optimization for *E. coli*, which was commissioned to DNA2.0. Through the use of those genes, pUC-pBAD-$CrtI_{N304P}$-CrtY-$CrtW_{BD}$-$CrtZ_{BD}$ was prepared. Further, pUC-pBAD-CrtI-m2-CrtY-$CrtW_{BD}$ and pUC-pBAD-CrtI-m2-CrtY-$CrtZ_{BD}$ were also prepared. The plasmid maps of pUC-pBAD-CrtI-m2-CrtY-$CrtW_{BD}$, pUC-pBAD-CrtI-m2-CrtY-$CrtZ_{BD}$, and pUC-pBAD-$CrtI_{N304P}$-CrtY-$CrtW_{BD}$-$CrtZ_{BD}$ are illustrated in FIGS. 11(*i*), 11(*j*), and 11(*k*), respectively, and the nucleotide sequences thereof are set forth in SEQ ID NOS: 16, 17, and 18, respectively.

Those plasmids were introduced into *E. coli* (XL1-Blue) together with pAC-$crtM_{F26A,W38A,F233S}$-$fds_{Y81A,V157A}$, and culturing and extraction were performed by the method shown in Example 3. The obtained carotenoid extracts were each injected into an HPLC-photodiodearray system. Analysis was performed at a flow rate of 1 mL/min by using a μBondapak column (100×8 mm, RCM-type, Waters) as a column and using methanol as an eluent.

Figure 12:
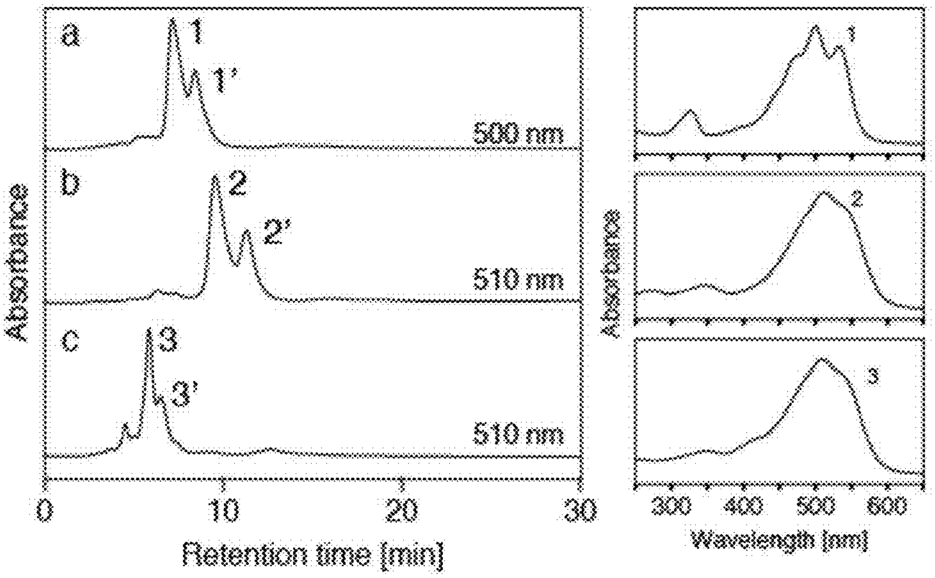
FIG. 12 shows the results of HPLC analysis of C50-zeaxanthin, C50-canthaxanthin, and C50-astaxanthin produced in the case where *E. coli* was transformed with various plasmids containing CrtW and/or CrtZ derived from *Brevundimonas* sp. strain SD-212 and pAC-crt $M_{F26A,W38A,F233S}$-$fds_{Y81A,V157A}$ and cultured (Example 8). (a), (b), and (c) show the results of transformation with pUC-pBAD-CrtI-m2-CrtY-$CrtZ_{BD}$, pUC-pBAD-CrtI-m2-CrtY-$CrtW_{BD}$, and pUC-pBAD-$CrtI_{N304P}$-CrtY-$CrtW_{BD}$-$CrtZ_{BD}$, respectively, together with pAC-crt $M_{F26A,W38A,F233S}$-$fds_{Y81A,V157A}$. Numerals 1, 2, and 3 in FIG. 12 represent the peaks of C50-zeaxanthin, C50-canthaxanthin, and C50-astaxanthin, respectively, and numerals with dashes (primes) represent cis peaks thereof.

As a result, C50-zeaxanthin was specifically synthesized in pUC-pBAD-CrtI-m2-CrtY-$CrtZ_{BD}$ (panel a in FIG. 12), and C50-canthaxanthin was specifically synthesized in the case of using pUC-pBAD-CrtI-m2-CrtY-$CrtW_{BD}$ (panel b in FIG. 12). Further, C50-astaxanthin was specifically synthesized in the case of using pUC-pBAD-$CrtI_{N304P}$-CrtY-$CrtW_{BD}$-$CrtZ_{BD}$ (panel c in FIG. 12).

Example 9

Increase in C50-Astaxanthin Amount by Co-Expression of Idi

C50-astaxanthin was synthesized in *E. coli* by the method described in Example 8 using pAC-$crtM_{F26A,W38A,F233S}$-$fds_{Y81A,V157A}$ and pUC-pBAD-$CrtI_{N304P}$-CrtY-$CrtW_{BD}$-$CrtZ_{BD}$, and a synthesis amount thereof was determined from an HPLC peak area thereof.

Figure 13:
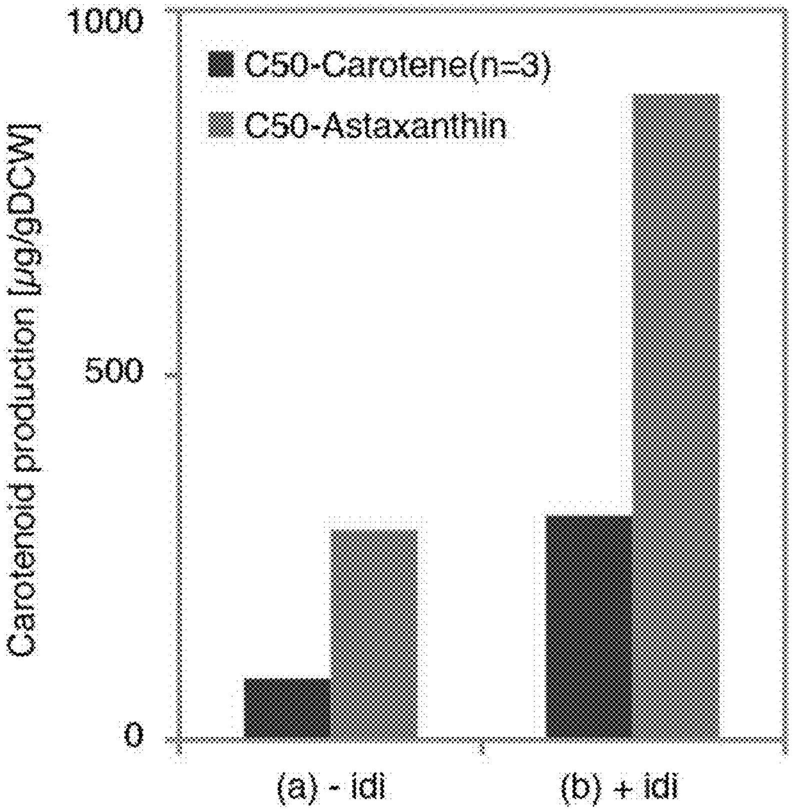
FIG. 13 shows that idi co-expression remarkably increased the synthesis amount of C50-astaxanthin in *E. coli* transformed with pUC-pBAD-$CrtI_{N304P}$-CrtY-$CrtW_{BD}$-$CrtZ_{BD}$ and pAC-$crtM_{F26A,W38A,F233S}$-$fds_{Y81A,V157A}$ (Example 9). (a) shows the results when co-expressing no idi, that is, the synthesis amounts of C50-carotene (n=3) and C50-astaxanthin in *E. coli* transformed with pAC-crt $M_{F26A,W38A,F233S}$-$fds_{Y81A,V157A}$ and pUC-pBAD-$CrtI_{N304P}$-CrtY-$CrtW_{BD}$-$CrtZ_{BD}$. (b) shows the results when co-expressing idi, that is, the synthesis amounts of C50-carotene (n=3) and C50-astaxanthin in *E. coli* transformed with pAC-$crtM_{F26A,W38A,F233S}$-$fds_{Y81A,V157A}$-idi and pUC-pBAD-$CrtI_{N304P}$-CrtY-$CrtW_{BD}$-$CrtZ_{BD}$.

As a result, C50-astaxanthin was synthesized at 288 μg/gDCW (FIG. 13).

In order to co-express idi therewith, pAC-crt $M_{F26A,W38A,F233S}$-$fds_{Y81A,V157A}$-idi was prepared and transformed into *E. coli* (XL1-Blue) together with pUC-pBAD-$CrtI_{N304P}$-CrtY-$CrtW_{BD}$-$CrtZ_{BD}$. Then, a carotenoid synthesis amount was determined by a similar method. The plasmid map of pAC-$crtM_{F26A,W38A,F233S}$-$fds_{Y81A,V157A}$-idi is illustrated in FIG. 11(*l*) and the nucleotide sequence thereof is set forth in SEQ ID NO: 19.

As a result, C50-astaxanthin was synthesized at 884 μg/gDCW (FIG. 13).

Example 10

A compound in the peak of C50-β-carotene obtained in Example 4 (peak 7 in FIG. 6 (*d*)) and compounds in the peaks of C50-zeaxanthin, C50-canthaxanthin, and C50-astaxanthin identified in Example 8 (peaks 1, 2, and 3 in FIG. 12) were identified.

The maximum absorption wavelengths of the compound in the peak (peak 7 in FIG. 6(*d*)) of C50-β-carotene were 467 (shoulder), 501, and 534 nm in methanol, which was shifted to the lower wavelength side than those of C50-lycopene. Thus, it is apparent that the compound is a carotenoid having a ring structure (Takaichi, S. & Shimada, K. Methods Enzymol. 213, 374-385 (1992)). Further, the prolonged elution time in reverse phase HPLC also indicates that cyclization occurred. The molecular mass was 668, which was identical to a value calculated for C50-β-carotene.

Figure 14:
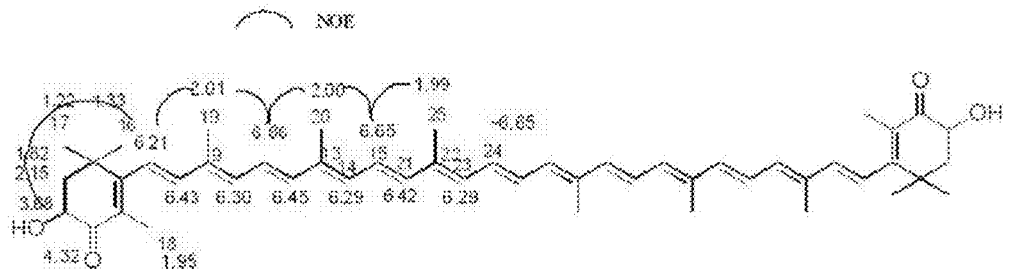
FIG. 14 shows the result of identification by NMR analysis, which indicates that a compound synthesized in *E. coli* transformed with pUC-pBAD-$CrtI_{N304P}$-CrtY-$CrtW_{BD}$-$CrtZ_{BD}$ and pAC-$crtM_{F26A,W38A,F233S}$-$fds_{Y81A,V157A}$ was C50-astaxanthin (Example 10).
Figure 14:
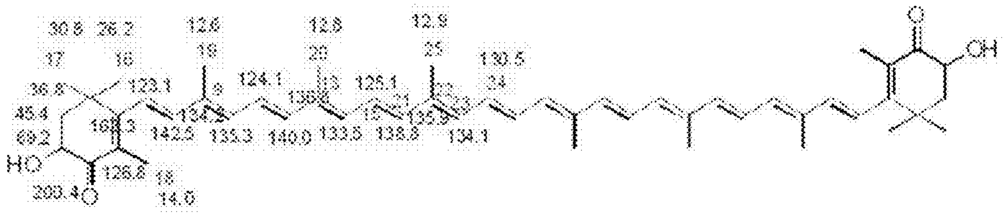

The compound in the peak (peak 3 in FIG. 12) of 50-astaxanthin gave a broad absorption spectrum having a maximum absorption wavelength at 512 nm in methanol. The molecular mass was 728, which was consistent with a value predicted from the structural formula of C50-astaxanthin. In addition, it was attempted to determine a partial structure thereof by chemical derivatization in accordance with the previous report (S. Takaichi et al., Org. Mass Spdectroscopy, 28, 785-788 (1993)). This compound, when subjected to reduction with $NaBH_4$, gave the same absorption spectrum as that of C50-β-carotene, and had a molecular mass increased to 732. This revealed the presence of two carbonyl groups at the 4,4'-positions. When the compound before $NABH_4$ treatment was used to prepare its diacetyl and ditrimethylsilyl derivatives, the molecular masses were 812 and 872, respectively. The increases correspond to increases in molecular weight of two acetyl groups and two trimethylsilyl groups, respectively. This revealed the presence of two hydroxyl groups. On the other hand, when the compound after $NABH_4$ treatment was used to prepare its diacetyl and ditrimethylsilyl derivatives in the same manner as described above, the molecular masses were 900 and 1,020, respectively. In other words, the presence of four hydroxyl groups could be confirmed. In addition, when the compound was purified and subjected to NMR analysis, the compound was clearly identified as C50-astaxanthin (FIG. 14).

The compound in the peak (peak 1 in FIG. 12) of C50-zeaxanthin had a molecular mass of 700, which HPLC elution profile and absorption spectrum were as shown in panel (a) of FIG. 12. The compound was determined as C50-zeaxanthin by considering the shift of its elution peak to the polar side and so on.

The compound in the peak (peak 2 in FIG. 12) of C50-canthaxanthin had a molecular mass of 696, which HPLC elution profile and absorption spectrum were as shown in panel (b) of FIG. 12. Thus, the compound was identified as C50-canthaxanthin in consideration of, for example, the shift of its elution peak to the polar side.

Example 11

Production of Carotenoids Having Great Variety of Structures by Additional Expression of CrtG and CrtX A study on the diversification of carotenoid structures to be synthesized was made by the additional expression of a crtG gene derived from *Brevundimonas* sp. strain SD-212 (Nishida, Y. et al, Appl Environ Microbiol 71, 4286-4296, 2005) and a crtX gene derived from *Pantoea ananatis*. The crtX gene is a gene encoding a zeaxanthin glucosyl transferase.

Figure 15:
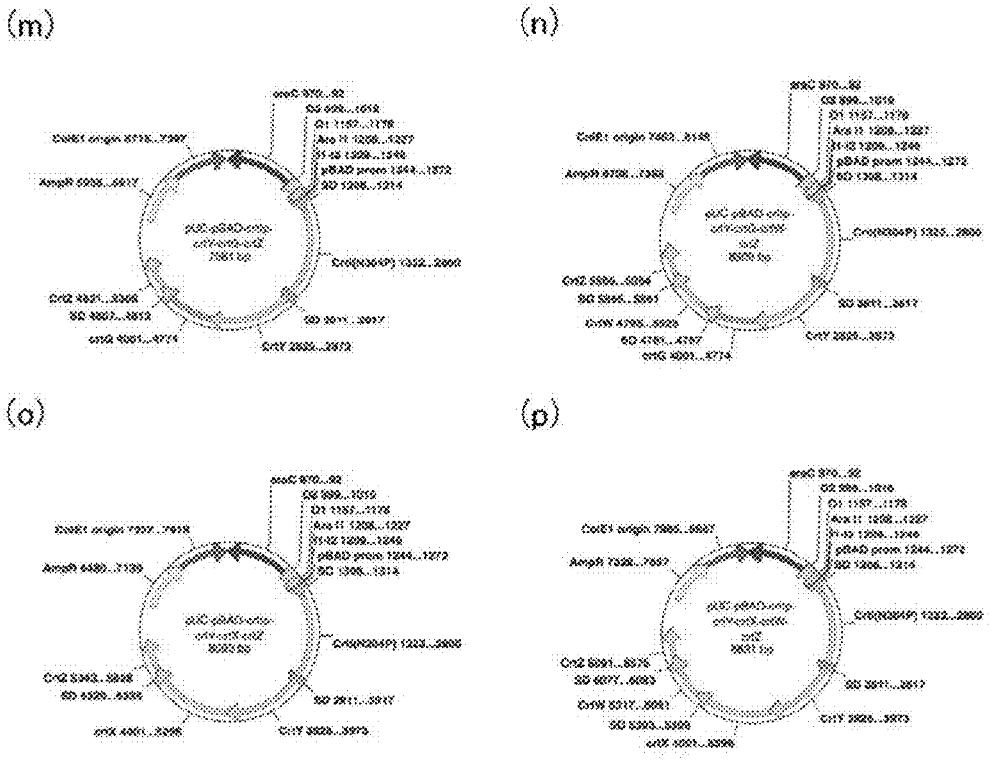
FIG. 15 illustrates plasmid maps (m)~(p) used in Example 11. The plasmids contain, in addition to CrtW and/or CrtZ derived from *Brevundimonas* sp. strain SD-212, CrtG derived from *Brevundimonas* sp. strain SD-212 or CrtX derived from *Pantoea ananatis*. (m) illustrates pUC-pBAD-$CrtI_{N304P}$-CrtY-CrtG-$CrtZ_{BD}$. (n) illustrates pUC-pBAD-$CrtI_{N304P}$-CrtY-CrtG-$CrtW_{BD}$-$CrtZ_{BD}$. (o) illustrates pUC-pBAD-$CrtI_{N304P}$-CrtY-CrtX-$CrtZ_{BD}$. (p) illustrates pUC-pBAD-$CrtI_{N304P}$-CrtY-CrtX-$CrtW_{BD}$-$CrtZ_{BD}$.

First, pUC-pBAD-CrtI$_{N304P}$-CrtY-CrtG-CrtZ$_{BD}$ and pUC-pBAD-CrtI$_{N304P}$-CrtY-CrtG-CrtW$_{BD}$-CrtZ$_{BD}$ were prepared by using the crtG gene derived from *Brevundimonas* sp. strain SD-212. The plasmid maps of pUC-pBAD-CrtI$_{N304P}$-CrtY-CrtG-CrtZ$_{BD}$ and pUC-pBAD-CrtI$_{N304P}$-CrtY-CrtG-CrtW$_{BD}$-CrtZ$_{BD}$ are illustrated in FIGS. 15(*m*) and 15(*n*), respectively, and the nucleotide sequences thereof are set forth in SEQ ID NOS: 20 and 21, respectively.

Figure 16:
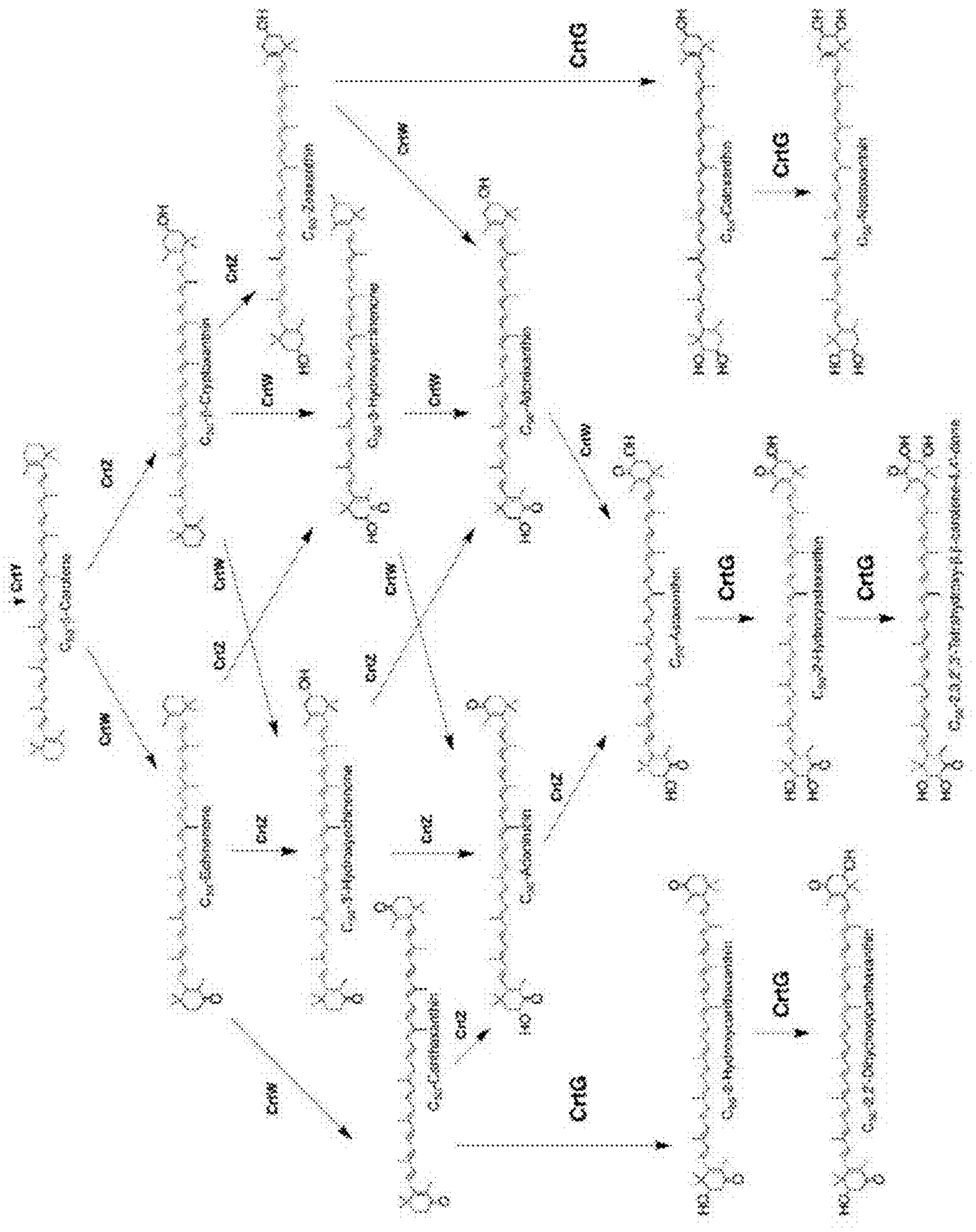
FIG. 16 illustrates that more varieties of carotenoids can be produced by the additional expression of CrtG in carotenoid biosynthetic pathways (Example 11). Through the additional expression of CrtG, $C_{50}$-2-hydroxyastaxanthin and $C_{50}$-2,3,2',3'-tetrahydroxy-β,β-carotene-4,4'-dione are produced from $C_{50}$-astaxanthin. $C_{50}$-caloxanthin and $C_{50}$-nostoxanthin are produced from $C_{50}$-zeaxanthin. Further, $C_{50}$-2-hydroxycanthaxanthin and $C_{50}$-2,2'-dihydroxycanthaxanthin are produced from $C_{50}$-canthaxanthin.

In the case of culturing *E. coli* co-expressing pUC-pBAD-CrtI$_{N304P}$-CrtY-CrtG-CrtZ$_{BD}$ and pAC-Crt M$_{F26A,W38A,F233S}$-FDS$_{Y81A,V157A}$, $C_{50}$-caloxanthin and $C_{50}$-nostoxanthin, which are hydroxylated zeaxanthin at the 2-position and 2'-position, can be synthesized (FIG. 16).

In the case of culturing *E. coli* co-expressing pUC-pBAD-CrtI$_{N304P}$-CrtY-CrtG-CrtW$_{BD}$-CrtZ$_{BD}$ and pAC-Crt M$_{F26A,W38A,F233S}$-FDS$_{Y81A,V157A}$, $C_{50}$-2-hydroxyastaxanthin and $C_{50}$-2,3,2',3'-tetrahydroxy-β,β-carotene-4,4'-dione, which are hydroxylated astaxanthin at the 2-position and 2'-position, can be synthesized (FIG. 16).

Further, it is also possible to synthesize $C_{50}$-2-hydroxycanthaxanthin and $C_{50}$-2,2'-dihydroxycanthaxanthin, which are hydroxylated canthaxanthin at the 2-position and 2'-position (FIG. 16).

Next, pUC-pBAD-CrtI$_{N304P}$-CrtY-CrtX-CrtZ$_{BD}$ and pUC-pBAD-CrtI$_{N304P}$-CrtY-CrtX-CrtW$_{BD}$-CrtZ$_{BD}$ were prepared by using the crtX gene derived from *Pantoea ananatis*. The plasmid maps of pUC-pBAD-CrtI$_{N304P}$-CrtY-CrtX-CrtZ$_{BD}$ and pUC-pBAD-CrtI$_{N304P}$-CrtY-CrtX-CrtW$_{BD}$-CrtZ$_{BD}$ are illustrated in FIGS. 15(*o*) and 15(*p*), respectively, and the nucleotide sequences thereof are set forth in SEQ ID NOS: 22 and 23, respectively.

Figure 17:
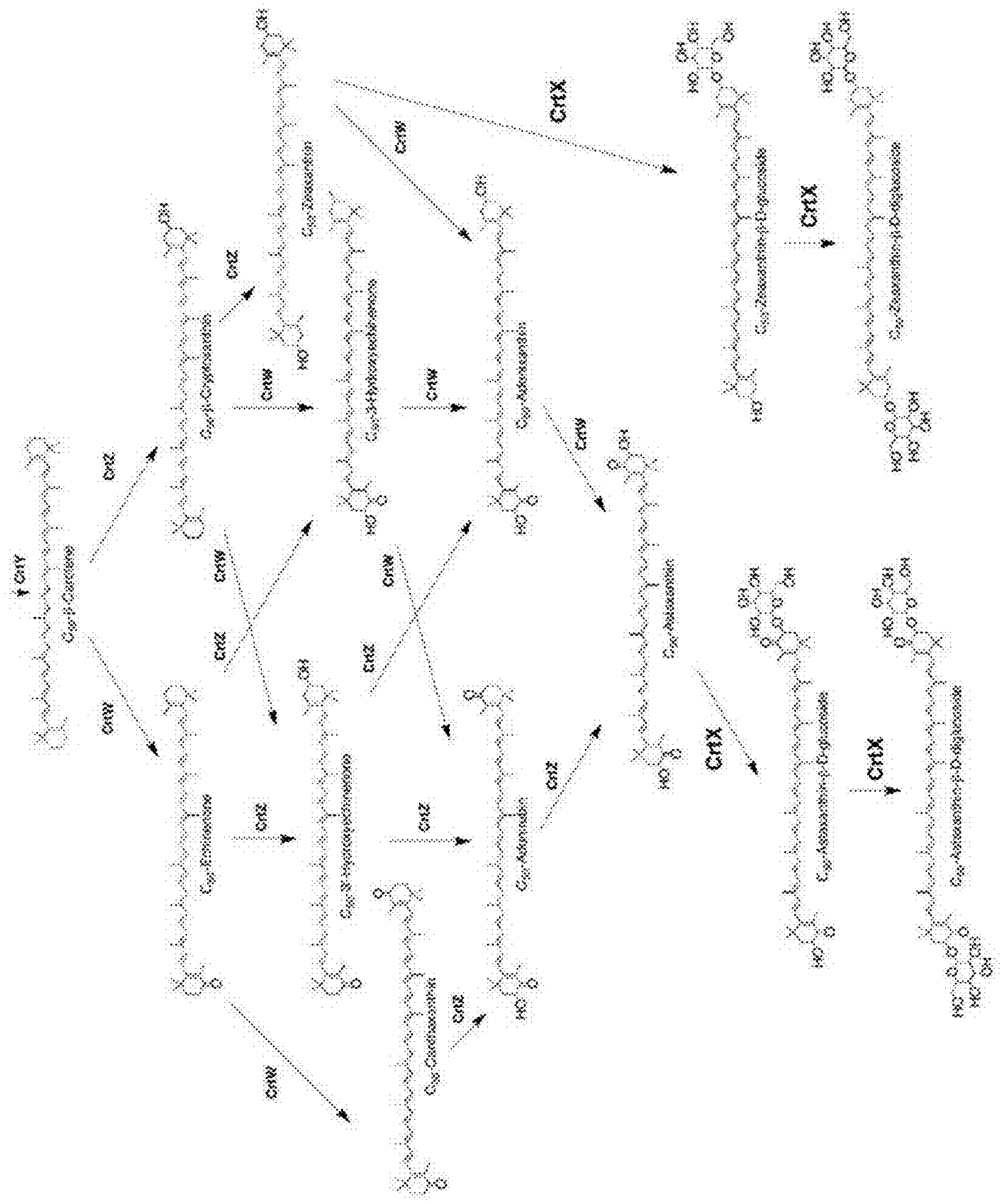
FIG. 17 illustrates that more varieties of carotenoids can be produced by the additional expression of CrtX in carotenoid biosynthetic pathways (Example 11). Through the additional expression of CrtX, $C_{50}$-astaxanthin-β-D-glucoside and $C_{50}$-astaxanthin-β-D-diglucoside are produced from $C_{50}$-astaxanthin. $C_{50}$-zeaxanthin-β-D-glucoside and $C_{50}$-zeaxanthin-β-D-diglucoside are produced from $C_{50}$-zeaxanthin.

In the case of culturing *E. coli* co-expressing pUC-pBAD-CrtI$_{N304P}$-CrtY-CrtX-CrtZ$_{BD}$ and pAC-Crt M$_{F26A,W38A,F233S}$-FDS$_{Y81A,V157A}$, $C_{50}$-zeaxanthin-β-D-glucoside and $C_{50}$-zeaxanthin-β-D-diglucoside, which are glycosidated zeaxanthin at the hydroxyl groups at the 3-position and 3'-position, can be synthesized (FIG. 17).

In the case of culturing *E. coli* co-expressing pUC-pBAD-CrtI$_{N304P}$-CrtY-CrtX-CrtW$_{BD}$-CrtZ$_{BD}$ and pAC-Crt M$_{F26A,W38A,F233S}$-FDS$_{Y81A,V157A}$, $C_{50}$-astaxanthin-β-D-glucoside and $C_{50}$-astaxanthin-β-D-diglucoside, which are glycosidated astaxanthin at the hydroxyl groups at the 3-position and 3'-position, can be synthesized (FIG. 17).

Figure 18:
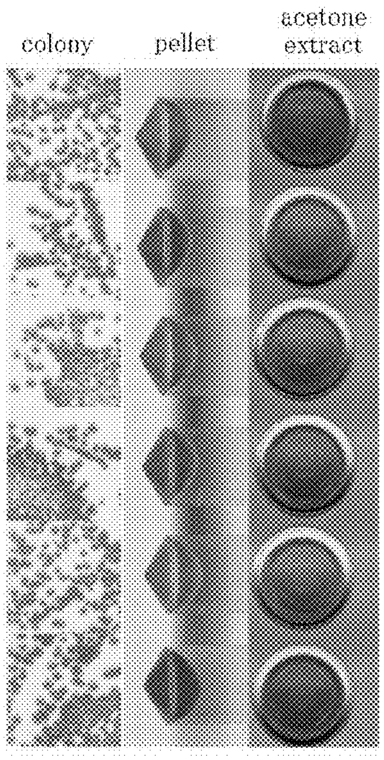
FIG. 18 shows the results of confirmation of the fact that a great variety of carotenoids were able to be produced by the additional expression of CrtG or CrtX in *E. coli* strains that specifically synthesize C50-zeaxanthin and C50-astaxanthin, based on colony colors, cell pellet colors, and carotenoid extract colors (Example 11).

In fact, when *E. coli* (XL1-Blue) co-expressing any one of pUC-pBAD-CrtI$_{N304P}$-CrtY-CrtG-CrtZ$_{BD}$, pUC-pBAD-CrtI$_{N304P}$-CrtY-CrtX-CrtZ$_{BD}$, pUC-pBAD-CrtI$_{N304P}$-CrtY-CrtG-CrtW$_{BD}$-CrtZ$_{BD}$, and pUC-pBAD-CrtI$_{N304P}$-CrtY-CrtX-CrtW$_{BD}$-CrtZ$_{BD}$ together with pAC-Crt M$_{F26A,W38A,F233S}$-FDS$_{Y81A,V157A}$ was spread on an LB solid medium to form colonies, the formed colonies developed a reddish violet color (FIG. 18).

Figure 19:
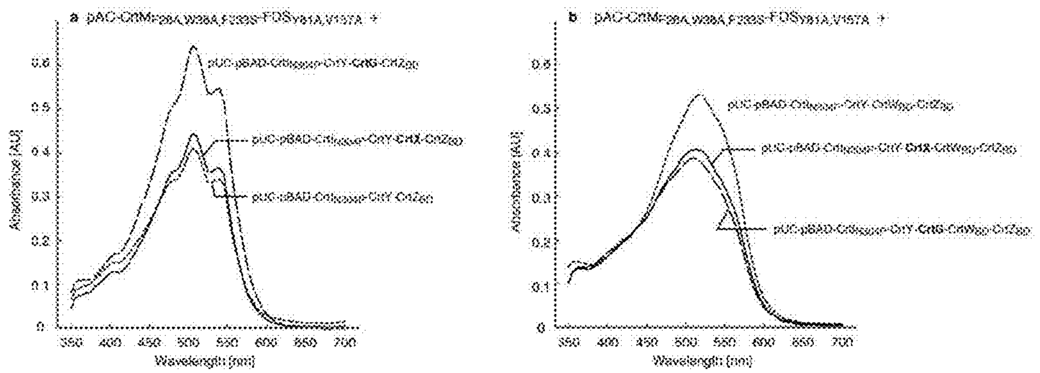
FIG. 19 shows the results of measurement of absorption spectra of carotenoid extracts obtained by the additional expression of CrtG or CrtX in *E. coli* strains that specifically synthesize C50-zeaxanthin and C50-astaxanthin (Example 11).

The colonies were inoculated into 2 mL of an LB liquid medium and cultured for 16 hours. After that, the culture medium was inoculated into 30 mL of a TB liquid medium in a 1/100 volume with respect to the TB liquid medium. After incubation under rotation at 200 rpm at 30° C. for 36 hours, L-arabinose was added so as to have a final concentration of 0.2% (v/v), followed by incubation for an additional 36 hours. The cells were harvested and collected from 2 mL of the culture medium and washed with physiological saline, and then a carotenoid fraction was extracted with the addition of 1 mL of acetone. FIG. 18 shows the cell pellets and the acetone extracts. Further, FIG. 19 shows the absorption spectra of the respective extracts.

Next, *E. coli* (XL1-Blue) was transformed with pUC-pBAD-CrtI$_{N304P}$-CrtY-CrtX-CrtZ$_{BD}$ or pUC-pBAD-CrtI$_{N304P}$-CrtY-CrtG-CrtZ$_{BD}$ and pAC-Crt M$_{F26A,W38A,F233S}$-FDS$_{Y81A,V157A}$. The cell colonies were inoculated into 2 mL of an LB liquid medium and cultured for 16 hours. After that, the culture medium was inoculated into 30 mL of a TB liquid medium in a 1/100 volume with respect to the TB liquid medium. After incubation under rotation at 200 rpm at 30° C. for 36 hours, L-arabinose was added so as to have a final concentration of 0.2% (v/v), followed by incubation for an additional 36 hours. The cells were harvested by centrifuging the culture medium and washed with physiological saline. 10 mL of acetone were added to the cell pellet to extract a carotenoid fraction. 1 mL of chloroform and 35 mL of 10% NaCl were added to the acetone extract to extract the carotenoid fraction into a chloroform phase. All the chloroform extracts were collected and dehydrated with the addition of $MgSO_4$. The chloroform solvent was eliminated by nitrogen, and the carotenoid fraction was finally concentrated into 100 μL of methanol/THF (1:1, v/v). Thus, a carotenoid extract was obtained. 10 μL (10% of the total volume, corresponding to 3 mL of the medium) of the obtained carotenoid extract were injected into an HPLC-photodiodearray system. HPLC analysis was performed in accordance with the conditions of Nishida, Y. et al, Appl Environ Microbiol, 71, 4286-4296 (2005) (column: TSK gel ODS-80Ts column (4.6-mm inner diameter by 150 mm; Tosoh Co.), eluent: Eluent A (methanol/water, 95:5) for 5 minutes, Eluent A to Eluent B (methanol/tetrahydrofuran, 7:3) for 5 minutes, Eluent B for 15 minutes, 1 mL/min, detector: photodiode array (190 to 800 nm)).

Figure 20:
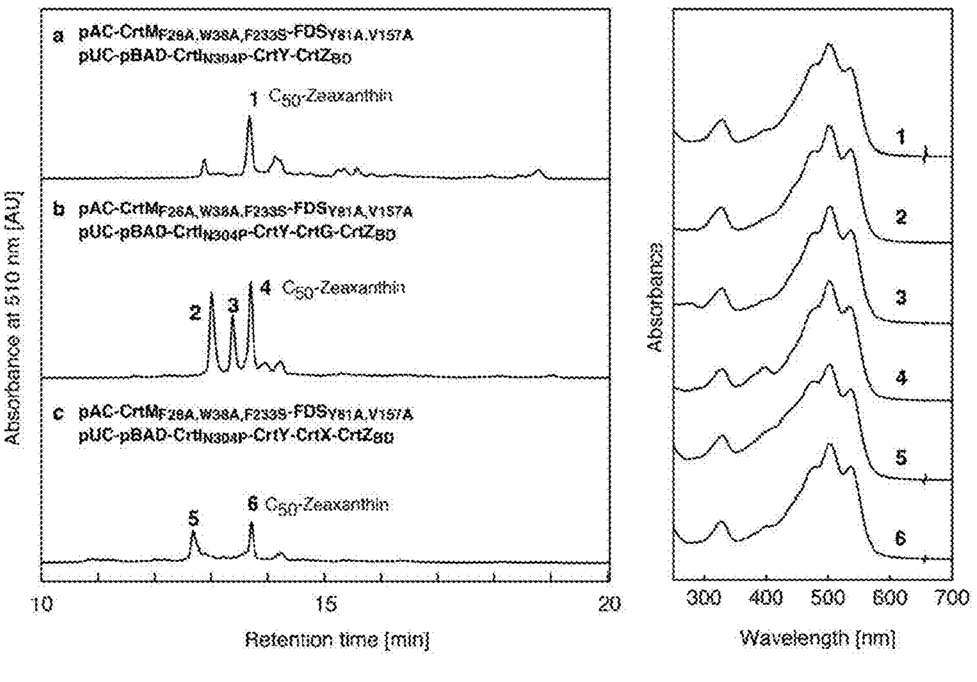
FIG. 20 show the results of HPLC analysis of a carotenoid produced by the additional expression of CrtG or CrtX in an *E. coli* strain that specifically synthesizes C50-zeaxanthin (Example 11).

As a result, in the case of co-expression of CrtX with C50-zeaxanthin, one new peak appeared at a shorter elution time (peak 5 in FIG. 20). A compound in the peak is estimated to be C50-zeaxanthin-β-D-diglucoside because of having the same absorption spectrum as that of C50-zeaxanthin and having higher polarity than that of C50-zeaxanthin.

Further, in the case of co-expression of CrtG with C50-zeaxanthin, two new peaks appeared (peaks 2 and 3 in FIG. 20). Compounds in the peaks are estimated to be C50-caloxanthin (peak 3 in FIG. 20) and C50-nostoxanthin (peak 2 in FIG. 20) because of, for example, having the same absorption spectrum as that of C50-zeaxanthin and having higher polarity.

Example 12

Biosynthesis of $C_{55}$ and $C_{60}$ Carotenoids

A mutant FDS having introduced therein mutations I78G and Y81A ($FDS_{I78G,Y81A}$) synthesizes $C_{25}$PP and a prenyl diphosphate (e.g., $C_{30}$PP or $C_{35}$PP) which is a resultant of further addition of $C_5$ unit(s) to $C_{25}$PP (Ohnuma S et al., J Biol Chem 273, 26705-26713, 1998). Further, a $C_{30}$PP synthase (HexPS) derived from *Micrococcus luteus* synthesizes $C_{30}$PP (Shimizu N et al, J Bacteriol 180, 1578-1581, 1998). The biosynthesis of a larger carotenoid backbone than a $C_{50}$ backbone was attempted by co-expressing $FDS_{I78G,Y81A}$ or HexPS with a CrtM variant.

First, pAC-hexPS, pAC-$FDS_{I78G,Y81A}$-idi, and pUC-$CrtM_{F26A,W38A,F233S}$ were prepared. The plasmid maps of pAC-hexPS, pAC-$FDS_{I78G,Y81A}$-idi, and pUC-Crt$M_{F26A,W38A,F233S}$ are illustrated in FIGS. 20(*q*), 20(*r*), and 20(*s*), respectively, and the nucleotide sequences thereof are set forth in SEQ ID NOS: 24, 25, and 26, respectively.

*E. coli* (XL1-Blue) was transformed with pAC-FD$S_{I78G,Y81A}$-idi or pAC-hexPS together with pUC-$CrtM_{F26A,W38A}$ or pUC-$CrtM_{F26A,W38A,F233S}$. The culturing of the cells and the analysis of the produced carotenoid were performed in the same manner as in Reference Example 1.

Figure 21:
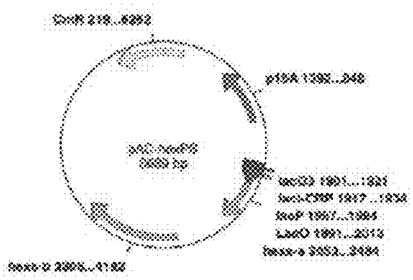
FIG. 21 illustrate plasmid maps (q)~(s) used in Example 12. (q) illustrates pAC-hexPS. (r) illustrates pAC-$FDS_{I78G,Y81A}$-idi. (s) illustrates pUC-$CrtM_{F26A,W38A,F233S}$.
Figure 21:
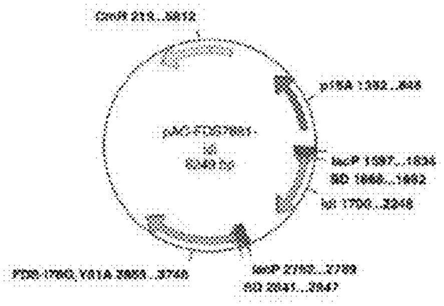
Figure 21:
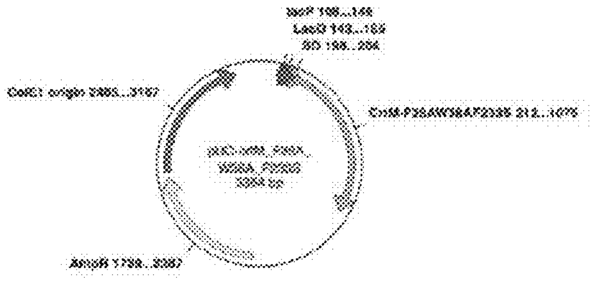

FIG. 21 shows the results. In the case of using CrtMF26A, W38A,F233S, a $C_{55}$ carotenoid was produced in addition to $C_{45}$ and $C_{50}$ carotenoids under co-expression of pAC-$FDS_{I78G,Y81A}$-idi therewith. Further, a $C_{60}$ carotenoid was specifically synthesized under co-expression of hexPS therewith. On the other hand, in the case of using $CrtM_{F26A,W38A}$, it was impossible to confirm the production of any of the $C_{55}$ carotenoid and the $C_{60}$ carotenoid. Accordingly, the F233S mutation of CrtM is essential for the production of the $C_{55}$ carotenoid and the $C_{60}$ carotenoid.

Figure 22:
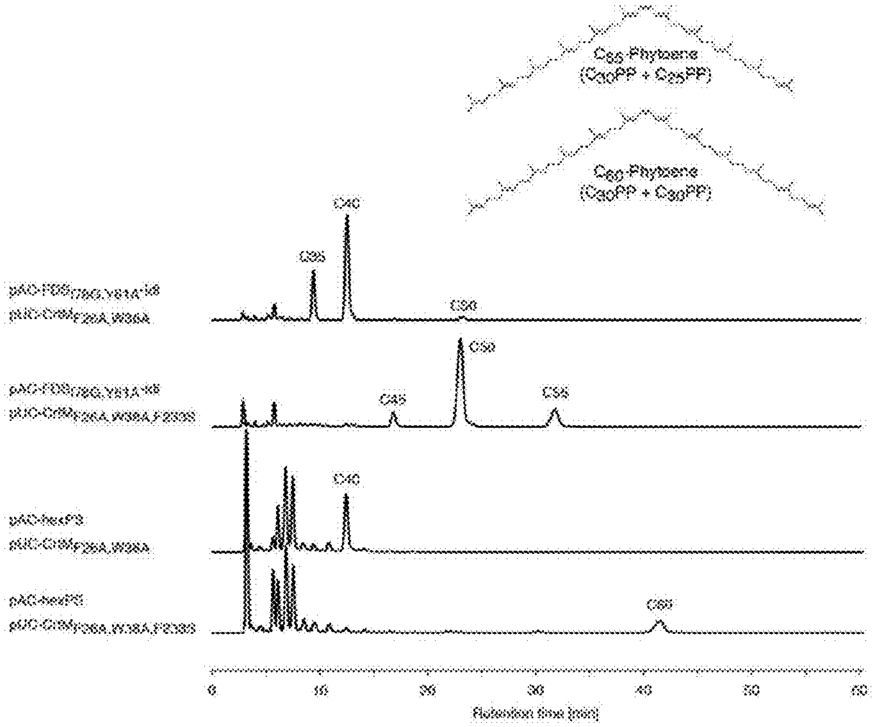
FIG. 22 shows the results of biosynthesis of a $C_{55}$ carotenoid and a $C_{60}$ carotenoid (Example 12). When co-expressing $CrtM_{F26A,W38A,F233S}$ with pAC-$FDS_{I78G,Y81A}$-idi, the $C_{55}$ carotenoid was produced in addition to $C_{45}$ and $C_{50}$ carotenoids. Further, when co-expressing $CrtM_{F26A,W38A,F233S}$ with hexPS, the $C_{60}$ carotenoid was specifically synthesized. On the other hand, when using $CrtM_{F26A,W38A}$, it was impossible to confirm the production of any of the $C_{55}$ carotenoid and the $C_{60}$ carotenoid.
Figure 23:
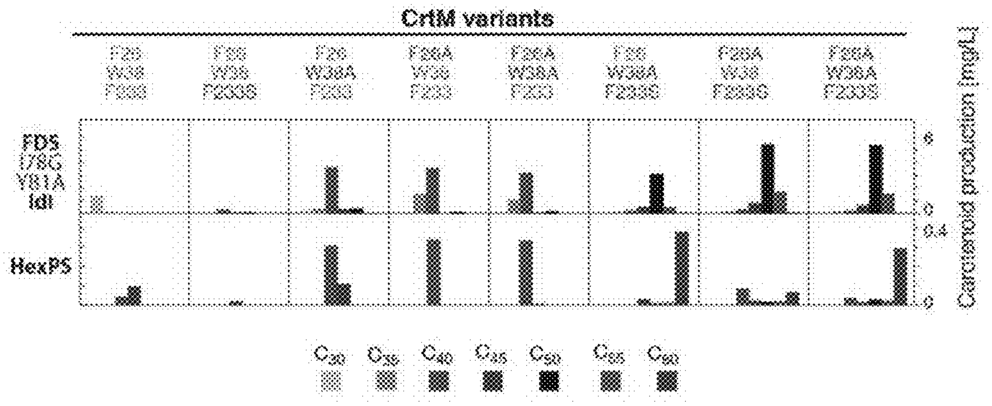
FIG. 23 shows the results of measurement of carotenoid synthesis amounts when co-expressing AC-$FDS_{I78G,Y81A}$-idi or pAC-hexPS with 8 kinds of CrtM variants (pUC-CrtM variants) (Example 12). A larger amount of a $C_{55}$ carotenoid was synthesized in cells co-expressing $FDS_{I78G,Y81A}$-idi with $CrtM_{F26A,F233S}$ or $CrtM_{F26A,W38A,F233S}$. Further, a larger amount of a $C_{60}$ carotenoid was synthesized in cells co-expressing HexPS with $CrtM_{W38A,F233S}$ or $CrtM_{F26A,W38A,F233S}$.

Next, pAC-$FDS_{I78G,Y81A}$-idi or pAC-hexPS was co-expressed with 8 kinds of CrtM variants (pUC-CrtM variants), and carotenoid synthesis amounts thereof were investigated by a similar method. FIG. 22 shows the results. The $C_{55}$ backbone was synthesized in a larger amount in the cells co-expressing $FDS_{I78G,Y81A}$-idi with $CrtM_{F26A,F233S}$ or $CrtM_{F26A,W38A,F233S}$. The $C_{60}$ backbone was efficiently synthesized in the cells co-expressing HexPS with $CrtM_{W38A,F233S}$ or $CrtM_{F26A,W38A,F233S}$.

INDUSTRIAL APPLICABILITY

As described above, the production method of the present invention can synthesize the desaturated $C_{50}$ carotenoid in an extremely efficient manner, and allows various $C_{50}$ carotenoids to be synthesized. The $C_{50}$ carotenoid is rarely found in nature, and it is not too much to say that there is no synthesis example thereof. Carotenoids are known to have physiological activities such as an antioxidant action. Of those, the $C_{50}$ carotenoid is expected to exhibit unprecedented novel actions and to have remarkably enhanced activities as compared to conventional carotenoids. For example, the $C_{50}$ carotenoid is expected to have the potentiality of having a high antioxidant activity, an application as a novel seed for a physiologically active substance having an antitumor activity or the like, and a use as a functional pigment molecule. Further, the production method of the present invention may be utilized in the highly efficient synthesis of the desaturated $C_{55}$ carotenoid, the desaturated $C_{60}$ carotenoid, and the like. In addition, the production method of the present invention is considered to drastically increase variety of synthesizable carotenoids, by being used in combination with related art such as cells having an enhanced isoprenoid synthetic pathway (Klein-Marcuschamer D et al.: Trends Biotechnol 25, 417-424 (2007), Kirby J et al.: Nat Prod Rep 25, 656-661 (2008)).

What is claimed is:

1. A method of producing a carotenoid having 50 carbon atoms, comprising:

culturing in vitro, in a medium, a single cell organism transformed with a mutant phytoene desaturase gene; and obtaining the carotenoid having 50 carbon atoms from a culture after the culturing;

wherein the mutant phytoene desaturase gene has an introduced mutation to encode a mutant phytoene desaturase having an enhanced activity to desaturate a carotenoid backbone compound of 50 carbon atoms; and the mutation causes at least a substitution of an amino acid corresponding to asparagine at position 304 in SEQ ID NO: 1 by proline or serine, and the mutation consists of one or more substitutions at positions 228, 304, 338, 339, and 395 of SEQ ID NO: 1.

2. A method of producing a carotenoid having 50 carbon atoms, comprising:

culturing in vitro, in a medium, a single cell organism transformed with a mutant phytoene desaturase gene; and obtaining the carotenoid having 50 carbon atoms from a culture after the culturing;

wherein the mutant phytoene desaturase gene has an introduced mutation to encode a mutant phytoene desaturase having an enhanced activity to desaturate a carotenoid backbone compound of 50 carbon atoms; and the mutation causes a substitution of an amino acid corresponding to at least one amino acid selected from asparagine at position 304, phenylalanine at position 339, isoleucine at position 338, aspartic acid at position 395, and isoleucine at position 228 in the amino acid sequence of SEQ ID NO: 1, and the mutation consists of one or more substitutions at positions 228, 304, 338, 339, and 395 of SEQ ID NO: 1.

3. The method of producing a carotenoid having 50 carbon atoms according to claim 1, wherein:

the mutant phytoene desaturase gene is obtained by introducing the mutation into a phytoene desaturase gene from *Pantoea ananatis*.

4. The method of producing a carotenoid having 50 carbon atoms according to claim 1, wherein the single cell organism is *Escherichia coli* or yeast.

5. The method of producing a carotenoid having 50 carbon atoms according to claim 1, wherein the single cell organism as defined in claim 1 is further transformed with a gene encoding an enzyme that synthesizes the carotenoid backbone compound of 50 carbon atoms via condensation of two molecules of geranylfarnesyl diphosphate.

6. The method of producing a carotenoid having 50 carbon atoms according to claim 1, wherein the single cell organism as defined in claim 1 is further transformed with a gene encoding an enzyme that synthesizes geranylfarnesyl diphosphate from farnesyl diphosphate or geranylgeranyl diphosphate, or both.

7. The method of producing a carotenoid having 50 carbon atoms according to claim 1, wherein the single cell organism as defined in claim 1 is further transformed with a gene encoding an enzyme that cyclizes ends of a desaturated carotenoid having 50 carbon atoms obtained by desaturating the carotenoid backbone compound of 50 carbon atoms.

8. The method of producing a carotenoid having 50 carbon atoms according to claim 7, wherein:

the cyclization as defined in claim 7 comprises β-cyclization; and the single cell organism as defined in claim 7 is further transformed with a gene encoding an enzyme that hydroxylates a β-ring or an enzyme that ketolates a β-ring in a carotenoid having 50 carbon atoms and having the β-ring at an end thereof, or both.

9. The method of producing a carotenoid having 50 carbon atoms according to claim 1, wherein the single cell organism as defined in claim 1 is further transformed with a gene encoding an enzyme that oxidizes a desaturated carotenoid having 50 carbon atoms obtained by desaturating the carotenoid backbone compound of 50 carbon atoms.

10. A mutant phytoene desaturase gene, into which a mutation to encode a mutant phytoene desaturase having an enhanced activity to desaturate a carotenoid backbone compound of 50 carbon atoms has been introduced, wherein the mutation of the mutant phytoene desaturase gene causes at least a substitution of an amino acid corresponding to asparagine at position 304 in SEQ ID NO: 1 by proline or serine, and the mutation consists of one or more substitutions at positions 228, 304, 338, 339, and 395 of SEQ ID NO: 1.

11. A mutant phytoene desaturase gene, into which a mutation to encode a mutant phytoene desaturase having an enhanced activity to desaturate a carotenoid backbone compound of 50 carbon atoms has been introduced, wherein the mutation of the mutant phytoene desaturase gene causes a substitution of an amino acid corresponding to at least one amino acid selected from asparagine at position 304, phenylalanine at position 339, isoleucine at position 338, aspartic acid at position 395, and isoleucine at position 228 in the amino acid sequence of SEQ ID NO: 1, and the mutation consists of one or more substitutions at positions 228, 304, 338, 339, and 395 of SEQ ID NO: 1.

12. A mutant phytoene desaturase, which is encoded by a mutant phytoene desaturase gene according to claim 10.

13. A single cell organism producing a carotenoid having 50 carbon atoms by desaturating a carotenoid backbone compound of 50 carbon atoms, which is transformed with the mutant phytoene desaturase gene according to claim 10.

14. A method of producing a carotenoid having 50 carbon atoms, comprising:

culturing in vitro, in a medium, a single cell organism transformed with a mutant phytoene desaturase gene; and obtaining the carotenoid having 50 carbon atoms from a culture after the culturing;

wherein the mutant phytoene desaturase gene has an introduced mutation to encode a mutant phytoene desaturase having an enhanced activity to desaturate a carotenoid backbone compound of 50 carbon atoms; and the mutation causes a substitution of an amino acid corresponding to phenylalanine at position 339 in SEQ ID NO: 1 by serine, a substitution of an amino acid corresponding to asparagine at position 304 by serine, substitutions of an amino acid corresponding to phenylalanine at position 339 by lysine and an amino acid corresponding to aspartic acid at position 395 with asparagine, substitutions of an amino acid corresponding to isoleucine at position 228 by valine and an amino acid corresponding to isoleucine at position 338 by valine, or a substitution of an amino acid corresponding to isoleucine at position 338 by valine, and the mutation consists of one or more substitutions at positions 228, 304, 338, 339, and 395 of SEQ ID NO: 1.

15. A mutant phytoene desaturase gene, into which a mutation to encode a mutant phytoene desaturase having an enhanced activity to desaturate a carotenoid backbone compound of 50 carbon atoms has been introduced, wherein the mutation of the mutant phytoene desaturase gene causes a substitution of an amino acid corresponding to phenylalanine at position 339 in SEQ ID NO: 1 by serine, a substitution of an amino acid corresponding to asparagine at position 304 by serine, substitutions of an amino acid corresponding to phenylalanine at position 339 by lysine and an amino acid corresponding to aspartic acid at position 395 with asparagine, substitutions of an amino acid corresponding to isoleucine at position 228 by valine and an amino acid corresponding to isoleucine at position 338 by valine, or a substitution of an amino acid corresponding to isoleucine at position 338 by valine, and the mutation consists of one or more substitutions at positions 228, 304, 338, 339, and 395 of SEQ ID NO: 1.

16. A mutant phytoene desaturase, which is encoded by the mutant phytoene desaturase gene according to claim 15.

17. A cell producing a carotenoid having 50 carbon atoms by desaturating a carotenoid backbone compound of 50 carbon atoms, which is transformed with the mutant phytoene desaturase gene according to claim 15.

* * * * *